(12) United States Patent
Smutzer et al.

(10) Patent No.: US 11,896,037 B2
(45) Date of Patent: Feb. 13, 2024

(54) MICROENCAPSULATION OF ACTIVE AGENTS

(71) Applicant: Temple University-Of The Commonwealth System of Higher Education, Philadelphia, PA (US)

(72) Inventors: Gregory S. Smutzer, Lansdowne, PA (US); Kevin Lee, Hatfield, PA (US); Dhruti Patel, Bensalem, PA (US)

(73) Assignee: Temple University-Of The Commonwealth System of Higher Education, Philadelphia, PA (US)

( * ) Notice: Subject to any disclaimer, the term of this patent is extended or adjusted under 35 U.S.C. 154(b) by 1119 days.

(21) Appl. No.: 16/323,018

(22) PCT Filed: Aug. 3, 2017

(86) PCT No.: PCT/US2017/045244
§ 371 (c)(1),
(2) Date: Feb. 4, 2019

(87) PCT Pub. No.: WO2018/027001
PCT Pub. Date: Feb. 8, 2018

(65) Prior Publication Data
US 2019/0200659 A1 Jul. 4, 2019

Related U.S. Application Data

(60) Provisional application No. 62/370,427, filed on Aug. 3, 2016.

(51) Int. Cl.
| | | |
|---|---|---|
| A23L 27/00 | (2016.01) | |
| A23P 10/35 | (2016.01) | |
| A61K 8/60 | (2006.01) | |
| A23G 1/54 | (2006.01) | |
| A61K 8/11 | (2006.01) | |
| A61Q 11/00 | (2006.01) | |
| A61K 8/42 | (2006.01) | |
| A23G 4/20 | (2006.01) | |
| A61K 8/92 | (2006.01) | |
| A23G 1/00 | (2006.01) | |
| A23G 9/48 | (2006.01) | |
| A61K 8/36 | (2006.01) | |
| A61K 9/50 | (2006.01) | |
| A61K 9/00 | (2006.01) | |
| A23G 3/54 | (2006.01) | |
| A23L 27/30 | (2016.01) | |
| A01N 25/00 | (2006.01) | |
| A01N 25/28 | (2006.01) | |

(52) U.S. Cl.
CPC ............ *A23L 27/72* (2016.08); *A01N 25/002* (2013.01); *A01N 25/28* (2013.01); *A23G 1/00* (2013.01); *A23G 1/54* (2013.01); *A23G 3/54* (2013.01); *A23G 4/20* (2013.01); *A23G 9/48* (2013.01); *A23L 27/30* (2016.08); *A23L 27/79* (2016.08); *A23L 27/86* (2016.08); *A23P 10/35* (2016.08); *A61K 8/11* (2013.01); *A61K 8/361* (2013.01); *A61K 8/42* (2013.01); *A61K 8/60* (2013.01); *A61K 8/922* (2013.01); *A61K 9/0056* (2013.01); *A61K 9/5015* (2013.01); *A61Q 11/00* (2013.01); *A23V 2002/00* (2013.01); *A61K 2800/412* (2013.01)

(58) Field of Classification Search
CPC .......... A23L 27/72; A23L 27/30; A23L 27/79; A23L 27/86; A01N 25/002; A01N 25/28; A23G 1/00; A23G 1/54; A23G 3/54; A23G 4/20; A23G 9/48; A23P 10/35; A61K 8/11; A61K 8/361; A61K 8/42; A61K 8/60; A61K 8/922; A61K 9/0056; A61K 9/5015; A61K 2800/412; A61Q 11/00; A23V 2002/00
See application file for complete search history.

(56) References Cited

U.S. PATENT DOCUMENTS

| | | |
|---|---|---|
| 4,911,952 A | 3/1990 | Doane |
| 4,971,797 A | 11/1990 | Cherukuri |
| 5,108,763 A | 4/1992 | Chau |
| 5,139,798 A | 8/1992 | Yatka |
| 5,174,998 A | 12/1992 | Ijitsu |
| 5,660,830 A | 8/1997 | Anderson |
| 6,248,363 B1 | 6/2001 | Patel |
| 8,946,161 B2 | 2/2015 | Hinderer |
| 2003/0152629 A1 | 8/2003 | Shefer |
| 2004/0137060 A1* | 7/2004 | Fogarty ............... A61K 31/401 424/469 |
| 2005/0136121 A1 | 6/2005 | Kershman |
| 2011/0305768 A1 | 12/2011 | Mao |
| 2013/0071479 A1 | 3/2013 | Freers |
| 2014/0356420 A1 | 12/2014 | Huang |

FOREIGN PATENT DOCUMENTS

| | | | | | |
|---|---|---|---|---|---|
| WO | WO-9917743 A1 * | 4/1999 | ........... A61K 9/1641 |
| WO | WO-2006061846 A1 * | 6/2006 | ........... A61K 9/1617 |
| WO | WO-2014108569 A1 * | 7/2014 | ........... A61K 31/192 |

OTHER PUBLICATIONS

Ebba et al., The examination of fatty acid taste with edible strips, 2012, Physiol Behav. 106(5): 579-86.
Youssef et.al., Kinetic spectrophotometric methods for the determination of artificial sweetener (sucralose) in tablets, 2010, Drug Test and Analysis, 3:214-220.
Bartoshuk et al., Valid across-group comparisons with labeled scales: the gLMS versus magnitude matching, 2004, Physiology & Behavior, 82: 109-114.

(Continued)

*Primary Examiner* — Robert S Cabral
(74) *Attorney, Agent, or Firm* — Riverside Law LLP

(57) ABSTRACT

The present invention relates to compositions and methods for masking the taste of an agent. In certain aspects, the invention comprises a microsphere and at least one sweetener therein. In another aspect, the invention comprises an edible material comprising at least one microsphere comprising an agent and at least one microsphere comprising a sweetener.

15 Claims, 30 Drawing Sheets

(56) References Cited

OTHER PUBLICATIONS

Kim and Pack, Microspheres for drug delivery, BioMEMS and Biomedical Nanotechnology, 19-50 (Mauro Ferrari, Abraham P. Lee, L. James Lee, eds.) (2006).

Qi et al., An Investigation into the Interaction between Taste Masking Fatty Acid Microspheres and Alkaline Buffer using Thermal and Spectroscopic Analysis, 2006, J Pharm Sci 95(5):1022-8.

Mariam Masuda, Microencapsulation of Pesticides for Controlling Release from Coatings,. Chalmers University of Technology, Dissertation, Mar. 2011, http://publications.lib.chalmers.se/records/fulltext/136382.pdf, 71 pages.

Smutzer et al., Suppression of Bitter Taste by Stearic Acid Microspheres that are Embedded in Edible Taste Strips, Abstract, 2016, Chem. Senses 41: e71, 110 pages.

Smutzer et al., Suppression of Bitter Taste by Stearic Acid Microspheres that are Embedded in Edible Taste Strips, Poster Presentation, Apr. 2016, 1 page.

AChemS, Bitter Busters for Improving Taste of Childhood Medications, press release, Apr. 2016, 1 page.

Bala et al., Orally dissolving strips: A new approach to oral drug delivery system, 2013, Int. J. Parm. Investig. 3(2):67-76.

Guo et al., Microstructural investigation using synchrotron radiation X-ray microtomography reveals taste-masking mechanism of acetaminophen microspheres, 2016, Int. J. Pharm. 499:47-57.

Rassu et al., Encapsulation and modified-release of thymol from oralmicroparticles as adjuvant or substitute to current medications, 2014, Phytomedicine 21:1627-1632.

Robson et al., An investigation into the release of cefuroxime axetil from taste-masked stearic acid microspheres Part 1: The influence of the dissolution medium on the drug release profile and the physical integrity of the microspheres, 1999, Int. J. Pharm. 190:183-92.

Smutzer, A test for measuring gustatory function, 2008, Laryngoscope. 118(8):1411-6.

Bartoshuck et al., Differences in Our Sensory Worlds: Invalid Comparisons With Labeled Scales, 2005, Curr. Dir. Phys. Sci., 14:122-25.

Smutzer and Stull, Chemosensory Properties of Stearic Acid, Stearic Acid: Synthesis, Properties and Applications 1-24 (Yunfeng Lin and Qiang Peng, eds) (2014).

* cited by examiner

MICROENCAPSULATION OF ACTIVE AGENTS

CROSS-REFERENCE TO RELATED APPLICATIONS

This application is a U.S. national phase application filed under 35 U.S.C. § 371 claiming benefit to PCT International Patent Application No. PCT/US2017/045244, filed on Aug. 3, 2017, which claims priority to U.S. Provisional Application No. 62/370,427, filed Aug. 3, 2016, each of which disclosures is incorporated herein by reference in its entirety.

BACKGROUND OF THE INVENTION

Many medications produce a bitter taste, and taste plays a critical role in the delivery of child medications. Young children are highly averse to bitter taste, and the poor palatability of many orally administered drugs can result in avoidance of drugs by children. Furthermore, young children, elderly individuals, and adults with xerosteromia, may have problems ingesting drugs in capsule or tablet form. A drug delivery system that minimizes, delays, or eliminates bitter taste is an important goal. One approach to alleviate the bitter taste of medicines is to minimize the bitter taste of a drug, and to develop delivery methods that do not use capsules or tablets.

Pesticides and herbicides are chemicals that are widely used to destroy insect pests, animal pests, or weeds. The volatilization of environmental pesticides and herbicides may result in the release of these chemicals in unintended areas, and may also result in the unintended exposure of these compounds to humans. In addition, pesticides (and herbicides) can kill both insect pests as well as insects that may be beneficial to the environment. Environmental pesticides and herbicides may remain in the environment long after their intended use, and cause additional harm. In addition, pesticides and herbicides exhibit widely variable toxicity levels, and occupational exposure levels may have variable effects on human health. The exposure to pesticides can cause a variety of adverse health effects that include irritation to the skin and eyes, disrupting the nervous system, shortness of breath, coughing and congestion, mimicking hormones that may cause reproductive problems, or possibly the onset of cancer. For example, human exposure to the pesticides rotenone and paraquat have been linked to the onset of Parkinson's Disease. The herbicide atrazine is also an endocrine disrupter that may negatively affect human development. In addition, these chemicals may affect groundwater quality in affected areas.

There is thus a need in the art for compositions and methods to improve the taste of compounds and compositions and methods to improve the safety of herbicides and pesticides. The present invention addresses these unmet needs in the art.

SUMMARY OF THE INVENTION

In one aspect, the invention provides a microsphere comprising a sweetener. In one embodiment, the microsphere comprises at least one material selected from the group consisting of a fatty acid, glycerol, esters or any combination thereof. In one embodiment, the microsphere comprises at least one of material selected from group consisting of stearic acid, elaidic acid, Carnauba wax (palm wax), and Compritol® 888 ATO. In one embodiment, the microsphere comprises stearic acid.

In one embodiment, wherein the microsphere further comprises a lipid or glycoside. In one embodiment, the lipid or glycoside is selected from the group consisting of linoleic acid, cocoa butter, coconut oil and *Quillaja* saponin.

In one embodiment, the sweetener is selected from the group consisting of an artificial sweetener, a sugar alcohol, and a natural sweetener. In one embodiment, the sweetener is sucralose.

In one aspect, the invention provides an edible material. In one embodiment, the edible material comprises at least one microsphere, wherein the microsphere comprises an encapsulated agent.

In one embodiment, the agent is selected from the group consisting of at a therapeutic agent, an imaging agent, a diagnostic agent, a contrast agent, and a labeling agent. In one embodiment, the therapeutic agent is selected from the group consisting of a protein, a peptide, a peptidomemetic, an antibody, a ribozyme, a small molecule chemical compound, a nucleic acid, a plasmid vector, and an antisense nucleic acid molecule.

In one embodiment, the edible material further comprises a microsphere comprising a sweetener. In one embodiment, the sweetener is selected from the group consisting of an artificial sweetener, a sugar alcohol, and a natural sweetener. In one embodiment, the sweetener is sucralose.

In one embodiment, the microsphere comprises at least one material selected from the group consisting of a fatty acid, glycerol, esters or any combination thereof. In one embodiment, the microsphere comprises at least one of material selected from group consisting of stearic acid, elaidic acid, Carnauba wax (palm wax), and Compritol® 888 ATO. In one embodiment, the microsphere comprises stearic acid.

In one embodiment, wherein the microsphere further comprises a lipid or glycoside. In one embodiment, the lipid or glycoside is selected from the group consisting of linoleic acid, cocoa butter, coconut oil and *Quillaja* saponin.

In one embodiment, the edible material is selected from the group consisting of an edible oral strip, a gummy candy, a hard candy, chocolate, sugar-free chocolate, ice cream, pudding, apple sauce, and yogurt.

In one aspect, the invention provides a method for encapsulating a sweetener. In one embodiment, the method comprises melting stearic acid and sweetener; mixing the stearic acid and sweetener with a buffer having a pH of about 4 to about 5; and collecting the microspheres encapsulating the sweetener, wherein the temperature is below the temperature at which the sweetener degrades. In one embodiment, the pH of the buffer is 4.15. In one embodiment, the temperature is about 1% to about 20% below the temperature at which the sweetener degrades.

In one aspect, the invention provides a microsphere encapsulating an active agent. In one embodiment, the microsphere comprises at least one material selected from the group consisting of a fatty acid, glycerol, esters or any combination thereof. In one embodiment, the microsphere comprises at least one of material selected from group consisting of stearic acid, elaidic acid, Carnauba wax (palm wax), and Compritol® 888 ATO. In one embodiment, the microsphere comprises stearic acid.

In one embodiment, wherein the microsphere further comprises a lipid or glycoside. In one embodiment, the lipid or glycoside is selected from the group consisting of linoleic acid, cocoa butter, coconut oil and *Quillaja* saponin.

In one embodiment, the agent is selected from the group consisting of a pesticide, an irritant, a phytonutrient, and a sweetener. In one embodiment, the pesticide is selected from 2,4-dichlorophenoxyacetic acid (2,4-D) and Diuron (DCMU). In one embodiment, the agent is a pesticide and the microsphere further comprises an attractant. In one embodiment, the irritant is selected from the group consisting of capsaicin and dihydrocapsaicin.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

DETAILED DESCRIPTION

Figure 1:
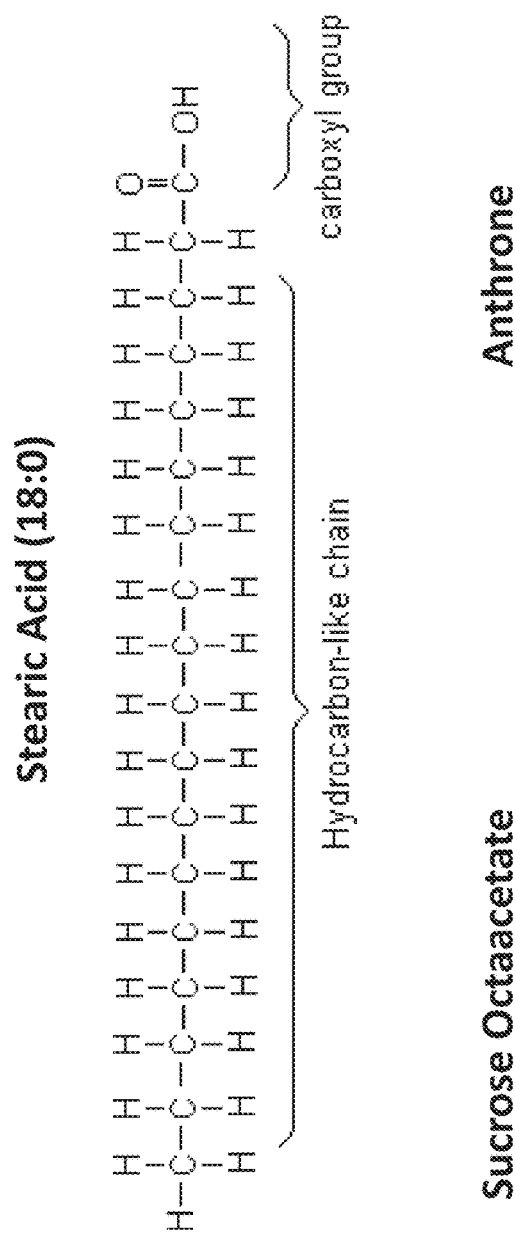
FIG. 1 depicts the chemical structures of stearic acid (18:0), sucrose octaacetate (SOA), and anthrone for carbohydrate assay.
Figure 1:
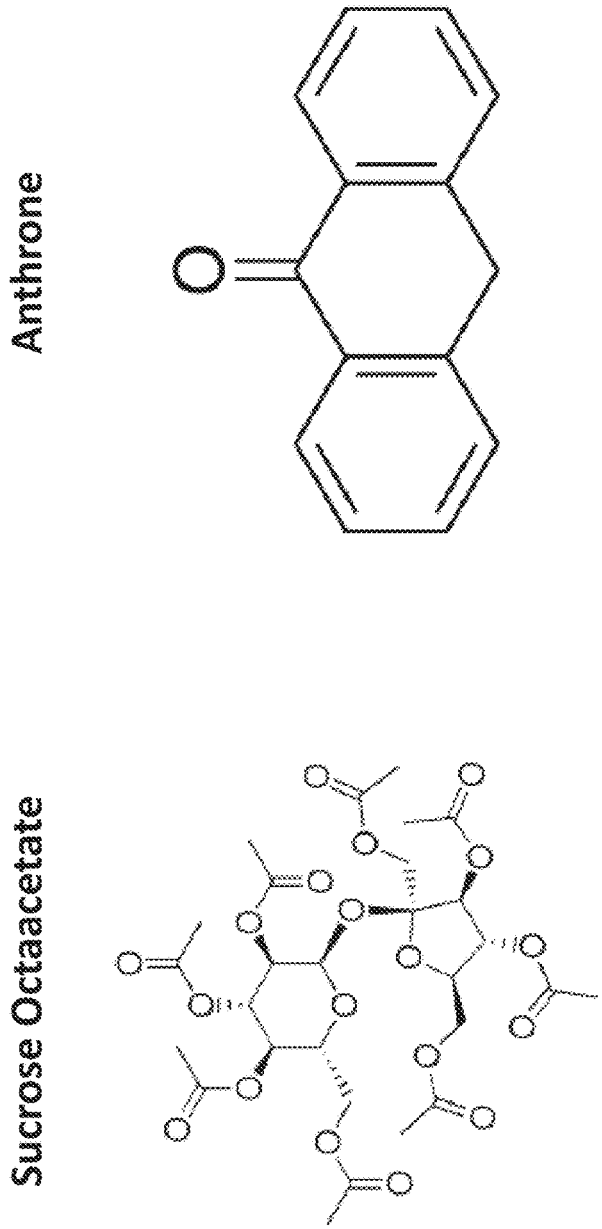

The present invention relates generally to compositions and methods for delivery of a therapeutic agent. In certain aspects, the compositions and methods relate to the delivery of a therapeutic agent, wherein the taste of the therapeutic agent is masked. In one embodiment, the therapeutic agent is incorporated into a microsphere.

The invention is based, in part on the unexpected finding that sweeteners can be encapsulated in a lipid microsphere. Accordingly, in one embodiment, the invention is a microsphere encapsulating a sweetener. In one embodiment, the microsphere comprises at least one of stearic acid, elaidic acid, Carnauba wax (palm wax), or Compritol® 888 ATO. In one embodiment, the microsphere further comprises a lipid or glycoside.

In one embodiment, the invention is a microsphere encapsulating a therapeutic agent. In one embodiment, the microsphere is a lipid microsphere. In one embodiment, the therapeutic agent has a bitter taste. In one embodiment, the microsphere comprises at least one of stearic acid, elaidic acid, Carnauba wax (palm wax), or Compritol® 888 ATO. In one embodiment, the microsphere masks the bitter taste of the therapeutic agent.

The invention is also based in part on the finding that microspheres can be incorporated into an edible material. Accordingly, the invention provides an edible material comprising at least one microsphere. In one embodiment, the at least one microsphere comprises a therapeutic agent. In one embodiment, the microsphere comprises at least one of stearic acid, elaidic acid, Carnauba wax, or Compritol® 888 ATO. In a one embodiment, the edible material comprises a second microsphere. In one embodiment, the second microsphere comprises a sweetener. In one embodiment, the edible material is a rapidly dissolving edible material. In one embodiment, the edible material is an edible oral strip, a gelatin candy, a hard candy, chocolate, ice cream, pudding, apple sauce, yogurt or other suitable food.

The invention also provides a method for masking the taste of a therapeutic agent. In one embodiment, the method comprises administering to a subject an effective amount of a microsphere comprising a therapeutic agent, wherein the microsphere masks the taste of the therapeutic agent. In one embodiment, the method comprises administering to a subject an effective amount of an edible material comprising a microsphere comprising a therapeutic agent. In one embodiment, the method comprises administering to a subject an effective amount of an edible material comprising a microsphere comprising a therapeutic agent and a microsphere comprising a sweetener. The invention also provides a method of encapsulating a sweetener. In one embodiment, the method comprises melting stearic acid and sweetener at a temperature of just below the temperature at which the sweetener degrades; mixing the stearic acid and sweetener with a buffer at about pH 4.15 and collecting the microspheres. In one embodiment, the temperature of just below the temperature at which the sweetener degrades is 1%-20% below the temperature at which the sweetener degrades. The invention is based, in part on the unexpected finding that herbicides and pesticides can be encapsulated in a microsphere. Accordingly, in one embodiment, the invention provides a microsphere and herbicide or pesticide. In one embodiment, the microsphere comprises a surface agent. In one embodiment, the surface agent is an insect attractant. In one embodiment, the invention also provides a method for improving the safety, decreasing the volatility of and/or increase the stability of an herbicide or a pesticide. In one embodiment, the method comprises encapsulating the herbicide or pesticide in a microsphere. In one embodiment, the microsphere is a stearic acid microsphere.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, a "disease" is a state of health of an animal wherein the animal cannot maintain homeostasis, and wherein if the disease is not ameliorated then the animal's health continues to deteriorate.

As used herein, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein with respect to the compositions of the invention, "biologically active" means that the compositions elicit a biological response in a mammal that can be monitored and characterized in comparison with an untreated mammal.

As used herein the term "microspheres" refers to nominally spherical particles having an average particle size of from about 1 to 999 microns.

As used herein, the term "treating" means ameliorating the effects of, or delaying, halting or reversing the progress of a disease or disorder. The word encompasses reducing the severity of a symptom of a disease or disorder and/or the frequency of a symptom of a disease or disorder.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease. Disease and disorder are used interchangeably herein.

As used herein, the terms "effective amount" or "therapeutically effective amount" or "pharmaceutically effective amount" of a composition are used interchangeably to refer to the amount of the composition that is sufficient to provide a beneficial effect to the subject to which the composition is administered. The term to "treat," as used herein, means reducing the frequency with which symptoms are experienced by a patient or subject or administering a composition to reduce the severity with which symptoms are experienced. An appropriate therapeutic amount in any individual case may be determined by one of ordinary skill in the art using routine experimentation.

As used herein, an "instructional material" includes a publication, a recording, a diagram, or any other medium of expression which can be used to communicate the usefulness of a compound, composition, vector, or delivery system of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound, composition, vector, or delivery system of the invention or be shipped together with a container which contains the identified compound, composition, vector, or delivery system. Alternatively, the instructional material can be shipped separately from the container with the intention that the instructional material and the compound be used cooperatively by the recipient. The term "microarray" refers broadly to both "DNA microarrays" and "DNA chip(s)," and encompasses all art-recognized solid supports, and all art-recognized methods for affixing nucleic acid molecules thereto or for synthesis of nucleic acids thereon.

By the term "specifically bind" or "specifically binds," as used herein, is meant that a first molecule (e.g., an antibody) preferentially binds to a second molecule (e.g., a particular antigenic epitope), but does not necessarily bind only to that second molecule.

The phrase "therapeutically effective amount," as used herein, refers to an amount that is sufficient or effective to prevent or treat (delay or prevent the onset of, prevent the progression of, inhibit, decrease or reverse) a disease or condition, including alleviating symptoms of diseases.

As used herein, a "therapeutic" treatment is a treatment administered to a subject who exhibits signs of pathology of a disease or disorder for the purpose of diminishing or eliminating those signs.

As used herein, a "pesticide" is a chemical or biological agent that, through its effect, deters, incapacitates, kills or otherwise discourages pests. Target pests can include insects, plant pathogens, weeds, mollusks, birds, mammals, fish, nematodes (roundworms), and microbes that destroy property, cause nuisance, spread disease or are vectors for disease.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, a "pharmaceutically acceptable carrier" means a pharmaceutically acceptable material, composition or carrier, such as a liquid or solid filler, diluent, excipient, solvent or encapsulating material, involved in carrying or transporting a compound(s) of the present invention within or to the subject such that it can perform its intended function. Typically, such compounds are carried or transported from one organ, or portion of the body, to another organ, or portion of the body. Each carrier must be "acceptable" in the sense of being compatible with the other ingredients of the formulation, and not injurious to the patient. Some examples of materials that can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. As used herein "pharmaceutically acceptable carrier" also includes any and all coatings, antibacterial and antifungal agents, and absorption delaying agents, and the like that are compatible with the activity of the compound, and are physiologically acceptable to the subject. Supplementary active compounds can also be incorporated into the compositions.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof.

As used herein, the term "polymer" refers to a molecule composed of repeating structural units typically connected by covalent chemical bonds. The term "polymer" is also meant to include the terms copolymer and oligomers. In one embodiment, a polymer comprises a backbone (i.e., the chemical connectivity that defines the central chain of the polymer, including chemical linkages among the various polymerized monomeric units) and a side chain (i.e., the chemical connectivity that extends away from the backbone).

As used herein, the term "subject" refers to a human or another mammal (e.g., primate, dog, cat, goat, horse, pig, mouse, rat, rabbit, and the like). In many embodiments of the present invention, the subject is a human being. In such embodiments, the subject is often referred to as an "individual" or a "patient." The terms "individual" and "patient" do not denote a particular age.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention is partly based upon the surprising discovery that microspheres encapsulating a therapeutic agent and edible compositions comprising the microspheres can mask the unpleasant or bitter taste of the therapeutic agent. This novel approach of encapsulating a therapeutic agent in microspheres to mask the taste of the therapeutic agent and further masking the bitter taste of the encapsulated therapeutic agent by incorporating it into an edible material (e.g. a film) that also contains masking agents, is a novel method for delivering bitter tasting drugs to young children, adults, and elderly individuals. The bitter taste of the therapeutic agent is minimized or completely eliminated when delivered using the compositions of the present invention. As opposed to tablets, small microspheres are not broken up by chewing, but readily release their contents in the oral cavity.

The present invention is also partly based upon the surprising discovery that sweeteners can be incorporated into microspheres. Accordingly, the invention provides a microsphere comprising a sweetener. In one embodiment, the sweetener is a non-caloric sweetener. In one embodiment, the sweetener is an artificial sweetener, a sugar alcohol, or a natural sweetener.

In one embodiment, the microsphere comprises a fatty acid, glycerol, esters or any combination thereof. In one embodiment, the microsphere comprises at least one of stearic acid, elaidic acid, Carnauba wax (palm wax), or Compritol® 888 ATO. In one embodiment, the microsphere comprises stearic acid. Stearic acid is an excellent molecule for encapsulating molecules because stearic acid has no taste.

In one embodiment, the microsphere further comprises a lipid or glycoside. In one embodiment, the lipid or glycoside decreases the melting point of the microsphere. In one embodiment, the lipid or glycoside includes, but is not limited to, linoleic acid, linolenic acid, oleic acid, palmitic acid, myristic acid, cocoa butter, coconut oil, and *Quillaja* saponin.

The ratio of the fatty acid, glycerol, or ester to lipid or glycoside is not particularly limited. In one embodiment, the ratio of the fatty acid, glycerol, or ester to lipid or glycoside is in the range of about 50,000:1 to about 10:1. In one embodiment, the ratio of the fatty acid, glycerol, or ester to lipid or glycoside is about 22,000:1. In one embodiment, the ratio of the fatty acid, glycerol, or ester to lipid or glycoside is about 67:1. In one embodiment, the ratio of the fatty acid, glycerol, or ester to lipid or glycoside is about 15:1. In one embodiment, the ratio of the fatty acid, glycerol, or ester to lipid or glycoside is about 10:1. In one embodiment, the ratio of the fatty acid, glycerol, or ester to lipid or glycoside can be adjusted to control the microsphere melting point. In one embodiment, the ratio of the fatty acid, glycerol, or ester to lipid or glycoside can be adjusted to decrease the microsphere melting point.

In one embodiment, the microsphere comprises stearic acid. In one embodiment, the microsphere comprises stearic acid and linoleic acid. In one embodiment, the microsphere comprises about 22,000:1 stearic acid to linoleic acid. In one embodiment, the microsphere comprises stearic acid and cocoa butter. In one embodiment, the microsphere comprises about 10:1 stearic acid to cocoa butter. In one embodiment, the microsphere comprises stearic acid and coconut oil. In one embodiment, the microsphere comprises about 15:1 stearic acid to coconut oil. In one embodiment, the microsphere comprises stearic acid and *Quillaja* saponin. In one embodiment, the microsphere comprises about 67:1 stearic acid to *Quillaja* saponin.

The present invention also provides an edible composition comprising at least one microsphere of the invention. In one embodiment, the edible composition comprises at least one microsphere encapsulating a therapeutic agent. The edible composition may comprise sweet taste stimuli including, but not limited to sucralose glycerol, mannitol, along with peppermint oil to further mask the taste of the therapeutic agent. In certain aspects, the release of the encapsulated therapeutic agent within microspheres is delayed by about 15 to 20 seconds after the edible composition is administered so that the near instantaneous release of sweet taste stimuli from rapidly dissolving edible material initially minimizes the bitter taste of therapeutic agent.

In one embodiment, the edible composition comprises at least one microsphere encapsulating a sweetener. In one embodiment, the edible composition comprises at least one microsphere encapsulating a sweetener and at least one microsphere encapsulating a therapeutic agent. Incorporation of microspheres containing a therapeutic agent and microspheres containing a sweetener provides further masks the taste of the therapeutic agent in the oral cavity because the delay in the release of the therapeutic agent from microspheres occurs simultaneously with the delayed release of sucralose from microspheres.

The invention also provides a method of encapsulating a sweetener into a microsphere. The sweetener may be incorporated into a microsphere by using a buffer at a low pH and by melting the sweetener at a temperature just above its melting point and below the temperature at which it degrades. For example, incorporation of a sweetener into stearic acid microspheres can be achieved at a pH of about 4 to about 4.5 because at this pH, the carboxyl group of stearic acid is fully protonated and neutral, allowing for the incorporation of polar compounds such as a sweetener. Accordingly, in one embodiment, the method comprises melting stearic acid and sweetener at a temperature of just below the temperature at which the sweetener degrades; mixing the stearic acid and sweetener with a buffer at pH of about 4.0 to about 4.25; and collecting the microspheres. In one embodiment, the temperature of just below the temperature at which the sweetener degrades is about 1%-20% below the temperature at which the sweetener degrades.

The invention also provides a method for masking the taste of a therapeutic agent. In one embodiment, the method comprises administering to a subject an effective amount of a microsphere comprising a therapeutic agent, wherein the microsphere masks the taste of the therapeutic agent. In one embodiment, the method comprises administering to a subject an effective amount of an edible material comprising a microsphere comprising a therapeutic agent. In one embodiment, the method comprises administering to a subject an effective amount of an edible material comprising a microsphere comprising a therapeutic agent and a microsphere comprising a sweetener.

Compositions

The present invention provides microspheres for encapsulating a material. In some embodiments, the microspheres encapsulate at least one agent and/or a sweetener. In one embodiment, the microspheres encapsulate at least one agent including, but not limited to, a therapeutic agent, an imaging agent, contrast agent, diagnostic agent, an active and a labeling agent. In one embodiment, the microspheres mask the taste of the agent.

In one embodiment, the microsphere comprises anionic, cationic, amphoteric, or non-ionic surfactants. Anionic surfactants include di-(2 ethylhexyl)sodium sulfosuccinate; non-ionic surfactants include the fatty acids and the esters thereof; surfactants in the amphoteric group include (1) substances classified as simple, conjugated and derived proteins such as the albumins, gelatins, and glycoproteins, and (2) substances contained within the phospholipid classification, for example, lecithin. The amine salts and the quaternary ammonium salts within the cationic group also comprise useful surfactants. Other surfactant compounds useful to form coacervates include polysaccharides and their derivatives, the mucopolysaccharides and the polysorbates and their derivatives. Synthetic polymers that may be used as surfactants include compositions such as polyethylene glycol and polypropylene glycol. Further examples of suitable compounds that may be utilized to prepare coacervate systems include glycoproteins, glycolipids, galactose, gelatins, modified fluid gelatins and galacturonic acid. In one embodiment, the microsphere comprises a fatty acid, a polymer, glycerol, esters or any combination thereof.

Examples of fatty acids include, but are not limited to, butyric acid, valeric acid, caproic acid, enanthic acid, caprylic acid, pelargonic acid, caprylic acid, undecylic acid, lauric acid, tridecylic acid, myristic acid, pentadecylic acid, palmitic acid, heptadecylic acid, stearic acid, nonadecanoic acid, arachic acid, isocrotonic acid, undecylenic acid, oleic acid, elaidic acid, sorbic acid, linoleic acid, linolenic acid and arachidonic acid.

The microspheres of the invention can be made by any method conventional in the art. For example, the microspheres can be made through methods such as spray drying method, freeze-drying method, interface polymerization, hot-melt encapsulation, emulsion, microencapsulation with solvent evaporation, coacervation, microfluidity using a porous membrane, and the like, can be used. In one embodiment, the microspheres are produced using the hot-melt encapsulation method. Skilled artisans can understand that many modifications can be done to these methods to obtain loaded microspheres.

In one embodiment, the microsphere comprises at least one of stearic acid, elaidic acid, Carnauba wax (palm wax), paraffin wax, ceresin wax, or Compritol® 888 ATO. In one embodiment, the microsphere comprises stearic acid.

In one embodiment, the microspheres encapsulate at least one herbicide or pesticide. In one embodiment, the microsphere improves the safety, increases stability and/or decrease the volatility of the at least one pesticide. In one embodiment, the pesticide includes, but is not limited to, herbicides, fungicides, insecticides and bactericides. In one embodiment, the pesticide is 2,4-dichlorophenoxyacetic acid (2,4-D). In one embodiment, the herbicide is Diuron (DCMU).

In one embodiment, the insecticide includes, but is not limited to, labamectin, acephate, acetamiprid, acethion, acetoprole, acrinathrin, acrylonitrile, alanycarb, aldicarb, aldoxycarb, aldrin, allethrin, allosamidin, allyxycarb, alpha-cypermethrin, alpha-endosulfan, amidithion, aminocarb, amiton, amitraz, anabasine, athidathion, azadirachtin, azamethiphos, azinphos-ethyl, azinphos-methyl, azothoate, barium hexafluorosilicate, barthrin, bendiocarb, benfuracarb, bensultap, beta-cyfluthrin, beta-cypermethrin, bifenthrin, bioallethrin, bioethanomethrin, biopermethrin, bioresmethrin, bistrifluron, borax, boric acid, boric acid, bromfenvinfos, bromocyclen, bromo-DDT, bromophos, bromophos-ethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, chlorantraniliprole, chlorbicyclen, chlordane, chlordecone, chlordimeform, chlorethoxyfos, chlorfenapyr, chlorfenvinphos, chlorfluazuron, chlormephos, chloroform, chloropicrin, chlorphoxim, chlorprazophos, chlorpyrifos, chlorpyrifos-methyl, chlorthiophos, chromafenozide, cinerin I, cinerin II, cismethrin, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyclethrin, cycloprothrin, cyfluthrin, cyhalothrin, cypermethrin, cyphenothrin, cyromazine, cythioate, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diatomaceous earth, diazinon, dicapthon, dichlofenthion, dichlorvos, dicresyl, dicrotophos, dicyclanil, dieldrin, diflubenzuron, dilor, dimefluthrin, dimefox, dimetan, dimethoate, dimethrin, dimethylvinphos, dimetilan, dinex, dinoprop, dinosam, dinotefuran, diofenolan, dioxabenzofos, dioxacarb, dioxathion, dioxin, disulfoton, dithicrofos, d-limonene, DNOC, doramectin, ecdysterone, emamectin, EMPC, empenthrin, endosulfan, endothion, endrin, EPN, epofenonane, eprinomectin, esfenvalerate, etaphos, ethiofencarb, ethion, ethiprole, ethoate-methyl, ethoprophos, ethyl formate, ethyl-DDD, ethylene dichloride, ethylene oxide, etofenprox, etrimfos, EXD, famphur, fenamiphos, fenazaflor, fenchlorphos, fenethacarb, fenfluthrin, fenitrothion, fenobucarb, fenoxacrim, fenoxycarb, fenpirithrin, fenpropathrin, fensulfothion, fenthion, fenthion-ethyl, fenvalerate, fipronil, flonicamid, flubendiamide, flucofuron, flucycloxuron, flucythrinate, flufenerim, flufenoxuron, flufenprox, fluvalinate, fonofos, formetanate, formothion, formparanate, fosmethilan, fospirate, fosthietan, furathiocarb, furethrin, gamma-cyhalothrin, gamma-HCH, halfenprox, halofenozide, HCH, HEOD, heptachlor, heptenophos, heterophos, hexaflumuron, HHDN, hydramethylnon, hydrogen cyanide, hydroprene, hyquincarb, imidacloprid, imiprothrin, indoxacarb, iodomethane, IPSP, isazofos, isobenzan, isocarbophos, isodrin, isofenphos, isoprocarb, isoprothiolane, isothioate, isoxathion, ivermectin, jasmolin I, jasmolin II, jodfenphos, juvenile hormone 1, juvenile hormone II, juvenile hormone III, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, mephosfolan, mercurous chloride, mesulfenfos, metaflumizone, methacrifos, methamidophos, methidathion, methiocarb, methocrotophos, methomyl, methoprene, methoxychlor, methoxyfenozide, methylchloroform, methylene chloride, metofluthrin, metolcarb, metoxadiazone, mevinphos, mexacarbate, milbemectin, milbemycin oxime, mipafox, mirex, monocrotophos, morphothion, moxidectin, naftalofos, naled, naphthalene, nicotine, nifluridide, nitenpyram, nithiazine, nitrilacarb, novaluron, noviflumuron, omethoate, oxamyl, oxydemeton-methyl, oxydeprofos, oxydisulfoton, para-dichlorobenzene, parathion, parathion-methyl, penfluron, pentachlorophenol, permethrin, phenkapton, phenothrin, phenthoate, phorate, phosalone, phosfolan, phosmet, phosnichlor, phosphamidon, phosphine, phoxim, phoxim-methyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, profenofos, profluthrin, promacyl, promecarb, propaphos, propetamphos, propoxur, prothidathion, prothiofos, prothoate, protrifenbute, pyraclofos, pyrafluprole, pyrazophos, pyresmethrin, pyrethrin I, pyrethrin II, pyridaben, pyridalyl, pyridaphenthion, pyrifluquinazon, pyrimidifen, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sophamide, spinetoram, spinosad, spiromesifen, spirotetramat, sulcofuron, sulfluramid, sulfotep, sulfuryl fluoride, sulprofos, tau-fluvalinate, tazimcarb, TDE, tebufenozide, tebufenpyrad, tebupirimfos, tefluben-zuron, tefluthrin, temephos, TEPP, terallethrin, terbufos, tetrachloroethane, tetrachlorvinphos, tetramethrin, theta-cypermethrin, thiacloprid, thiamethoxam, thicrofos, thiocarboxime, thiocyclam, thiodicarb, thiofanox, thiometon, thiosultap, thuringiensin, tolfenpyrad, tralomethrin, transfluthrin, transpermethrin, triarathene, triazamate, triazophos, trichlorfon, trichlormetaphos-3, trichloronat, trifenofos, triflumuron, trimethacarb, triprene, vamidothion, vaniliprole, XMC, xylylcarb, zeta-cypermethrin, zolaprofos, and α-ecdysone.

In one embodiment, the herbicide includes, but is not limited to, acetyl CoA carboxylase (ACCase) inhibitors, enolpyruvyl shikimate-3-phosphate synthase (EPSPS) inhibitors, glutamine synthetase inhibitors, auxins, photosystem I (PS I) inhibitors, photosystem II (PS II) inhibitors, acetolactate synthase (ALS) or acetohydroxy acid synthase (AHAS) inhibitors, mitosis inhibitors, protoporphyrinogen oxidase (PPO) inhibitors, cellulose inhibitors, oxidative phosphorylation uncouplers, dihydropteroate synthase inhibitors, fatty acid and lipid biosynthesis inhibitors, auxin transport inhibitors and carotenoid biosynthesis inhibitors, salts and esters thereof, racemic mixtures and resolved isomers thereof, and mixtures thereof.

A non-limiting example of a PSPS herbicide includes glyphosate or a salt or ester thereof.

Exemplary glutamine synthetase herbicides include glufosinate or glufosinate-P, or a salt or and ester thereof.

Exemplary ACCase inhibitors include, but are not limited to, alloxydim, butroxydim, clethodim, cycloxydim, pinoxaden, sethoxydim, tepraloxydim and tralkoxydim, salts and esters thereof, and mixtures thereof. Another group of ACCase inhibitors include chlorazifop, clodinafop, clofop, cyhalofop, diclofop, diclofop-methyl, fenoxaprop, fenthiaprop, fluazifop, haloxyfop, isoxapyrifop, metamifop, propaquizafop, quizalofop and trifop, salts and esters thereof, and mixtures thereof.

Exemplary auxin herbicides (i.e., synthetic auxin herbicides) include, but are not limited to, 2,4-dichlorophenoxyacetic acid (2,4-D), 4-(2,4-dichlorophenoxy)butyric acid (2,4-DB), dichloroprop, 2-methyl-4-chlorophenoxy acetic acid (MCPA), 4-(4-chloro-2-methylphenoxy)butanoic acid (MCPB), aminopyralid, clopyralid, fluroxypyr, triclopyr, diclopyr, mecoprop, dicamba, picloram and quinclorac, salts and esters thereof, and mixtures thereof.

Exemplary PS II inhibitors include, but are not limited to, ametryn, amicarbazone, atrazine, bentazon, bromacil, bromoxynil, chlorotoluron, cyanazine, desmedipham, desmetryn, dimefuron, Diuron (DCMU), fluometuron, hexazinone, ioxynil, isoproturon, linuron, metamitron, methibenzuron, metoxuron, metribuzin, monolinuron, phenmedipham, prometon, prometryn, propanil, pyrazon, pyridate, siduron, simazine, simetryn, tebuthiuron, terbacil, terbumeton, terbuthylazine and trietazine, salts and esters thereof, and mixtures thereof.

Exemplary ALS and AHAS inhibitors include, but are not limited to, amidosulfuron, azimsulfruon, bensulfuron-methyl, bispyribac-sodium, chlorimuron-ethyl, chlorsulfuron, cinosulfuron, cloransulam-methyl, cyclosulfamuron, diclosulam, ethametsulfuron-methyl, ethoxysulfuron, flazasulfuron, florazulam, flucarbazone, flucetosulfuron, flumetsulam, flupyrsulfuron-methyl, foramsulfuron, halosulfuron-methyl, imazamethabenz, imazamox, imazapic, imazapyr, imazaquin, imazethapyr, imazosulfuron, iodosulfuron, metsulfuron-methyl, nicosulfuron, penoxsulam, primisulfuron-methyl, propoxycarbazone-sodium, prosulfuron, pyrazosulfuron-ethyl, pyribenzoxim, pyrithiobac, rimsulfuron, sulfometuron-methyl, sulfosulfuron, thiencarbazone, thifensulfuron-methyl, triasulfuron, tribenuron-methyl, triflox-ysulfuron and triflusulfuron-methyl, salts and esters thereof, and mixtures thereof.

Exemplary mitosis inhibitors include, but are not limited to, anilofos, benefin, DCPA, dithiopyr, ethalfluralin, flufenacet, mefenacet, oryzalin, pendimethalin, thiazopyr and trifluralin, salts and esters thereof, and mixtures thereof.

Exemplary PPO inhibitors include, but are not limited to, acifluorfen, azafenidin, bifenox, butafenacil, carfentrazone-ethyl, flufenpyr-ethyl, flumiclorac, flumiclorac-pentyl, flumioxazin, fluoroglycofen, fluthiacet-methyl, fomesafen, lactofen, oxadiargyl, oxadiazon, oxyfluorfen, pyraflufen-ethyl, saflufenacil and sulfentrazone, salts and esters thereof, and mixtures thereof.

Exemplary carotenoid biosynthesis inhibitors include, but are not limited to, aclonifen, amitrole, beflubutamid, benzofenap, clomazone, diflufenican, fluridone, flurochloridone, flurtamone, isoxaflutole, mesotrione, norflurazon, picolinafen, pyrazolynate, pyrazoxyfen, sulcotrione, tembotrione and topramezone, salts and esters thereof, and mixtures thereof.

Exemplary PS I inhibitors include, but are not limited to, diquat and paraquat, salts and esters thereof, and mixtures thereof.

Exemplary cellulose inhibitors include, but are not limited to, dichlobenil and isoxaben.

Non-limiting examples of an oxidative phosphorylation uncoupler include dinoterb, esters thereof, and the neurotoxin 1-methyl-4-phenyl-1,2,3,6-tetrahydropyridine (MPTP).

Exemplary mitochondrial electron transport inhibitors include, but are not limited to, rotenone, hydrogen cyanide, and amytal.

Exemplary auxin transport inhibitors include, but are not limited to, diflufenzopyr and naptalam, salts and esters thereof, and mixtures thereof.

A non-limiting example of a dihydropteroate synthase inhibitor is asulam and salts thereof.

Exemplary fatty acid and lipid biosynthesis inhibitors include, but are not limited to, bensulide, butylate, cycloate, EPTC, esprocarb, molinate, pebulate, prosulfocarb, thiobencarb, triallate and vemolate, salts and esters thereof, and mixtures thereof.

The present invention also provides microspheres comprising a surface agent. In some embodiments, the surface agent is an attractant. In one embodiment, the attractant enhances pest consumption.

An attractant, as used herein, includes any attractant, such as a chemical attractant. These may include food odor attractants, aggregation attractants, or insect pheromone-related attractants. For example, an aggregation (or pheromone-related) attractant in includes, but is not limited to, n-hexanoic acid. Other attractants includes, but is not limited to, aliphatic food odor attractants, for example, (Z,Z,E)-3, 6,8-dodecatien-1-ol, or aromatic food odor attractants, such as 4-hydroxybenzoic acid. Other aliphatic and aromatic food odor attractants are known, and the attractants disclosed in U.S. Pat. No. 5,756,114 are herein incorporated by reference in its entirety and may serve as attractants in accordance with various embodiments of the present disclosure. The attractants disclosed in U.S. Pat. No. 6,352,703 are also incorporated by reference in its entirety.

In one embodiment, the invention provides microspheres comprising a phytonutrient. In one embodiment, the phytonutrient includes, but is not limited to, carotenoids (antioxidants), lycopene, lutein, melatonin, and zeaxanthin (eye health), ellagic acid, flavonoids, flavinols, resveratrol (heart health), glucosinolates, and phytoestrogens.

In one embodiment, the invention provides a microsphere comprising an irritant. Exemplary irritant include, but are not limited to, anthralin, camphor, canthariden, capsaicin, dihydrocapsacin, *capsicum*, Oleoresin *Capsicum*, coal tar, ichthammol, juniper tar, menthol, Peruvian balsam, pine tar, aluminum chloride, resorcinol, storax, tolu balsam, nitric acid, phenol, podofilox, *podophyllum*, potassium hydroxide, silver nitrate, trichloroacetic acid, benzoyl peroxide, fluorouracil, salicylic acid, retinoic acid, ethanol, isopropanol, selenium sulfide, benzalkonium chloride, allantoin, aminobenzoic acid, propenoic acid, dihydroxyacetone, dioxybenzone, octyl methoxycinnamate, 2,4,6,8-nonanetetraenoic acid, homosalate, hydrogen peroxide, hydroxyurea, citric acid, lactic acid, glycolic acid, salicylic acid, pyromellitic acid, pyromellitic dianhydride, pyruvic acid, acetic acid, acrylic acid, trichloroacetic acid, 1-pyrrolidone-5-carboxylic acid, capryloyl salicylic acid, hydroxy decanoic acid, hydroxy octanoic acid, gluconolactone, methoxypropyl gluconamide, malic acid, maleic acid, tartaric acid, mandelic acid, gluconic acid, sodium chloride, ethylenediaminetetraacetic acid disodium salt, sodium boroformate, sodium bicarbonate, and dipropyl ketone. In one embodiment, the irritant is capsaicin or dihydrocapsacin.

In one embodiment, the invention provides a microsphere comprising an odorant. In one embodiment, the odorant is a fragrant. For example, exemplary fragrants include, but are not limited to C-18, anisic aldehyde, coumarin, ethyl maltol, ethyl vanillin, oxyphenylon, Vanillin USP, benzyl benzoate, Tonka Bean, Cinnamic Aldehyde, Euganol, Orange Oil, Pine Oil, Aldehyde C-12, Cedarwood Va., Indol, Castoreum and *Eucalyptus* Oil. In one embodiment, a composition comprising a microsphere comprising an odorant is an air-freshener.

In one embodiment, the invention provides a microsphere comprising a pest control agent. For example, in one embodiment, the pest control agent is a rodenticide, insect bait, insecticide.

For example, in one embodiment, the insecticide is a moth control agent, an ant control agent or a cockroach control agent. Insecticides include, but are not limited to, Fipronil, avermectin, p-dichlorobenzene and naphthalene.

In one embodiment, the rodenticides include, but are not limited to, ANTU, arsenic trioxide, barium carbonate, chloralose, crimidine, 1,3-difluoro-2-propanol, endrin, fluoroacetamide, phosacetim, white phosphorus, pyrinuron, scilliroside, oleandrin, digoxin, sodium fluoroacetate, strychnine, tetramethylenedisulfotetramine, thallium sulfate, nitrophenols, Zyklon B, calciferols (vitamins D), cholecalciferol (vitamin D3), ergocalciferol (vitamin D2), aluminium phosphide, calcium phosphide, magnesium phosphide, zinc phosphide, warfarin, coumatetralyl, difenacoum, brodifacoum, flocoumafen, bromadiolone, diphacinone, chlorophacinone, pindone, Difethialonem, and sulfaquinoxaline. In one embodiment, the microsphere encapsulating a rodenticide is embedded in peanut butter.

In one embodiment, the invention provides microspheres comprising a sweetener. In one embodiment, the sweetener is an artificial sweetener, a sugar alcohol, or a natural sweetener. In one embodiment, the sweetener includes, but is not limited to, acesulfame potassium, advantame, alitame, aspartame, aspartame-acesulfame salt, sodium cyclamate, glucin, neohesperidin dihydrochalcone, neotame, Rebaudioside A, saccharin, sucralose, sucrose, glucose, fructose, galactose, ribulose, erythritol, hydrogenated starch hydrolysate, isomalt, lactitol, maltitol, mannitol, sorbitol, xylitol, trehalose, tagatose, brazzein, curculin, glycyrrhizin, inulin, mogroside, mabinlin, malto-oligosaccharaide, miraculin, monatin, monellin, osladin, pentadin, thaumatin, steviosides, or any combination thereof.

In one embodiment, the microsphere comprises at least one imaging agent. Imaging agents are materials that allow the microsphere to be visualized after exposure to a cell or tissue. Visualization includes imaging for the naked eye, as well as imaging that requires detecting with instruments or detecting information not normally visible to the eye, and includes imaging that requires detecting of photons, sound or other energy quanta. Examples include stains, vital dyes, fluorescent markers, radioactive markers, enzymes or plasmid constructs encoding markers or enzymes. Many materials and methods for imaging and targeting that may be used in microspheres are provided in the Handbook of Targeted delivery of Imaging Agents, Torchilin, ed. (1995) CRC Press, Boca Raton, Fla.

Visualization based on molecular imaging typically involves detecting biological processes or biological molecules at a tissue, cell, or molecular level. Molecular imaging can be used to assess specific targets for gene therapies, cell-based therapies, and to visualize pathological conditions as a diagnostic or research tool. Imaging agents that are able to be delivered intracellularly are particularly useful because such agents can be used to assess intracellular activities or conditions. Imaging agents must reach their targets to be effective; thus, in some embodiments, an efficient uptake by cells is desirable. A rapid uptake may also be desirable to avoid the reticuloendothelial system (RES), see review in Allport and Weissleder, Experimental Hematology 1237-1246 (2001).

Further, imaging agents preferably should provide high signal to noise ratios so that they may be detected in small quantities, whether directly, or by effective amplification techniques that increase the signal associated with a particular target. Amplification strategies are reviewed in Allport and Weissleder, Experimental Hematology 1237-1246 (2001), and include, for example, avidin-biotin binding systems, trapping of converted ligands, probes that change physical behavior after being bound by a target, and taking advantage of relaxation rates. Examples of imaging technologies include magnetic resonance imaging, radionuclide imaging, computed tomography, ultrasound, and optical imaging.

Microspheres as set forth herein may advantageously be used in various imaging technologies or strategies, for example by incorporating imaging agents into microspheres. Many imaging techniques and strategies are known, e.g., see review in Allport and Weissleder, Experimental Hematology 1237-1246 (2001); such strategies may be adapted to use with microspheres. Suitable imaging agents include, for example, fluorescent molecules, DNA stains, labeled antibodies, labeled avidin:biotin binding agents, colloidal metals (e.g., gold, silver), reporter enzymes (e.g., horseradish peroxidase), superparamagnetic transferrin, second reporter systems (e.g., tyrosinase), paramagnetic chelates, Rhodamine, and ethidium bromide, propidium iodide.

In one embodiment, the imaging agent inhibits oxidation or photo-oxidation.

Compared to imaging agents that are merely conjugated to a targeting molecule, microspheres can increase signal-to-noise ratio by delivering larger imaging agent loads per uptake event resulting in higher amplification. Many imaging agents may be loaded into a microsphere having a targeting molecule (e.g., tenascin), which passes into a cell via a single uptake event. In contrast, only a single imaging agent linked to a targeting molecule would be taken up by the same event. Since the internalization, intracellular transport, and recycling of cell surface receptors often requires significant turnaround time, the resultant direct uptake of signal molecules by a cell is slower than the uptake of signal molecules with a microsphere.

In some embodiments, the imaging agent is a magnetic resonance imaging contrast agent. Examples of Magnetic resonance imaging contrast agents include, but are not limited to, 1,4,7,10-tetraazacyclododecane-N,N',N'',N'''-tetraacetic acid (DOTA), diethylenetriaminepentaacetic (DTPA), 1,4,7,10-tetraazacyclododecane-N,N',N'',N'''-tetraethylphosphorus (DOTEP), 1,4,7,10-tetraazacyclododecane-N,N',N''-triacetic acid (DOTA) and derivatives thereof (see U.S. Pat. Nos. 5,188,816, 5,219,553, and 5,358,704). In some embodiments, the imaging agent is an X-Ray contrast agent. X-ray contrast agents already known in the art include a number of halogenated derivatives, especially iodinated derivatives, of 5-amino-isophthalic acid.

Clinical imaging is of increasing helpfulness in clinical and research settings, e.g., as reviewed by Acharya et al., Computerized Medical Imaging and Graphics, 19(1): 3-25 (1995). Current uses include laboratory medicine, surgery, radiation therapy, nuclear medicine, and diagnostic radiology. Microspheres may be loaded with agents that enhance these processes, for example by enhancing contrast, or delivering agents to cells that allow for visualization with such techniques.

In one embodiment, the microsphere comprises at least one therapeutic agent. In one embodiment, the therapeutic agent is a small molecule, a nucleic acid, a polypeptide, or an antibody, a siRNA, a ribozyme, an antisense nucleic acid, an antagonist, an aptamer, a peptidomimetic, or any combination thereof.

In one embodiment, the microsphere comprises a targeting domain that directs the microsphere to a site. In one embodiment, the site is a site in need of the agent comprised within the microsphere. The targeting domain may comprise a nucleic acid, peptide, antibody, small molecule, organic molecule, inorganic molecule, and the like that targets the particle to a site in particular need of the therapeutic agent. In certain embodiments, the particle comprises multivalent targeting, wherein the particle comprises multiple targeting mechanisms described herein. In certain embodiments, the targeting domain of the microsphere specifically binds to a target associated with a site in need of an agent comprised within the microsphere. For example, the targeting domain may be chosen to recognize a ligand that acts as a cell surface marker on target cells associated with a particular disease state. Such a target can be a protein, protein fragment, antigen, or other biomolecule that is associated with the targeted site. In certain embodiments, the target (e.g. antigen) associated with a site in need of a treatment with an agent.

Small Molecule Therapeutic Agents

In various embodiments, the therapeutic agent is a small molecule. When the therapeutic agent is a small molecule, a small molecule may be obtained using standard methods known to the skilled artisan. Such methods include chemical organic synthesis or biological means. Biological means include purification from a biological source, recombinant synthesis and in vitro translation systems, using methods well known in the art. In one embodiment, a small molecule therapeutic agent comprises an organic molecule, inorganic molecule, biomolecule, synthetic molecule, and the like.

In one embodiment, the small molecule therapeutic agent includes, but is not limited to a vitamin, tetrahydrocannabinol (THC), an anti-nausea drug, anti-parasitic, SSRIs, an antibiotic, and an antiviral.

Exemplary anti-nausea drugs include, but are not limited to, cinnarizine, cyclizine, and promethazine.

Exemplary anti-parasitics include, but are not limited to, ivermectin, paraquine and pyrantel.

Combinatorial libraries of molecularly diverse chemical compounds potentially useful in treating a variety of diseases and conditions are well known in the art as are method of making the libraries. The method may use a variety of techniques well-known to the skilled artisan including solid phase synthesis, solution methods, parallel synthesis of single compounds, synthesis of chemical mixtures, rigid core structures, flexible linear sequences, deconvolution strategies, tagging techniques, and generating unbiased molecular landscapes for lead discovery vs. biased structures for lead development.

In a general method for small library synthesis, an activated core molecule is condensed with a number of building blocks, resulting in a combinatorial library of covalently linked, core-building block ensembles. The shape and rigidity of the core determines the orientation of the building blocks in shape space. The libraries can be biased by changing the core, linkage, or building blocks to target a characterized biological structure ("focused libraries") or synthesized with less structural bias using flexible cores.

The small molecule and small molecule compounds described herein may be present as salts even if salts are not depicted and it is understood that the invention embraces all salts and solvates of the inhibitors depicted here, as well as the non-salt and non-solvate form of the inhibitors, as is well understood by the skilled artisan. In some embodiments, the salts of the inhibitors of the invention are pharmaceutically acceptable salts.

Where tautomeric forms may be present for any of the inhibitors described herein, each and every tautomeric form is intended to be included in the present invention, even though only one or some of the tautomeric forms may be explicitly depicted. For example, when a 2-hydroxypyridyl moiety is depicted, the corresponding 2-pyridone tautomer is also intended.

The invention also includes any or all of the stereochemical forms, including any enantiomeric or diasteriomeric forms of the inhibitors described. The recitation of the structure or name herein is intended to embrace all possible stereoisomers of inhibitors depicted. All forms of the inhibitors are also embraced by the invention, such as crystalline or non-crystalline forms of the inhibitors. Compositions comprising an inhibitor of the invention are also intended, such as a composition of substantially pure inhibitor, including a specific stereochemical form thereof, or a composition comprising mixtures of inhibitors of the invention in any ratio, including two or more stereochemical forms, such as in a racemic or non-racemic mixture.

In one embodiment, the small molecule therapeutic agent of comprised within the microsphere comprises an analog or derivative of a therapeutic agent described herein.

In one embodiment, the small molecules described herein are candidates for derivatization. As such, in certain instances, the analogs of the small molecules described herein that have modulated potency, selectivity, and solubility are included herein and provide useful leads for drug discovery and drug development. Thus, in certain instances, during optimization new analogs are designed considering issues of drug delivery, metabolism, novelty, and safety.

In some instances, small molecule therapeutic agents described herein are derivatized/analoged as is well known in the art of combinatorial and medicinal chemistry. The analogs or derivatives can be prepared by adding and/or substituting functional groups at various locations. As such, the small molecules described herein can be converted into derivatives/analogs using well known chemical synthesis procedures. For example, all of the hydrogen atoms or substituents can be selectively modified to generate new analogs. Also, the linking atoms or groups can be modified into longer or shorter linkers with carbon backbones or hetero atoms. Also, the ring groups can be changed so as to have a different number of atoms in the ring and/or to include hetero atoms. Moreover, aromatics can be converted to cyclic rings, and vice versa. For example, the rings may be from 5-7 atoms, and may be homocycles or heterocycles.

As used herein, the term "analog," "analogue," or "derivative" is meant to refer to a chemical compound or molecule made from a parent compound or molecule by one or more chemical reactions. As such, an analog can be a structure having a structure similar to that of the small molecule therapeutic agents described herein or can be based on a scaffold of a small molecule therapeutic agents described herein, but differing from it in respect to certain components or structural makeup, which may have a similar or opposite action metabolically. An analog or derivative of any of a small molecule inhibitor in accordance with the present invention can be used to treat a disease or disorder.

In one embodiment, the small molecule therapeutic agents described herein can independently be derivatized/analoged by modifying hydrogen groups independently from each other into other substituents. That is, each atom on each molecule can be independently modified with respect to the other atoms on the same molecule. Any traditional modification for producing a derivative/analog can be used. For example, the atoms and substituents can be independently comprised of hydrogen, an alkyl, aliphatic, straight chain aliphatic, aliphatic having a chain hetero atom, branched aliphatic, substituted aliphatic, cyclic aliphatic, heterocyclic aliphatic having one or more hetero atoms, aromatic, heteroaromatic, polyaromatic, polyamino acids, peptides, polypeptides, combinations thereof, halogens, halo-substituted aliphatics, and the like. Additionally, any ring group on a compound can be derivatized to increase and/or decrease ring size as well as change the backbone atoms to carbon atoms or hetero atoms.

Nucleic Acid Therapeutic Agents

In other related aspects, the therapeutic agent is an isolated nucleic acid. In certain embodiments, the isolated nucleic acid molecule is one of a DNA molecule or an RNA molecule. In certain embodiments, the isolated nucleic acid molecule is a cDNA, mRNA, or miRNA molecule. In one embodiment, the isolated nucleic acid molecule encodes a therapeutic peptide. In some instances, the therapeutic agent is an siRNA, miRNA, or antisense molecule, which inhibits a targeted nucleic acid. In one embodiment, the nucleic acid comprises a promoter/regulatory sequence such that the nucleic acid is preferably capable of directing expression of the nucleic acid. Thus, the invention encompasses expression vectors and methods for the introduction of exogenous DNA into cells with concomitant expression of the exogenous DNA in the cells such as those described, for example, in Sambrook et al. (2012, Molecular Cloning: A Laboratory Manual, Cold Spring Harbor Laboratory, New York), and in Ausubel et al. (1997, Current Protocols in Molecular Biology, John Wiley & Sons, New York) and as described elsewhere herein.

In another aspect of the invention, a targeted gene or protein, can be inhibited by way of inactivating and/or sequestering the targeted gene or protein. As such, inhibiting the activity of the targeted gene or protein can be accomplished by using a nucleic acid molecule encoding a transdominant negative mutant.

In one embodiment, siRNA is used to decrease the level of a targeted protein. RNA interference (RNAi) is a phenomenon in which the introduction of double-stranded RNA (dsRNA) into a diverse range of organisms and cell types causes degradation of the complementary mRNA. In the cell, long dsRNAs are cleaved into short 21-25 nucleotide small interfering RNAs, or siRNAs, by a ribonuclease known as Dicer. The siRNAs subsequently assemble with protein components into an RNA-induced silencing complex (RISC), unwinding in the process. Activated RISC then binds to a complementary mRNA transcript by base pairing interactions between the siRNA antisense strand and the mRNA. The bound mRNA is cleaved and sequence specific degradation of mRNA results in gene silencing. See, for example, U.S. Pat. No. 6,506,559; Fire et al., 1998, Nature 391(19):306-311; Timmons et al., 1998, Nature 395:854; Montgomery et al., 1998, TIG 14 (7):255-258; David R. Engelke, Ed., RNA Interference (RNAi) Nuts & Bolts of RNAi Technology, DNA Press, Eagleville, P A (2003); and Gregory J. Hannon, Ed., RNAi A Guide to Gene Silencing, Cold Spring Harbor Laboratory Press, Cold Spring Harbor, NY (2003). Soutschek et al. (2004, Nature 432:173-178) describe a chemical modification to siRNAs that aids in intravenous systemic delivery. Optimizing siRNAs involves consideration of overall G/C content, C/T content at the termini, Tm and the nucleotide content of the 3' overhang. See, for instance, Schwartz et al., 2003, Cell, 115:199-208 and Khvorova et al., 2003, Cell 115:209-216. Therefore, the present invention also includes methods of decreasing levels of PTPN22 using RNAi technology.

In another aspect, the invention includes a vector comprising an siRNA or antisense polynucleotide. Preferably, the siRNA or antisense polynucleotide is capable of inhibiting the expression of a target polypeptide. The incorporation of a desired polynucleotide into a vector and the choice of vectors is well-known in the art as described in, for example, Sambrook et al. (2012), and in Ausubel et al. (1997), and elsewhere herein.

In certain embodiments, the expression vectors described herein encode a short hairpin RNA (shRNA) therapeutic agents. shRNA molecules are well known in the art and are directed against the mRNA of a target, thereby decreasing the expression of the target. In certain embodiments, the encoded shRNA is expressed by a cell, and is then processed into siRNA. For example, in certain instances, the cell possesses native enzymes (e.g., Dicer) that cleaves the shRNA to form siRNA.

In order to assess the expression of the siRNA, shRNA, or antisense polynucleotide, the expression vector to be introduced into a cell can also contain either a selectable marker gene or a reporter gene or both to facilitate identification of expressing cells from the population of cells sought to be transfected or infected using a the microsphere of the invention. In other embodiments, the selectable marker may be carried on a separate piece of DNA and also be contained within the microsphere. Both selectable markers and reporter genes may be flanked with appropriate regulatory sequences to enable expression in the host cells. Useful selectable markers are known in the art and include, for example, antibiotic-resistance genes, such as neomycin resistance and the like.

Therefore, in another aspect, the microsphere may contain a vector, comprising the nucleotide sequence or the construct to be delivered. The choice of the vector will depend on the host cell in which it is to be subsequently introduced. In a particular embodiment, the vector of the invention is an expression vector. Suitable host cells include a wide variety of prokaryotic and eukaryotic host cells. In specific embodiments, the expression vector is selected from the group consisting of a viral vector, a bacterial vector and a mammalian cell vector. Prokaryote- and/or eukaryote-vector based systems can be employed for use with the present invention to produce polynucleotides, or their cognate polypeptides. Many such systems are commercially and widely available.

By way of illustration, the vector in which the nucleic acid sequence is introduced can be a plasmid, which is or is not integrated in the genome of a host cell when it is introduced in the cell. Illustrative, non-limiting examples of vectors in which the nucleotide sequence of the invention or the gene construct of the invention can be inserted include a tet-on inducible vector for expression in eukaryote cells.

The vector may be obtained by conventional methods known by persons skilled in the art (Sambrook et al., 2012). In a particular embodiment, the vector is a vector useful for transforming animal or insect cells.

In one embodiment, the recombinant expression vectors may also contain nucleic acid molecules, which encode a peptide or peptidomimetic.

A promoter may be one naturally associated with a gene or polynucleotide sequence, as may be obtained by isolating the 5' non-coding sequences located upstream of the coding segment and/or exon. Such a promoter can be referred to as "endogenous." Similarly, an enhancer may be one naturally associated with a polynucleotide sequence, located either downstream or upstream of that sequence. Alternatively, certain advantages will be gained by positioning the coding polynucleotide segment under the control of a recombinant or heterologous promoter, which refers to a promoter that is not normally associated with a polynucleotide sequence in its natural environment. A recombinant or heterologous enhancer refers also to an enhancer not normally associated with a polynucleotide sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (U.S. Pat. Nos. 4,683,202, 5,928,906). Furthermore, it is contemplated the control sequences that direct transcription and/or expression of sequences within non-nuclear organelles such as mitochondria, chloroplasts, and the like, can be employed as well.

Naturally, it will be important to employ a gene promoter and/or enhancer that effectively directs the expression of the DNA segment in the cell type, organelle, and organism chosen for expression. Those of skill in the art of molecular biology generally know how to use promoters, enhancers, and cell type combinations for protein expression, for example, see Sambrook et al. (2012). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

The recombinant expression vectors may also contain a selectable marker gene, which facilitates the selection of host cells. Suitable selectable marker genes are genes encoding proteins such as G418 and hygromycin, which confer resistance to certain drugs, 3-galactosidase, chloramphenicol acetyltransferase, firefly luciferase, or an immunoglobulin or portion thereof such as the Fc portion of an immunoglobulin preferably IgG. The selectable markers may be introduced on a separate vector from the nucleic acid of interest.

Following the generation of the siRNA polynucleotide, a skilled artisan will understand that the siRNA polynucleotide will have certain characteristics that can be modified to improve the siRNA as a therapeutic compound. Therefore, the siRNA polynucleotide may be further designed to resist degradation by modifying it to include phosphorothioate, or other linkages, methylphosphonate, sulfone, sulfate, ketyl, phosphorodithioate, phosphoramidate, phosphate esters, and the like (see, e.g., Agrwal et al., 1987, Tetrahedron Lett. 28:3539-3542; Stec et al., 1985 Tetrahedron Lett. 26:2191-2194; Moody et al., 1989 Nucleic Acids Res. 12:4769-4782; Eckstein, 1989 Trends Biol. Sci. 14:97-100; Stein, In: Oligodeoxynucleotides. Antisense Inhibitors of Gene Expression, Cohen, ed., Macmillan Press, London, pp. 97-117 (1989)).

Any polynucleotide may be further modified to increase its stability in vivo. Possible modifications include, but are not limited to, the addition of flanking sequences at the 5' and/or 3' ends; the use of phosphorothioate or 2' O-methyl rather than phosphodiester linkages in the backbone; and/or the inclusion of nontraditional bases such as inosine, queosine, and wybutosine and the like, as well as acetyl- methyl-, thio- and other modified forms of adenine, cytidine, guanine, thymine, and uridine.

In one embodiment of the invention, an antisense nucleic acid sequence, which is expressed by a plasmid vector is used as a therapeutic agent to inhibit the expression of a target protein. The antisense expressing vector is used to transfect a mammalian cell or the mammal itself, thereby causing reduced endogenous expression of the target protein.

Antisense molecules and their use for inhibiting gene expression are well known in the art (see, e.g., Cohen, 1989, In: Oligodeoxyribonucleotides, Antisense Inhibitors of Gene Expression, CRC Press). Antisense nucleic acids are DNA or RNA molecules that are complementary, as that term is defined elsewhere herein, to at least a portion of a specific mRNA molecule (Weintraub, 1990, Scientific American 262:40). In the cell, antisense nucleic acids hybridize to the corresponding mRNA, forming a double-stranded molecule thereby inhibiting the translation of genes.

The use of antisense methods to inhibit the translation of genes is known in the art, and is described, for example, in Marcus-Sakura (1988, Anal. Biochem. 172:289). Such antisense molecules may be provided to the cell via genetic expression using DNA encoding the antisense molecule as taught by Inoue, 1993, U.S. Pat. No. 5,190,931.

Alternatively, antisense molecules of the invention may be made synthetically and then provided to the cell. Antisense oligomers of between about 10 to about 30, and more preferably about 15 nucleotides, are preferred, since they are easily synthesized and introduced into a target cell. Synthetic antisense molecules contemplated by the invention include oligonucleotide derivatives known in the art which have improved biological activity compared to unmodified oligonucleotides (see U.S. Pat. No. 5,023,243).

In one embodiment of the invention, a ribozyme is used as a therapeutic agent to inhibit expression of a target protein. Ribozymes useful for inhibiting the expression of a target molecule may be designed by incorporating target sequences into the basic ribozyme structure, which are complementary, for example, to the mRNA sequence encoding the target molecule. Ribozymes targeting the target molecule, may be synthesized using commercially available reagents (Applied Biosystems, Inc., Foster City, CA) or they may be genetically expressed from DNA encoding them.

In one embodiment, the therapeutic agent may comprise one or more components of a CRISPR-Cas system, where a guide RNA (gRNA) targeted to a gene encoding a target molecule, and a CRISPR-associated (Cas) peptide form a complex to induce mutations within the targeted gene. In one embodiment, the therapeutic agent comprises a gRNA or a nucleic acid molecule encoding a gRNA. In one embodiment, the therapeutic agent comprises a Cas peptide or a nucleic acid molecule encoding a Cas peptide.

Polypeptide Therapeutic Agents

In other related aspects, the therapeutic agent includes an isolated peptide that modulates a target. For example, in one embodiment, the peptide of the invention inhibits or activates a target directly by binding to the target thereby modulating the normal functional activity of the target. In another embodiment, the peptide of the invention modulates the target by competing with endogenous proteins. In yet another embodiment, the peptide of the invention modulates the activity of the target by acting as a transdominant negative mutant.

The variants of the polypeptide therapeutic agents may be (i) one in which one or more of the amino acid residues are substituted with a conserved or non-conserved amino acid residue (preferably a conserved amino acid residue) and such substituted amino acid residue may or may not be one encoded by the genetic code, (ii) one in which there are one or more modified amino acid residues, e.g., residues that are modified by the attachment of substituent groups, (iii) one in which the polypeptide is an alternative splice variant of the polypeptide of the present invention, (iv) fragments of the polypeptides and/or (v) one in which the polypeptide is fused with another polypeptide, such as a leader or secretory sequence or a sequence which is employed for purification (for example, Histidine tag) or for detection (for example, Sv5 epitope tag). The fragments include polypeptides generated via proteolytic cleavage (including multi-site proteolysis) of an original sequence. Variants may be post-translationally, or chemically modified. Such variants are deemed to be within the scope of those skilled in the art from the teaching herein.

Antibody Therapeutic Agents

The invention also contemplates a microsphere comprising an antibody, or antibody fragment, specific for a target. That is, the antibody can inhibit a target to provide a beneficial effect.

The antibodies may be intact monoclonal or polyclonal antibodies, and immunologically active fragments (e.g., a Fab or (Fab)2 fragment), an antibody heavy chain, an antibody light chain, humanized antibodies, a genetically engineered single chain FV molecule (Ladner et al, U.S. Pat. No. 4,946,778), or a chimeric antibody, for example, an antibody which contains the binding specificity of a murine antibody, but in which the remaining portions are of human origin. Antibodies including monoclonal and polyclonal antibodies, and fragments and chimeras, may be prepared using methods known to those skilled in the art.

Antibodies can be prepared using intact polypeptides or fragments containing an immunizing antigen of interest. The polypeptide or oligopeptide used to immunize an animal may be obtained from the translation of RNA or synthesized chemically and can be conjugated to a carrier protein, if desired. Suitable carriers that may be chemically coupled to peptides include bovine serum albumin and thyroglobulin, keyhole limpet hemocyanin. The coupled polypeptide may then be used to immunize the animal (e.g., a mouse, a rat, or a rabbit).

Edible Compositions

The present invention provides edible compositions comprising one or more microspheres of the present invention. The relative amounts of the microspheres, the edible material, and any additional ingredients in an edible material of the invention will vary, depending upon the identity, size, and condition of the subject treated. In one embodiment, the edible composition comprises a microsphere comprising an agent. In one embodiment, the edible composition comprises a microsphere comprising a sweetener. In one embodiment, the edible composition comprises a microsphere comprising an agent and a microsphere comprising a sweetener.

Enjoyable food compositions and flavors can increase compliance of usage by consumers (e.g. children and elderly) and patients under clinical administration of the functional food. For example, typical flavorings for use in the compositions described herein include chocolate, vanilla, mints, natural fruit flavors, etc. Edible materials include, but are not limited to frozen dairy products such as frozen yogurts, ice creams, sorbets, gelatos, etc., other dairy products such as yogurt, fruits, vegetables, meat, a carbohydrate food product, botanicals, confections, and combinations thereof. The substances can be in natural form, puree form, frozen, soft, etc. Other edible materials that may comprise the microspheres of the invention include liquids such as water, juices, coffee and tea products, soft drinks, liquid confectionery beverages, and combinations thereof. In some embodiments, the edible material is an edible oral strip, a gelatin candy, a hard candy, chocolate, ice cream, pudding, apple sauce, yogurt or other foods.

A membrane can be engineered for various functional food applications by being, for example, stronger, thinner/thicker, or taste a particular way, with methods in addition to adjusting the properties of an alginate solution. Adding suspended particles of food, nutraceuticals, compounds beneficial to gastrointestinal health, or other particles at least partially insoluble in water can achieve desirable properties important to the consumer and patient.

Oral Strips

In one embodiment, the edible material is an edible oral strip. In one embodiment, the edible oral strips may be any type of conventional dissolving oral edible strip. In some embodiments, the edible oral strip is a quick-dissolve strip. The edible oral strip may be of any shape, such as oblong, square, round, rectangular, etc. The quick-dissolve strip may also have a variety of sizes and thicknesses.

The edible oral strip will have a thickness suitable for its intended application. The appropriate thickness will allow the edible oral strip to adequately release the flavoring and/or coloring ingredients. Also, the thickness will be suitable for manufacturing, cutting or stamping, packaging and handling. The oral strip thickness may be tested by any procedure known to one of ordinary skill in manufacturing. The oral strips of the invention are preferably from about 30

μm to about 70 μm in thickness, and in certain embodiments preferably from about 25 μm to about 50 μm in thickness.

The oral strip compositions of the invention may include further ingredients such as release aids, processing aids, colorants, food dyes, and the like. The edible film matrix compositions in accordance with the present invention may include one or more processing aids such as texture adjusting agents, cooling agents, stabilizing agents, emulsifying agents, thickening agents, binding agents, sweeteners, mixtures thereof, and the like.

By way of example, and not limitation, the film layer can be produced using a highly water-soluble polymer(s) comprising a natural and/or synthetic water-soluble polymer. The polymer preferably has good film moldability, produces a soft flexible film, has suitable tensile strength, and is safe for human consumption. Such polymer(s) can be a water-soluble cellulose derivative like hypromellose (hydroxypropylmethylcellulose), hydroxypropyl cellulose (HPC), methyl cellulose, hydroxypropyl alkylcellulose, carboxymethyl cellulose or the salt of carboxymethyl cellulose. The film layer may also be produced using poly vinyl alcohol, poly vinyl pyrrolidone, polyalkylene glycol, hydroxy propyl starch, alginic acid or its salt, poly-saccharide or its derivatives such as trangacanth, gum gelatin, collagen, denatured gelatin, and collagen treated with succinic acid, anhydrous phthalic acid, pullulan, maltodextrin, pectin, alginates, carrageenan, guar gum, exudate gums (arabic, ghatti, karaya, tragacanth), extract gums (.beta.-glucans, inulins, konjac, larch), seed gums (locust bean, guar, pysllium, quince, fenugreek, tara), pectins (high methoxy-, low methoxy-, amidated), microbial gums (xanthan, curdlan, pullulan, gellan, scleroglucan, welan, rhamsan), modified celluloses (methylcellulose, hydroxypropylcellulose, hydroxypropylmethyl cellulose, sodium carboxymethyl cellulose), seaweed hydrocolloid extracts (sodium alginate, propylenegly-col alginate, modified alginate, ammonium alginate, alginic acid, carageenans (iota, kappa, .kappa., lambda, lamda), dextrins, dextran, hydrogenated starch hydrolyzates, polydextrose, agar, modified agar, gelatins (both type A and B, hydrolyzed gelatin, modified gelatin), milk proteins (whole milk protein, sodium caseinate, calcium caseinate, whey proteins, albumins, lactoglobulins), pregelatinized starches, seed proteins (from soy, sunflower, cottonseed, peanut), cereal proteins (wheat, corn, oat, rice), fractionated proteins, hydrolyzed proteins, chitosan, and modified chitosan, other gelatins, mixtures of any of the foregoing, and the like.

In some embodiments, the thermoplastic food grade material which may be used in the edible oral strips of the invention include, but are not limited to, hydroxypropylmethyl cellulose, hydroxyethyl cellulose, hydroxypropyl cellulose, hydroxyalkyl methyl cellulose, polyvinyl pyrrolidone, carboxymethyl cellulose, polyvinyl alcohol, sodium alginate, polyethylene glycol, xanthan gum, tragacanth gum, guar gum, pullulan, acacia gum, arabic gum, mixtures of any of the foregoing, and the like. In some embodiments, the thermoplastic food grade material which is incorporated into the oral strips of the invention comprises a mixture of two or more hydroxypropylcelluloses.

The oral strips of the invention may also comprise poorly water-soluble cellulose derivatives including ethyl cellulose, cellulose acetate and butyl cellulose; shellac; higher fatty acids including steric acid and palmitic acid, an acrylic acid copolymer or its sodium, potassium or ammonium salt.

Additional agents that may be incorporated into the edible oral strips of the invention include breath freshening compounds like menthol, peppermint oil, cinnamon oil, anise, and the like; other flavors or fragrances commonly used for oral hygiene; and/or actives used for dental and/or oral cleansing like quarternary ammonium bases. Other useful active ingredients include zinc oxide, or local anesthetics. The effect of flavors may be enhanced using flavor enhancers like tartaric acid, citric acid, vanillin, ethyl vanillin, or the like. Colorants which may optionally be mixed in the film must be safe in terms of toxicity and should be accepted by the Food and Drug Administration for use in cosmetics.

Plasticizers which may be included in the edible oral strips of the present invention include, but are not limited to: low molecular weight polyols (e.g., glycerin, propylene glycol); polyethylene glycols with molecular weight less than 1,000 Daltons; polypropylene glycols with molecular weight of 200 Daltons or less; glycol esters (e.g., propylene glycol monethyl ether); esters (e.g., sorbitol lactate, ethyl glycol); amines (e.g. triethanolamine); and sugars (e.g. sorbitol, sucrose), glycerin (glycerol), propylene glycol, polyethylene glycol, triacetin, diacetin, triethylcitrate, a polyol, a modified polyol or food grade materialic alcohol or polyol or urea, triacetin, monoacetin, diacetin, diglycerol, propylene glycol, triethylene glycol, erythritol, sorbitol, mannitol, maltitol, hydrogenated starch syrup, polyvinyl alcohol, polyethylene oxides, polyethylene glycol, urea, mixtures thereof and the like. In some embodiments, the plasticizer is employed in an amount sufficient to impart flexibility to the resulting film sheet.

Detackifiers which may be included in the edible oral strips of the present invention include but are not limited to: water insoluble polymers (e.g., cellulose acetate phthalate, polymethacrylate); lipids and fatty acids (e.g., carnauba wax, cetyl alcohol); inorganic diluents (e.g., calcium carbonate, talc); disintegrants (e.g., crosarmellose sodium, starch, microcrystalline cellulose); and, sugars (e.g., mannitol, xylitol, maltitol, lactose).

Taste modifying agents which may be included in the edible oral strips of the present invention include but are not limited to: flavoring agents, sweetening agents and taste masking agents. Examples of taste modifying agents suitable for use with the present invention include: the essential oils or water soluble extracts of menthol, wintergreen, peppermint, sweet mint, spearmint, vanillin, cherry, chocolate, cinnamon, clove, lemon, orange, raspberry, rose, spice, violet, herbal, fruit, strawberry, grape, licorice, thymol, eucalyptol, honey, pineapple, peach, kiwi, *papaya*, mango, coconut, apple, coffee, plum, watermelon, nuts, durian and green tea. Encapsulation of the active agent or combination of active agents may also be utilized to achieve taste masking of active agents that are bitter.

Buffering agents may also be optionally incorporated into the edible oral strips of the present invention, and include acidulants and alkalizing agents. Examples of buffering agents suitable for use with the present invention include but are not limited to: citric acid, fumaric acid, lactic acid, tartaric acid, malic acid, as well as sodium citrate, sodium bicarbonate and carbonate, and sodium or potassium phosphate.

Coloring agents suitable for use in the edible oral strips of the present invention include, but are not limited to: FD & C coloring agents, natural coloring agents, and natural juice concentrates, pigments such as titanium oxide, silicon dioxide and zinc oxide.

Preservatives suitable for use in the edible films of the present invention include but are not limited to: anti-microbial agents and non-organic compounds. Examples of preservatives suitable for use with the present invention include sodium benzoate, parabens and derivatives, sorbic acid and its salts, propionic acids and its salts, sulfur dioxide and sulfites, acetic acid and acetates, nitrites and nitrates.

Surfactants which may be included in the edible oral films of the present invention include, but are not limited to, mono- and di-glycerides of fatty acids and polyoxyethylene sorbitol esters, such as Atmos 300 and Polysorbate 80, pluronic acid, sodium lauryl sulfate, and the like.

As discussed elsewhere herein, various optional ingredients such as conventionally used in the art, may be included in the compositions of the present invention. For example, colorings, sweeteners (such as sucrose and sucralose), food acids (such as malic acid and citric acid), salts (such as sodium chloride, calcium citrate and calcium chloride), fragrances, diluents, flavor maskers, flavor enhancers, plasticizers, fillers, preservatives, anti-oxidants, pH modifying agents, thickening agents, binding agents, cooling agents, emulsifying agents, stabilizers, lubricants, and the like may be employed herein if desired.

In one embodiment, the oral strip comprises two or more of pullulan, hydroxypropyl methylcellulose, xanthan gum, glycerol, mannitol, sucralose, TBHQ, and peppermint oil.

The edible oral strips of the present invention may be prepared, e.g., as matrix film compositions. The edible oral strips of the present invention may be manufactured utilizing various techniques well known to those having ordinary skill in the art.

In certain embodiments, the compositions of the present invention may be manufactured by any suitable mixing process. For example, in some, all of the ingredients except water are mixed together to form a granular powder. Thereafter, the water is slowly added, and mixed well. In other embodiments, the process may be reversed. The resultant mixture may then be cast, and then dried to obtain a film having a desired thickness and tensile strength.

The mixing methods described above may be carried out utilizing various mixing apparatuses. For example, a suitable apparatus for the preparation of the matrix compositions described herein includes a storage vessel which contains a solution to be formed into film strips; an endless belt supported by a plurality of rotating rolls which carries a cast layer of solution from the storage vessel beneath a heated dryer or heated air for drying, such that the solution dries and forms a film; thereafter the film is stripped from the endless belt by a film stripper. In such systems, for example, the solution is continuously cast on the endless belt allowing for the continuous production of film.

The edible oral strips of the present invention may also be prepared by forming matrix film compositions utilizing an extrusion process. For example, in certain embodiments, the matrix film compositions of the present invention are manufactured by extruding a plasticized mixture of thermoplastic food grade material and a flavoring component through an extruder pre-heated to a temperature from about 100° F. to about 250° F. to form an extrudate, and shaping the extrudate into a desired shape and thickness for further processing.

The processing conditions and amounts of ingredients may be adjusted to optimize the formation of suitable film matrixes.

The ratio of thermoplastic food grade material (film forming food grade material) to water is such that acceptable properties are obtained during or after the manufacturing process.

In some embodiments, the invention is directed to a manufacturing process where at least one of the wet ingredients is sprayed onto the dry ingredients prior to introduction into the extruder. In embodiment, water may be added to the wet ingredients prior to the wet ingredients being sprayed onto the dry ingredients. In other embodiments, water may be added to a mixture of wet and dry ingredients prior to the extrusion process.

In some embodiments, the films are cooled prior to further processing. In certain other embodiments, a chilling table may be used to cool the films. In still other embodiments, the shaping device, e.g., drum dryer is cooled.

The edible oral strips of the present invention may be manufactured in any effective manner known to those skilled in the art. For example, U.S. Patent Application Nos. 20010022964, 20020131990 and 20020019447 and U.S. Pat. Nos. 6,419,903, 3,931,146, 5,411,945, 6,010,716, 5,629,003, 5,948,430, 6,177,096, 6,284,264, 5,700,478, 6,449,925, 4,072,551, 4,083,741, all of which are incorporated herein by reference as if fully set forth herein, describe methods for making edible films. These, and other methods known in the art, or described herein, may be used in accordance with the present invention.

The edible film compositions are preferably cut into suitably sized oral strips which contain effective amounts of the active agent(s) and the flavor(s). The oral strips may be packaged in any suitable manner for use or sale.

Gelatin Candies

In one embodiment, the edible material comprising one or more microspheres is a gelatin candy. In one embodiment, the gelatin candy may be any type of conventional gelatin candy. The gelatin candy may be of any shape, such as oblong, square, round, rectangular, or molded into a shape. The gelatin candy may also have a variety of sizes.

In one embodiment, the gelatin candy comprises a binding agent, a sweetener, and at least one microsphere of the invention. In one embodiment, the gelatin candy comprises a microsphere comprising an agent. In one embodiment, the gelatin candy comprises a microsphere comprising a sweetener. In one embodiment, the gelatin candy comprises a microsphere comprising an agent and a microsphere comprising a sweetener.

In addition to the microsphere, the gelatin candy may also include the any combination of vitamins, minerals, antioxidants, soluble and insoluble fiber, herbs, plants, amino acids, digestive enzymes, or any other supplements digested to promote the health and well-being of a person. Inclusion of any of these dietary supplements will depend in part on their compatibility with the material encapsulated within the microspheres.

The gelatin candy may include sweeteners, a binding agent, and natural and/or artificial flavors, colors, and preservatives. For example, in one embodiment, the gummy candy may include glucose syrup, natural cane juice, gelatin, citric acid, lactic acid, glycerol, natural colors, natural flavors, fractionated coconut oil, and carnauba wax.

The type of gelling agent is not particularly limited. For example, pectin, agar, arabic gum, xanthan gum, tragacanth gum, karaya gum, ghatti gum, guar gum, gellan gum, locust bean gum, alginic acid or its salt (e.g., sodiumalginate), carrageenan, gelatin, dextrin, starches (corn starch, rice starch, wheat starch, potato starch, *pueraria* starch, tapioca starch, carboxymethyl starch, hydroxypropyl starch, hydroxyethyl starch, chemically cross-linked starch, alpha-starch, and so on), celluloses (hydroxypropylmethyl cellulose, carboxymethyl cellulose, methyl cellulose, methylethyl cellulose, hydroxypropyl cellulose, crystalline cellulose and so on), polyvinyl alcohol, polyvinylpyrrolidone, polyethylene glycol(macrogol), or mannans can be used singly or in an appropriate combination.

Embodiments of this invention may further contain, as needed, a stabilizer, surfactant, solubilizer, buffer, sweetener, seasoning, suspending agent, coating, flavor/spice (aromatic), colorant, pH adjuster, viscosity increasing agent, Ca-supplier, dispersant, antiseptic (preservative), solvent (dissolving agent) and the like. For example, sodium alginate, various gums, glycerin, etc. can be used as a stabilizer; sodium lauryl sulfate, polysorbate 80, or the like can be used as a surfactant; ethanol or the like can be used as a solubilizer; phosphate, carbonate, and so on can be used as a buffer; purified sucrose, aspartame, fructose, sorbitol, xylitol, glucose, mannitol, maltose, trehalose, palatinose, powdered-reduced maltose millet jelly, oligosaccharide, erythritol, stevioside, glycyrrhizin, etc. can be used as a sweetener; menthol, edible fruit juice, caramel, or glucono-(-lactone, etc. can be used as a seasoning; sodium alginate, arabic gum, lactose, or the like can be used as a suspending agent; purified shellac, hydroxypropylmethyl cellulose phthalate, or the like can be used as a coating; fruit flavor, prune, mint oil, and so on can be used as a flavor/spice (aromatic); orange essence, edible dye, caramel, or the like can be used as a colorant; citric acid or its salt, tartaric acid or its salt, succinic acid, lactic acid, calcium lactate, phosphate, glucono-.delta.-lactone, etc. can be used as a pH adjuster; dextrin, xantham gum, soybean lecithin, polyethylene glycol, etc. can be used as a viscosity increasing agent; calcium lactate, calcium hydrogenphosphate, calcium carbonate, calcium chloride, calcium citrate, calcium sulfate, etc. can be used as a Ca-supplier; arabic gum, starches, crystalline cellulose, lactose, etc. can be used as a dispersant; sorbic acid or its salt, benzoic acid or its salt, p-oxybenzoates, or the like can be used as an antiseptic (preservative); and purified water or ethanol, or the like can be used as a solvent (dissolving agent).

The gelatin candy of the present invention may optionally also include an inert diluent. Any generally accepted soluble or insoluble inert diluent material can be used. In one embodiment, the inert diluent comprises a monosaccharide, a disaccharide, a polyhydric alcohol, a cellulose (such as microcrystalline cellulose), starches, and/or mixtures thereof. Examples of suitable inert pharmaceutical fillers include sucrose, dextrose, lactose, microcrystalline cellulose, xylitol, fructose, sorbitol, mixtures thereof and the like. However, it is known that soluble pharmaceutical fillers such as dextrose, sucrose, or mixtures thereof may be used.

In one embodiment, a buffer, such as sodium bisulfate or sodium citrate, may be mixed into the gelling compound to regulate the pH of the mixture.

In one embodiment, the gelatin candy may include additives. Additives include, but are not limited to, sodium citrate, sweeteners such as sugar (for example, sucrose or natural cane juice), sucralose, glycerol, or syrup (corn, glucose, rice, tapioca) and corn starch, in liquid and/or powdered form.

To obtain a desired color and taste, coloring and flavoring may be added to the gelatin candy. For example, food acids including citric acid, ascorbic acid, malic acid, lactic acid, adipic acid, fumaric acid, tartaric acid, or any other suitable food acid or combinations thereof. In one embodiment, the flavoring, coloring, and acid may be continuously added to (e.g., dripped on) cooked gelatin candy as the candy moves through the dosier to the mogul machine.

In addition to food acid, coloring and titanium dioxide may be added to the gelatin candy formulation. Coloring may be added to give the candy a desired color or colors. Coloring may include natural coloring such as black carrot, annatto, tumeric, and purple berry concentrate, or artificial coloring such as yellow 5, red 3, blue 1 or white food coloring.

Titanium dioxide may be added to the gelatin candy to provide sheen. Titanium dioxide may also stabilize the gelatin candy formulation so the coloring does not bleed when it is handled, packaged, or stored.

Hard Candy

In one embodiment, the edible material is a hard candy, such as a hard fruit candy or a lollipop. In one embodiment, the hard candy may be any type of conventional hard candy. The hard candy may be of any shape, such as oblong, square, round, rectangular, or molded into a shape. The hard candy may also have a variety of sizes.

In one embodiment, the hard candy comprises a binding agent, a sweetener, and at least one microsphere of the invention. In one embodiment, the hard candy comprises a microsphere comprising an agent. In one embodiment, the hard candy comprises a microsphere comprising a sweetener. In one embodiment, the hard candy comprises a microsphere comprising an agent and a microsphere comprising a sweetener.

Hard candies are preferably made by intermixing the microspheres of the invention with the other non-medicinal lollipop ingredients (e.g., candy, sorbitol, flavoring, coloring, etc.) during the making of the lollipops. The non-medicinal lollipop ingredients are preferably selected to slowly dissolve and/or melt in the patient's mouth in a manner similar to that of a traditional lollipop, so as to release the medicaments over the course of dissolution and/or melting. The medicaments may be incorporated into the lollipop in other ways, e.g. by coating onto the exterior of a lollipop, but incorporation during manufacture is generally preferable so that the medicaments are more uniformly dispersed throughout the resulting candy matrix.

Methods for making conventional hard candies are well known in the art. In one embodiment, the hard candies are made by intermixing the various medicaments and non-medicinal ingredients in the molten or partially molten state by heating the ingredients to a temperature effective to melt or partially melt at least part of the ingredients, preferably at a temperature in the range of about 35° C. to about 95° C., pouring the resulting molten or partially molten mixture into a mold or molds, and cooling the lollipop mixture to form a hardened or semi-hardened candy attached to the holder. In one embodiment, a stick, string or other suitable object is placed into the molten mixture so that part protrudes to serve as a holder. In an alternative embodiment, the holder is placed in contact with, e.g., attached to, the hardened or semi-hardened candy after cooling. Various methods for making the hard candies may be practiced according to the knowledge of those skilled in the art.

Pharmaceutical Compositions

The present invention provides pharmaceutical compositions comprising one or more microsphere of the present invention. The relative amounts of the microsphere, the pharmaceutically acceptable carrier, and any additional ingredients in a pharmaceutical composition of the invention will vary, depending upon the identity, size, and condition of the subject treated and further depending upon the route by which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients. Said compositions may comprise additional medicinal agents, pharmaceutical agents, carriers, buffers, adjuvants, dispersing agents, diluents, and the like depending on the intended use and application.

Examples of suitable pharmaceutical carriers, excipients and/or diluents are well known in the art and include, but are not limited to, a gum, a starch (e g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

Pharmaceutically acceptable carriers for liquid formulations are aqueous or non-aqueous solutions, suspensions, emulsions or oils, Examples of non-aqueous solvents are propylene glycol, polyethylene glycol, and injectable organic esters such as ethyl oleate. Examples of oils are those of animal, vegetable, or synthetic origin, for example, peanut oil, soybean oil, olive oil, sunflower oil, turmeric oil, fish-liver oil, another marine oil, or a lipid from milk or eggs.

Aqueous carriers include water, alcoholic/aqueous solutions, emulsions or suspensions, including saline and buffered media such as phosphate buffered saline solutions, water, emulsions, such as oil/water emulsions, various types of wetting agents, sterile solutions etc. Compositions comprising such carriers can be formulated by well-known conventional methods. Suitable carriers may comprise any material which, when combined with the biologically active compound of the invention, retains the biological activity. Preparations for parenteral administration may include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles may include sodium chloride solution, Ringer's dextrose, dextrose and sodium chloride, lactated Ringer's, or fixed oils. Intravenous vehicles may include fluid and nutrient replenishes, electrolyte replenishers (such as those based on Ringer's dextrose), and the like. Preservatives and other additives may also be present including, for example, antimicrobials, anti-oxidants, chelating agents, and inert gases and the like, in addition, the pharmaceutical composition of the present invention might comprise proteinaceous carriers, e.g., serum albumin or immunoglobulin, preferably of human origin.

A pharmaceutical composition of the invention may be prepared, packaged, or sold in a formulation suitable for topical administration. There are several advantages to delivering compounds, including drugs or other therapeutic agents, into the skin (dermal drug delivery) or into the body through the skin (transdermal drug delivery). Transdermal compound delivery offers an attractive alternative to injections and oral medications. Dermal compound delivery offers an efficient way to deliver a compound to the skin of a mammal, and preferably a human, and provides a method of treatment of the skin, or otherwise provides a method of affecting the skin, without the need to break or damage the outer layer of the skin. In the present invention, dermal delivery, by way of a dermally-acting compound of the invention, provides these advantages for treatment of a skin-related condition, disorder or disease.

A number of compounds, including some drugs, will penetrate the skin effectively simply because the molecules are relatively small and potent at small doses of 0.1 mg to 15 mg/day (Kanikkannan et al., 2000, Curr. Med. Chem. 7:593-608). Many other compounds and drugs can be delivered only when an additional enhancement system is provided to "force" them to pass through the skin. Among several methods of transdermal drug delivery are electroporation, sonophoresis, iontophoresis, permeation enhancers (cyclodextrins), and liposomes. While the aforementioned methods are also included in the present invention for dermal delivery of the compounds of the invention, liposomes represent a preferred dermal delivery method.

The composition of the invention may consist of the active ingredient alone, in a form suitable for administration to a subject, or the composition may comprise at least one active ingredient and one or more pharmaceutically acceptable carriers, one or more additional ingredients, or some combination of these. The active ingredient may be present in the composition in the form of a physiologically acceptable ester or salt, such as in combination with a physiologically acceptable cation or anion, as is well known in the art. Compositions of the invention will also be understood to encompass pharmaceutical compositions useful for treatment of other conditions, disorders and diseases associated with the skin.

In one aspect, a dermal delivery vehicle of the invention is a composition comprising at least one first compound that can facilitate dermal delivery of at least one second compound associated with, or in close physical proximity to, the composition comprising the first compound. As will be understood by the skilled artisan, when armed with the disclosure set forth herein, such delivery vehicles include, but should not be limited to, liposomes, nanosomes, phospholipid-based non-liposome compositions (eg., selected cochleates), among others.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 0.001% to about 90% (w/w) active ingredient, although the concentration of the active ingredient may be as high as the solubility limit of the active ingredient in the solvent. Formulations for topical administration may further comprise one or more of the additional ingredients described herein.

The topically active pharmaceutical or cosmetic composition may be optionally combined with other ingredients such as moisturizers, cosmetic adjuvants, anti-oxidants, chelating agents, surfactants, foaming agents, conditioners, humectants, wetting agents, emulsifying agents, fragrances, viscosifiers, buffering agents, preservatives, sunscreens and the like. In another embodiment, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art.

Additional components may include, but should not be limited to those including water, oil (eg., olive oil/PEG7), biovera oil, wax (eg., jojoba wax), squalene, myristate (eg., isopropyl myristate), triglycerides (eg., caprylic triglyceride), Solulan 98, cocoa butter, shea butter, alcohol (eg., behenyl alcohol), stearate (eg., glycerol-monostearate), chelating agents (eg., EDTA), propylene glycol, SEPIGEL (Seppic, Inc., Fairfield, NJ), silicone and silicone derivatives (eg., dimethicone, cyclomethicone), vitamins (eg., vitamin E), among others.

A microsphere composition may be administered alone, or in combination with other drugs and/or agents as pharmaceutical compositions. The composition may contain one or more added materials such as carriers and/or excipients. As used herein, "carriers" and "excipients" generally refer to substantially inert, non-toxic materials that do not deleteriously interact with other components of the composition. These materials may be used to increase the amount of solids in particulate pharmaceutical compositions, such as to form a powder of drug particles. Examples of suitable carriers include water, silicone, gelatin, waxes, and the like.

Examples of normally employed "excipients," include pharmaceutical grades of mannitol, sorbitol, inositol, dextrose, sucrose, lactose, trehalose, dextran, starch, cellulose, sodium or calcium phosphates, calcium sulfate, citric acid, tartaric acid, glycine, high molecular weight polyethylene glycols (PEG), and the like and combinations thereof. In one embodiment, the excipient may also include a charged lipid and/or detergent in the pharmaceutical compositions. Suitable charged lipids include, without limitation, phosphatidylcholines (lecithin), and the like. Detergents will typically be a nonionic, anionic, cationic or amphoteric surfactant. Examples of suitable surfactants include, for example, Tergitol® and Triton® surfactants (Union Carbide Chemicals and Plastics, Danbury, Conn.), polyoxyethylenesorbitans, for example, TWEEN surfactants (Atlas Chemical Industries, Wilmington, Del.), polyoxyethylene ethers, for example, Brij®, pharmaceutically acceptable fatty acid esters, for example, lauryl sulfate and salts thereof (SDS), and the like. Such materials may be used as stabilizers and/or anti-oxidants. Additionally, they may be used to reduce local irritation at the site of administration.

In at least one embodiment, the composition is formulated in a lyophilized form. In certain embodiments, the lyophilized formulation of the composition allows for maintaining microsphere structure and achieving remarkably superior long-term stability conditions which might occur during storage or transportation of the microsphere.

Sprayable Compositions

The present invention provides sprayable compositions comprising one or more microsphere of the present invention. In one embodiment, the sprayable composition comprises a microsphere comprising an irritant. In one embodiment, the sprayable composition comprises a microsphere comprising capsaicin or dihydrocapsasin.

In one embodiment, the sprayable composition is useful for deterring an intruder, including a human or mammal intruder. In one embodiment, the sprayable composition beneficially irritates the skin and eyes of a target subject without causing long-term damage to other subjects that may inadvertently be sprayed by the composition.

Kits of the Invention

The invention also includes a kit comprising compounds useful within the methods of the invention and an instructional material that describes, for instance, the method of administering the microspheres and compositions as described elsewhere herein. The kit may comprise formulations of a pharmaceutical composition comprising the active ingredient combined with a pharmaceutically acceptable carrier, such as sterile water or sterile isotonic saline. The kit may comprise injectable formulations that may be prepared, packaged, or sold in unit dosage form, such as in ampules or in multi dose containers containing a preservative. The kit may comprise formulations including, but not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment, the active ingredient is provided in dry (i.e., powder or granular) form for reconstitution with a suitable vehicle (e.g., sterile pyrogen free water) prior to administration of the reconstituted composition.

The kit may comprise pharmaceutical compositions prepared, packaged, or sold in the form of a sterile aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic diluent or solvent, such as water or 1,3 butane diol, for example. Other acceptable diluents and solvents include, but are not limited to, Ringer's solution, isotonic sodium chloride solution, and fixed oils such as synthetic mono- or di-glycerides. Other formulations which are useful include those which comprise the active ingredient in microcrystalline form, in a liposomal preparation, or as a component of a biodegradable polymer system.

In certain embodiments, the kit comprises instructional material. Instructional material may include a publication, a recording, a diagram, or any other medium of expression which can be used to communicate the usefulness of the device or implant kit described herein. The instructional material of the kit of the invention may, for example, be affixed to a package which contains one or more instruments which may be necessary for the desired procedure. Alternatively, the instructional material may be shipped separately from the package, or may be accessible electronically via a communications network, such as the Internet.

Methods

The invention relates to methods of using the microspheres, microspheres compositions, edible compositions, and pharmaceutical compositions of the present invention. In various embodiments, the methods relate masking the taste of an agent.

The methods are useful for masking the taste of an agent encapsulated within a microsphere. In one embodiment, the method comprises administering to a subject an effective amount of a microsphere comprising a therapeutic agent, wherein the microsphere masks the taste of the therapeutic agent. In one embodiment, the method comprises administering to a subject an effective amount of an edible material comprising a microsphere comprising a therapeutic agent. In one embodiment, the method comprises administering to a subject an effective amount of an edible material comprising a microsphere comprising a therapeutic agent and a microsphere comprising a sweetener.

The release of the encapsulated therapeutic agent within microspheres is delayed by 15 to 20 seconds after the edible composition is administered so that the near instantaneous release of sweet taste stimuli from rapidly dissolving edible material initially minimizes the bitter taste of therapeutic agent. Further, edible compositions comprising a microsphere comprising a therapeutic agent and a microsphere comprising a sweetener further mask the taste of the agent as the 15 to 20 second delay in the release of the therapeutic agent from microspheres occurs simultaneously with the delayed release of sweetener from a second aliquot of microspheres.

Although the description of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, guinea pigs, cats, and dogs.

In the method of treatment, the administration of the composition of the invention may be for either "prophylactic" or "therapeutic" purpose. When provided prophylactically, the composition of the present invention is provided in advance of any symptom, although in particular embodiments the invention is provided following the onset of one or more symptoms to prevent further symptoms from developing or to prevent present symptoms from becoming worse. The prophylactic administration of composition serves to prevent or ameliorate any subsequent symptom. When provided therapeutically, the pharmaceutical composition is provided at or after the onset of a symptom. Thus, the present invention may be provided either prior to the anticipated exposure to a disorder-causing agent or disorder state or after the initiation of the disorder.

In one embodiment, the method of treatment is a method of treating an oral disease or disorder. In one embodiment, the method comprises administering a composition comprising a microsphere encapsulating an agent. In one embodiment, the microsphere is embedded in a film. In one embodiment, the microsphere slowly releases the encapsulated agent. In one embodiment, administering a composition comprises administering a composition in the oral cavity.

The invention also provides a method for encapsulating a sweetener. In one embodiment, the method comprises melting stearic acid and sweetener at a temperature of just below the temperature at which the sweetener degrades; mixing the stearic acid and sweetener with a buffer at pH of about 4.0 to about 4.25; and collecting the microspheres. In one embodiment, the method further comprises solidifying the melted stearic acid and sweetener at room temperature and melting the solidified stearic acid and sweetener at a temperature of just below the temperature at which the sweetener degrades. In one embodiment, the step mixing the stearic acid and sweetener with a buffer at pH of about 4.0 to about 4.25 is carried out at a temperature of about 60-65° C. In one embodiment, the stearic acid, sweetener and buffer is stirred rapidly at room temperature until the stearic acid, sweetener and buffer has a temperature of room temperature. In one embodiment, the temperature of just below the temperature at which the sweetener degrades is 1%-20% below the temperature at which the sweetener degrades. In one embodiment, the microspheres are collected by filtration. In one embodiment, the HEPES buffer for preparing microspheres further comprises about 0.01% xanthan gum.

The invention also provides a method for controlling the melting point of a microsphere. In one embodiment, the method comprises mixing stearic acid with a lipid or a glycoside, and forming a microsphere. In one embodiment, the microsphere is formed through the hot melt method. In one embodiment, the lipid or glycoside is selected from linoleic acid, cocoa butter, coconut oil and *Quillaja* saponin.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Suppression of Bitter Taste by Stearic Acid Microspheres that are Embedded in Edible Taste Strips The bitter taste stimulus sucrose octaacetate (SOA) was used as a model compound for bitter tasting drugs. In order to block the bitter taste of SOA in the human oral cavity, a two-step approach has been developed. Bitter taste stimuli were encapsulated in stearic acid-coated microspheres, and then these microspheres were embedded in edible taste strips which contained the sweet taste stimulus sucralose. Stearic acid is a solid at room temperature, elicits little to no taste response in humans, and physically blocks bitter taste stimuli that are encapsulated within stearic acid microspheres.

Figure 2:
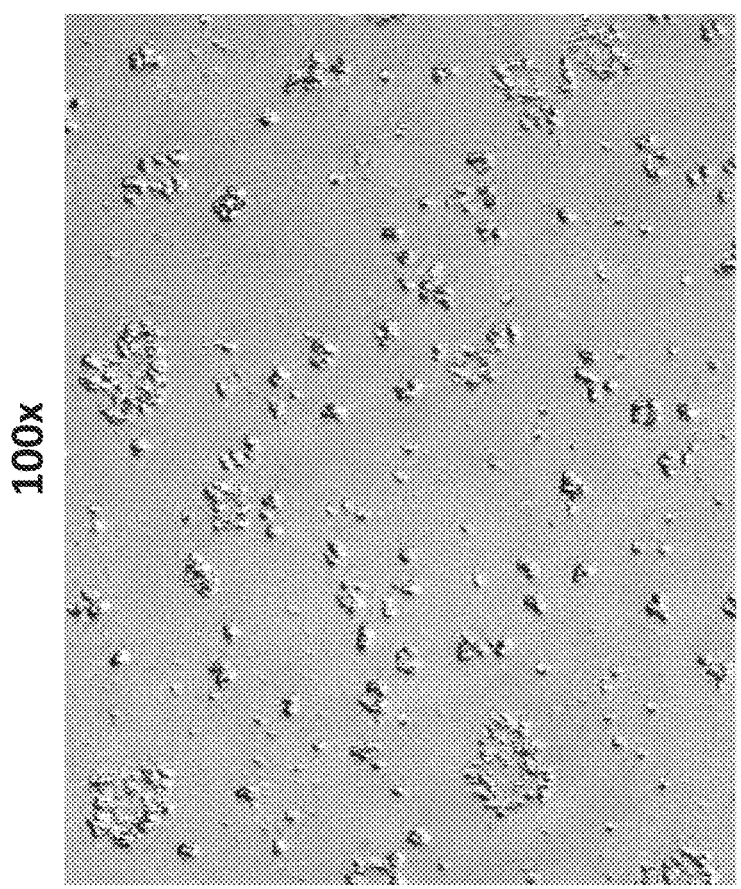
FIG. 2 depicts stearic acid microspheres prepared in 5 mM HEPES buffer at pH 7.0 at 50× and 100×.
Figure 2:
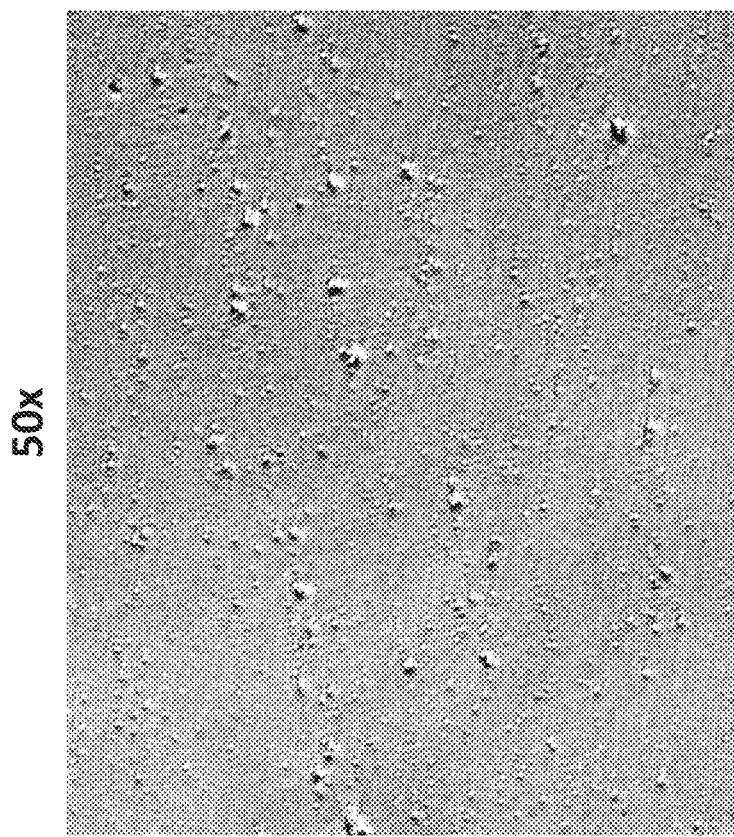
Figure 3:
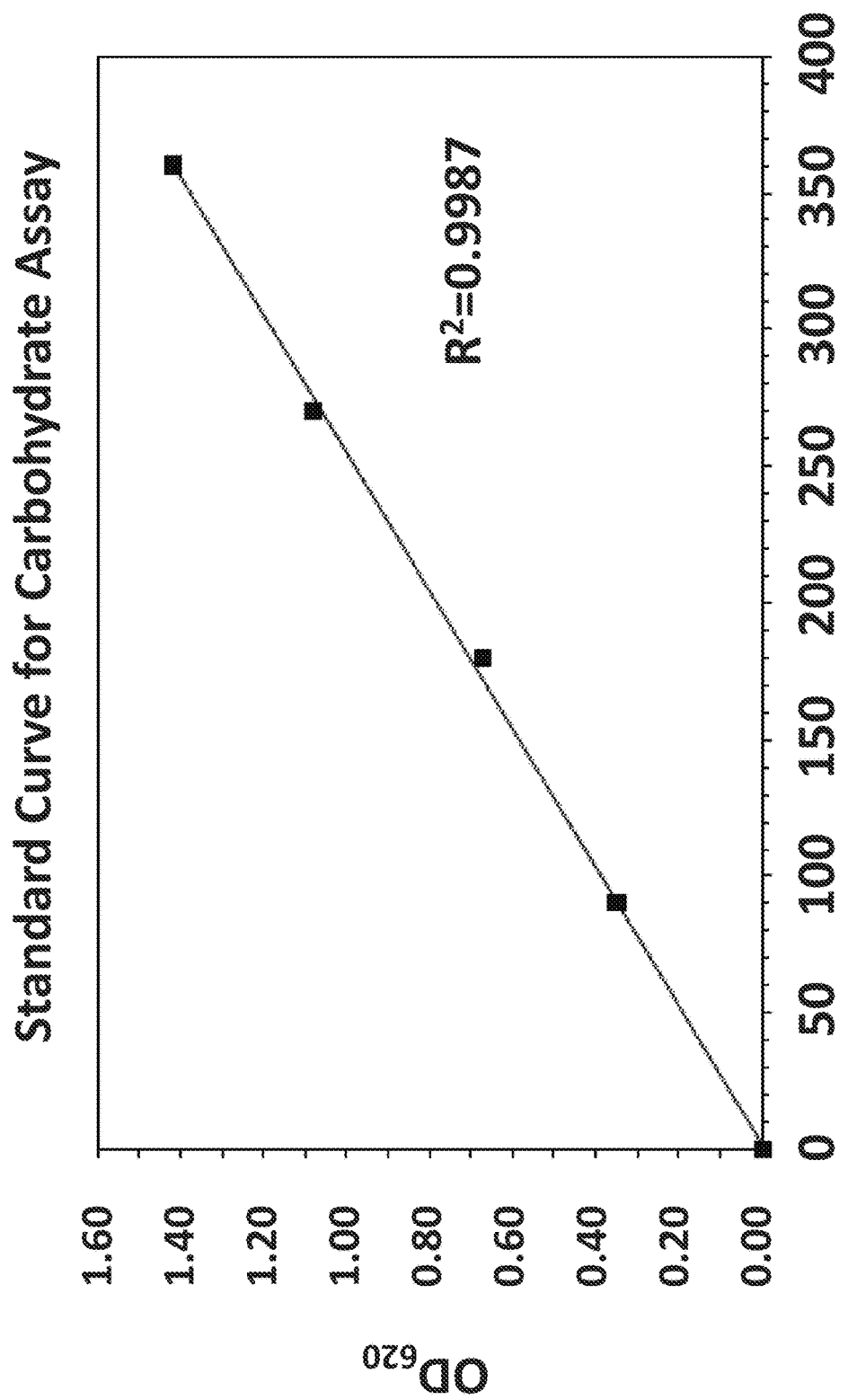
FIG. 3 depicts a representative standard curve of SOA. The anthrone reaction was assayed in 13.5 M sulfuric acid and heated for 11 min at 100° C. Samples were cooled on ice, centrifuged, and absorbance readings were obtained at 620 nm for generation of a standard curve, and for identifying SOA content of dissolved microspheres.

Stearic acid microspheres were prepared by the hot-melt encapsulation method at a weight ratio of 5.5:1 stearic acid to SOA. Stearic acid and SOA were melted at a temperature of 90° C., mixed, and poured into a rapidly stirred solution of HEPES buffer at pH 8.0 that was warmed to 50° C. After cooling the solution, the microspheres were separated by centrifugation at 7,000 to 10,000 g, collected by vacuum filtration, and dried. The resulting microspheres varied in size from 100-500 μmeters in diameter (FIG. 2). Colorimetric analysis of SOA content by the anthrone assay showed that weight ratios of stearic acid to SOA in dried microspheres ranged from 12:1 to >15:1 with a median weight ratio of 50:1 (FIG. 3).

The loaded microspheres were then incorporated into edible thin films. Edible strips were prepared from stearic acid-SOA microspheres, pullulan, hydroxypropyl methylcellulose, xanthan gum, glycerol, mannitol, sucralose, TBHQ, and peppermint oil. Films were dried overnight at room temperature, cut into one-inch squares, and stored at 4° C. until use. Each one-inch square strip contained approximately 3.6 mg of loaded microspheres. Light microscopy studies indicated that microspheres were evenly distributed in dried films.

For edible strips composed of pullulan and HPMC, 5 mg/ml of microspheres was chosen for the stock solutions. For one-inch square edible strips, approximately 0.4 mg of the bitter taste stimulus quinine is placed in strips (which corresponds to 0.75 ml of film solution). The size and thickness of strips can be varied to increase the amount of encapsulated quinine. In addition, more microspheres can be added during the formation of edible strips to increase the delivery of a molecule to the oral cavity.

Control taste strips (3.0% polymer content with a pullulan and HPMC film base only) that measured 2.54 cm×2.54 cm in size weighed on average 20.6 mg, and had an average film thickness of 0.03 mm. Microsphere-containing strips are composed of 3.6% polymer, and may be a bit thicker than our original strips (3% polymer).

To study the effect of encapsulating SOA on the taste of SOA, psychophysical studies were carried out. Taste intensity and taste quality studies were then examined as a function of time in order to determine the efficacy of microsphere-containing edible taste strips in minimizing and delaying the bitter taste of SOA in the human oral cavity. A total of 30 healthy volunteers participated, and their ages ranged from 18 to 65. The average age of test subjects was 21.7±1.5 years. 40% of study participants were males. 70.0% of subjects were Asian, 20% were Caucasian, 3.3% were Black/African-American, and 6.7% were of Hispanic descent. 28 of 30 participants were non-smokers. Subjects were asked to refrain from eating or drinking for 30 minutes prior to testing sessions. Subjects with diabetes, neurological disorders, or subjects who had recent dental visits, were excluded from this study. The general Labeled Magnitude Scale (gLMS) was used for intensity measurements, and a modified hedonics scale (−100 to +100) was used for pleasantness. Taste quality responses were chosen from sweet, salty, sour, bitter, and no taste.

Figure 4:
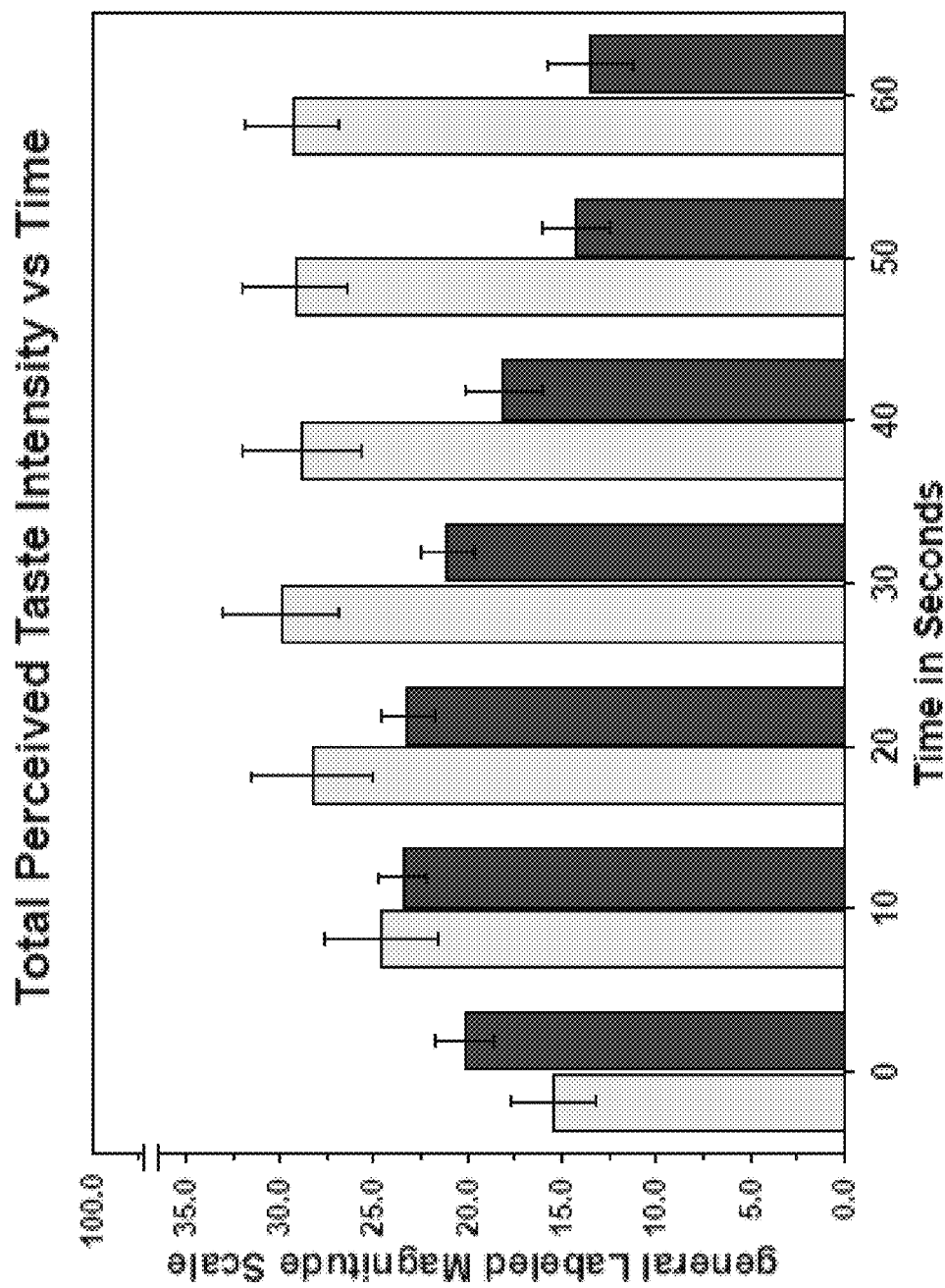
FIG. 4 depicts the perceived taste intensity as a function of time after taste strip dissolved on the roof of the mouth. Light blue bars represent SOA taste strips, and gray bars represent SOA-microsphere taste strips that contained an identical amount of SOA. Microsphere strips also contained several sweet taste stimuli and peppermint oil. Standard errors are shown as black vertical lines (n=12 test subjects).
Figure 5:
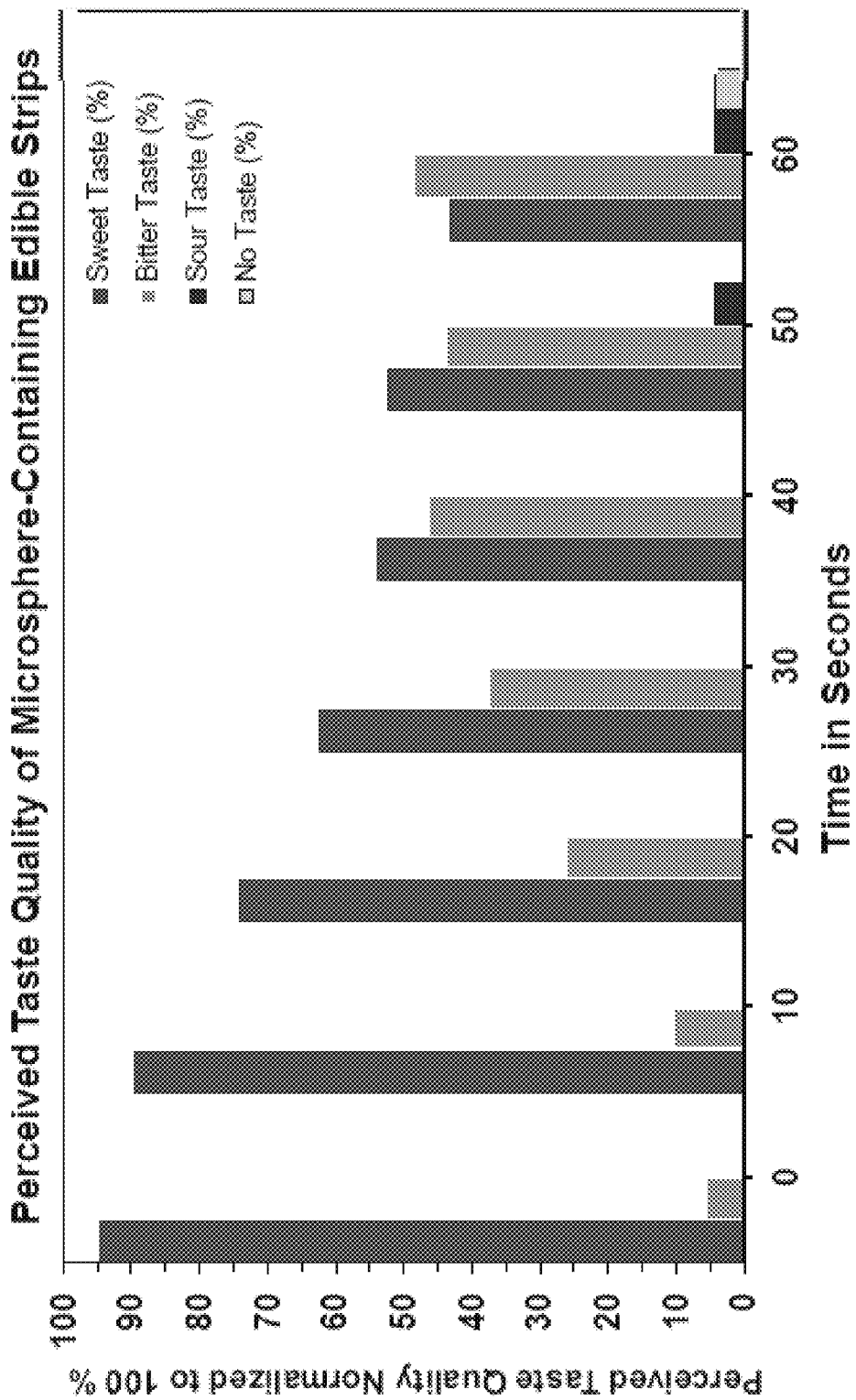
FIG. 5 depicts the perceived taste qualities of SOA-microsphere strips. Subjects chose from the four primary taste stimuli along with no discernible taste. The general Labeled Magnitude scale was used to quantify perceived taste qualities at each time point. Red, blue, dark blue, or gray bars represent individual primary taste qualities, or no perceived taste (n=12).
Figure 6:
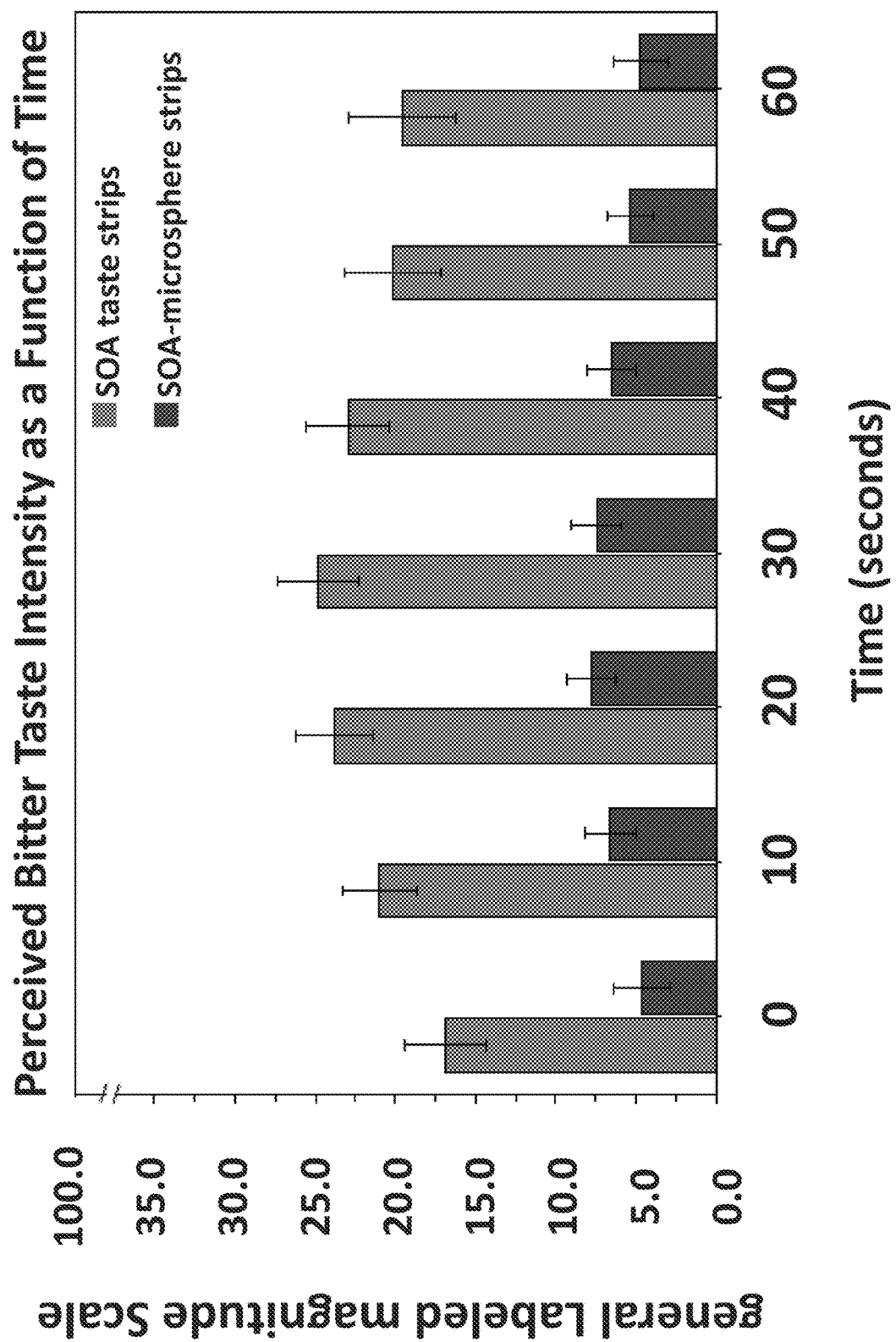
FIG. 6 depicts the perceived bitter taste intensity of SOA taste strips and SOA-microsphere taste strips that also included sweet taste stimuli. Teal bars represent mean bitter taste intensity of SOA taste strips, and purple bars represent mean taste intensity of SOA-microsphere strips. Standard errors are shown as black vertical lines (n=25).
Figure 7:
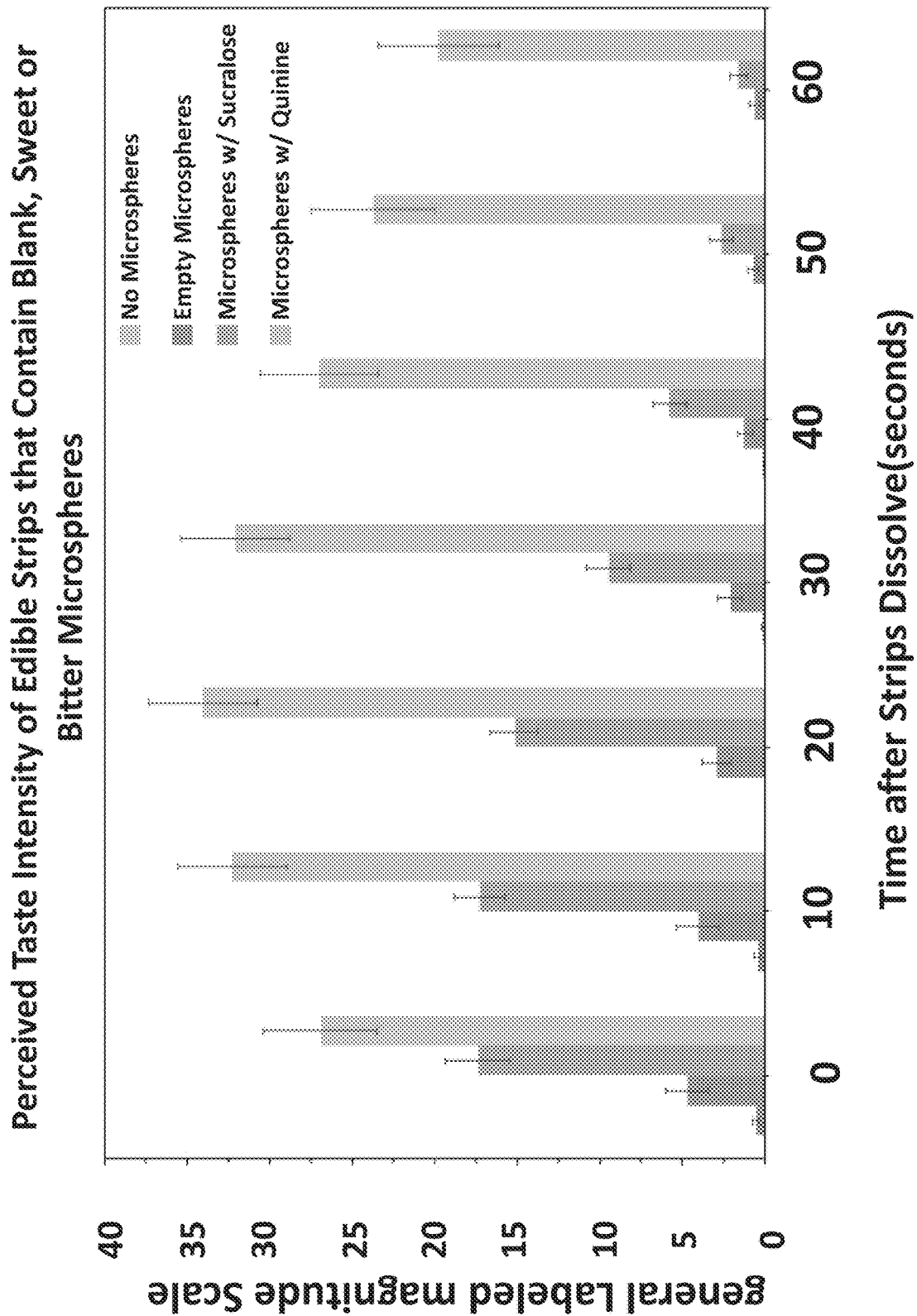
FIG. 7 depicts the taste intensity of edible strips alone (strips composed of the polymers pullulan and hydroxypropyl methylcellulose), edible strips with blank (empty) microspheres, quinine-containing microspheres (bitter taste), and sucralose-containing (sweet taste) microspheres.
Figure 8:
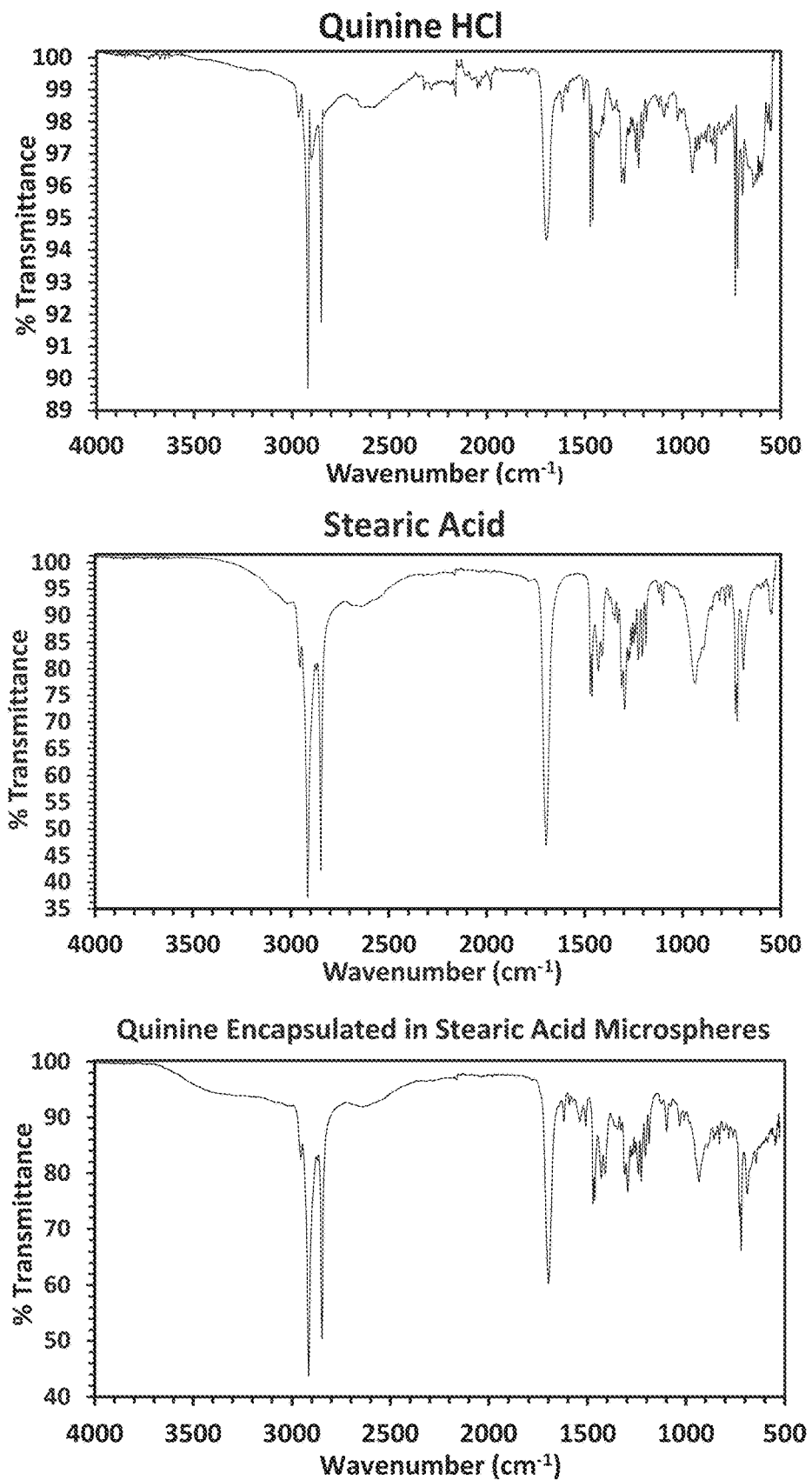
FIG. 8 depicts the IR spectra of quinine HCl alone, stearic acid alone, and quinine HCl microspheres.

The psychophysical studies demonstrated that encapsulating SOA, and suppressing the bitter taste of SOA with sucralose, decreased gLMS bitter taste intensity values by approx. 40% when compared to control strips that contained only unencapsulated SOA (FIGS. 4 and 5). Further, the microsphere-containing taste strips delayed the onset of bitter taste by approximately 15 seconds in our subject population (FIG. 6). The sucralose strip with SOA microspheres had a significantly improved mean hedonic rating compared to strips with SOA only (Table 1). This novel approach successfully diminishes the bitter taste of SOA, and is a promising method for delivering bitter tasting drugs to young children and elderly individuals.

TABLE 1

Mean hedonic ratings

| Edible Taste Strip | Mean Hedonic Rating |
|---|---|
| Sucralose Strip with SOA Microspheres | 4.8 |
| Strip with SOA Only | −24.1 |
| Control Strips | 0.0 |

Mean hedonic ratings are shown for edible strips that contained stearic acid-SOA microspheres and sweet taste stimuli, taste strips with SOA only (no microspheres), and control taste strips (n = 12). Hedonic scale ranged from −100 to +100 with 0 representing neither like or dislike.

The results presented herein demonstrate that the bitter taste stimuli sucrose octaacetate (SOA), n-propylthiouracil (PROP), phenylthiocarbamide (PTC) and quinine HCl can be successfully encapsulated within stearic acid microspheres by the holt-melt procedure. Edible taste strips with SOA-containing microspheres were successfully prepared. SOA content in microspheres was assayed by the anthrone reaction. Microspheres contained from 41 to 73 milligrams of stearic acid per milligram of SOA (wt/wt). Median wt/wt ratio of stearic acid to SOA in microspheres was ~50.1. The bitter taste of SOA was suppressed by approx. 75% in SOA microsphere-containing strips that also contained sucralose, mannitol, and peppermint oil. The bitter taste of SOA was delayed in SOA microsphere-containing strips that also contained sucralose, mannitol, and peppermint oil for minimizing bitter taste.

Compounds other than stearic acid, such as elaidic acid, Carnauba wax (palm wax), or Compritol® 888 ATO, can be used to encapsulate compounds. Further, microspheres can be prepared from mixtures of lipid components with melting points above 40° C.

Example 2: Incorporation of Sucralose into Stearic Acid Microspheres

As described elsewhere herein, bitter taste stimuli quinine HCl, n-propylthiouracil (PROP), phenylthiouracil (PTC), and sucrose octaacetate (SOA) have each been incorporated into stearic acid microspheres. By altering pH during microsphere formation, the sweet taste stimulus sucralose can be incorporated within stearic acid microspheres. As described in Example 1, the bitter taste of SOA is delayed in microsphere-containing taste strips. Therefore, it is important to further minimize bitter taste by adding sucralose containing microspheres within the edible materials. The delayed and prolonged release of sucralose from microspheres will coincide with the delayed release of SOA from microspheres, which will further minimize bitter taste in these edible strips. This novel approach diminishes the bitter taste of SOA release stimuli in the oral cavity.

The incorporation of the non-caloric sweetener sucralose is noteworthy because this compound is difficult to incorporate into microspheres. Sucralose was encapsulated within stearic acid microspheres by lowering the pH of the aqueous buffer solution to 4.15, and by melting the sucralose at a temperature just below the temperature at which it degrades (~115° C.). At this pH, the carboxyl group of stearic acid is fully protonated and neutral, and may allow incorporation of polar compounds such as sucralose. No encapsulation of sucralose is observed at pH 8.0, which is used to encapsulate bitter taste stimuli.

The hot melt method was used to prepare sucralose-loaded microspheres. Briefly, the sucralose and stearic acid are melted together at high temperature, mixed, and then poured into a rapidly stirred solution of buffer at 55° to 60° C., and cooled. The resulting microspheres are precipitated by centrifugation, collected by vacuum filtration, washed with buffer, and finally washed with sterile water. Microspheres are dried overnight in a vacuum oven just above room temperature, or on the lab bench in the dark at room temperature. The dried microspheres are stored at 4° C. until use.

Bitter taste stimuli are prepared in a similar manner, except at a pH of 8.0. Along with stearic acid, SOA is melted at ~100° C., quinine HCl·7H$_2$O is melted at ~165° C., quinine HCl·2H$_2$O is melted at 116° C., or n-propylthiouracil (PROP) is melted at ~150° C. before addition to a rapidly stirred buffer solution. IR spectra of PROP, quinine, sucralose, and SOA encapsulated microspheres showed that not components were graded during microsphere formation and storage. Quinine content of microspheres is measured by fluorescence emission or by absorbance in the ultra-violet region. SOA content of microspheres is measured by the anthrone reaction, and PROP and PTC content of microspheres is measured by UV absorption at 275 nanometers.

Encapsulated SOA was then incorporated into edible taste films that contained the sweet taste stimuli sucralose, glycerol, and mannitol along with peppermint oil in order to block the (delayed) bitter taste of SOA from microspheres. Edible taste strips were prepared by dissolving the polymers pullulan and hydroxypropyl methylcellulose in hot water, cooling the solution, and adding various taste and trigeminal stimuli. The solution was then poured onto non-stick surfaces, dried overnight at room temperature, and cut into one-inch squares.

The sweet taste stimuli in the edible taste strip, sucralose, glycerol, and mannitol, are released from strips when the strips initially dissolve in the oral cavity (i.e., as soon as the strips come in contact with saliva). The addition of 0.004% (v/v) peppermint oil further masked the bitter taste of SOA in the strips. The bitter taste of SOA was decreased by approximately 75% in edible taste strips that contained sucralose, glycerol, mannitol, and peppermint oil in the film base. Sucralose content of microspheres is measured by oxidation of KMnO4 at 610 nanometers.

Edible taste strips can also contain sucralose-containing microspheres and SOA-containing microspheres. These edible taste strips are composed of the polymers pullulan and hydroxypropyl methylcellulose, along with xanthan gum, to prepare the film base. The polymer solution is prepared, sweet taste stimuli are added, peppermint oil is added, and solid microspheres are finally added to the polymer solution. The mixture is briefly sonicated (4 times at fifteen seconds) then poured onto large weigh boats, and allowed to dry overnight at room temperature. The resulting films are then removed from the weigh boat, and cut into one-inch squares. In these rapidly dissolving strips, sucralose is both a component of edible taste films, and is also encapsulated within microspheres. Unencapsulated sucralose is released as soon as the taste strips dissolve in the oral cavity. However, the release of encapsulated sucralose is delayed and is released from microspheres concomitant with the release of bitter taste stimuli from microspheres that only contain a bitter taste stimulus. This delay in the release of sucralose from microspheres essentially eliminates the bitter taste of SOA or quinine HCl in the strips. Please note that sucralose and SOA or quinine microspheres are prepared at different pH values and therefore cannot be prepared together within microspheres.

Example 3: Incorporation of Stearic Acid Microspheres into Edible Formulations

One promising mechanism to overcome the limitations of bitter tasting drugs that are delivered as gels or capsules is the incorporation of bitter tasting drugs within stearic acid microspheres, and then incorporating these microspheres into rapidly dissolving edible strips that contain sweet taste stimuli and peppermint oil that further minimize bitter taste. Alternatively, stearic acid microspheres may be incorporated into chocolate or gelatin-based candies (i.e., gummy bears) for minimizing bitter taste. Microspheres can also be incorporated into sugar-free candies. Stearic acid is an excellent molecule for encapsulating molecules because this saturated lipid has no taste (Ebba et al., Physiol Behav. 2012, 106(5): 579-86.)

As described elsewhere herein, bitter taste stimuli quinine HCl, n-propylthiouracil (PROP), phenylthiocarbamide (PTC) or sucrose octaacetate (SOA) have been incorporated into stearic acid microspheres. The weight ratio of stearic acid to quinine ranged from 10:1 to 20:1. Stearic acid to SOA weight ratios ranged from 30:1 to 60:1. As described elsewhere herein, by lowering the pH during microsphere formation, the sweet taste stimulus sucralose can be encapsulated within stearic acid microspheres. Zingerone (ginger sensation which is a trigeminal stimulant), ethyl vanillin (artificial vanilla), and the NSAID drug ibuprofen are also encapsulated within microspheres at pH 7 to 8.

Stearic acid microspheres may be incorporated into gelatin-based candies. 5 milligrams of microspheres are incorporated into a small candy mold that is one milliliter in volume. With a typical weight ratio of 10:1 stearic acid to encapsulated quinine, approximately 0.5 milligrams of quinine can be readily incorporated into a small candy mold. Significantly more microspheres can be incorporated into small candy pieces without stimulating bitter taste compared to edible taste strips.

In addition to edible films and candies, bitter taste stimuli-containing microspheres can be incorporated within white and dark chocolate candy. Larger candy molds (9 ml volume) allow considerably more loaded microspheres to be incorporated into chocolate candy than can be incorporated into gelatin candies or edible taste strips. During consumption of microsphere-containing candy, no bitter taste perception from the exemplary bitter stimuli quinine was noted when either blank (empty) microspheres or quinine-containing microspheres were used. Visual inspection has indicated that microspheres are uniformly distributed in chocolate candies. As with edible films, microsphere-containing candies can be prepared in a variety of shapes and sizes. Ice cream, pudding, apple sauce, or yogurt may also be used as alternative vehicles to deliver stearic acid microspheres loaded with drugs.

Example 4: Microscopy Studies of Microspheres and Taste Strips

Figure 9:
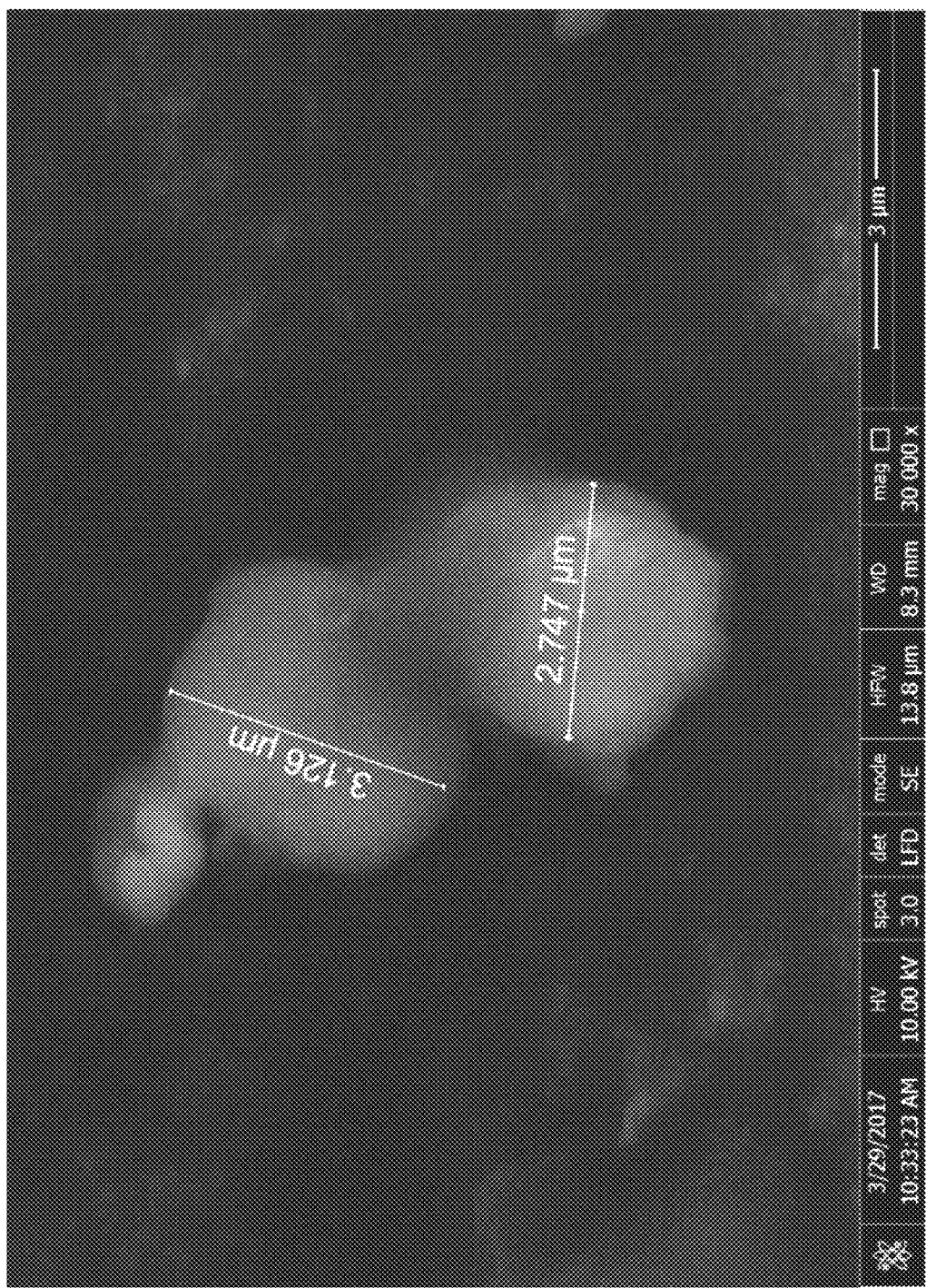
FIG. 9 depicts an SEM image of Quinine HCl microspheres at 30,000× magnification.
Figure 10:
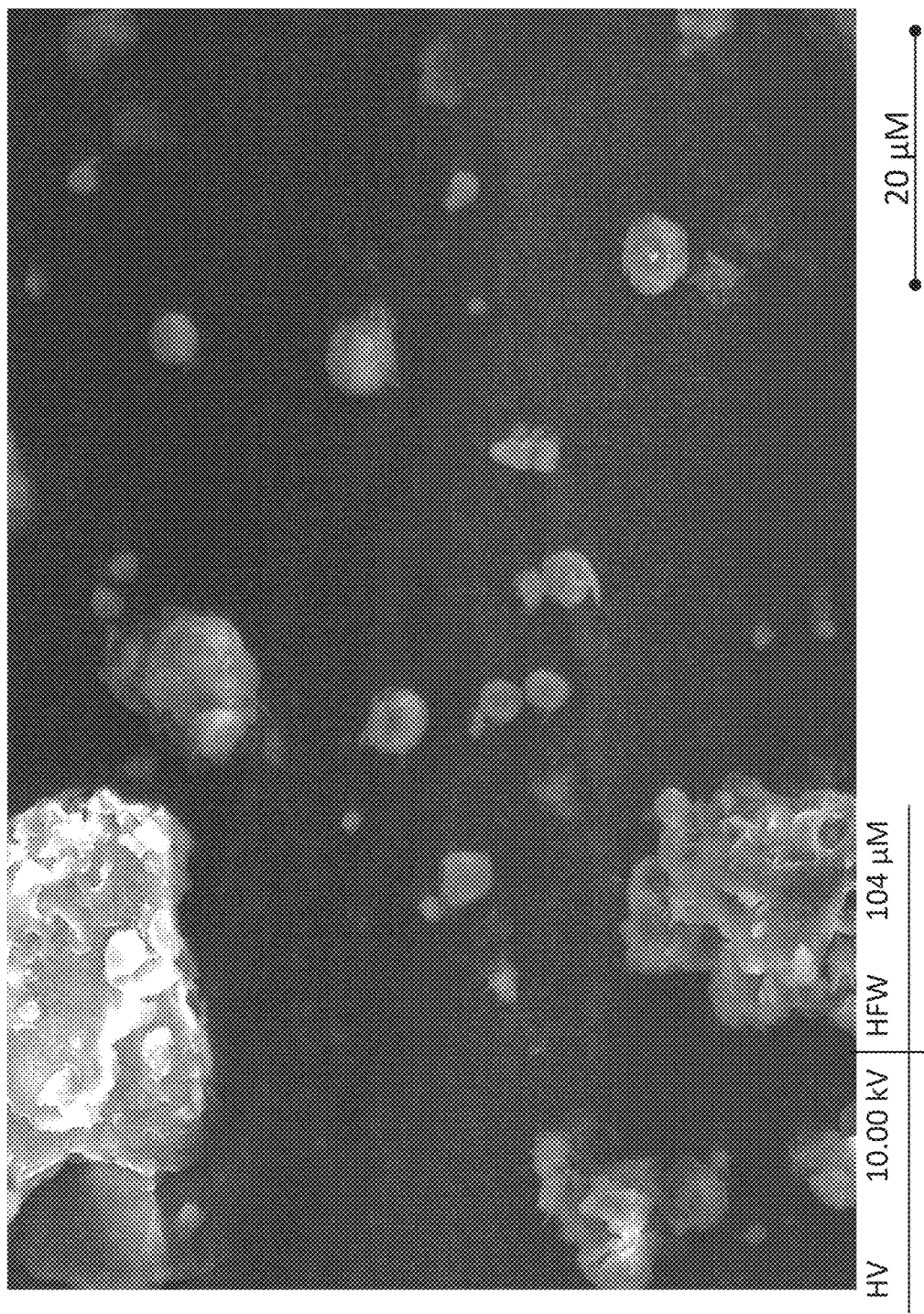
FIG. 10 depicts an SEM image of Quinine HCl microspheres at 4,000× magnification.

The size and shape of microspheres directly affect their ability to encapsulate a drug. In order to identify the size and shape of microspheres, scanning electron microscopy (SEM) studies of encapsulated microspheres were undertaken. Microspheres were imaged with an FEI Quanta 450FEG SEM equipped with an Energy Dispersive Spectrometer (Oxford Aztec Energy Advanced EDS System). Scanning electron microscopy studies were conducted on stearic acid microspheres that contained either the bitter taste stimulus quinine HCl·2H$_2$O, or sucralose octaacetate. Microspheres were analyzed for their shape, size, and surface structure. Overall, quinine-containing microspheres were round in shape, with an average size of approximately 3 microns in diameter (FIG. 9). With encapsulated quinine HCl, microspheres exhibited a smooth, rounded surface. These microspheres also formed clusters when the microspheres were air dried (FIGS. 9-10).

Figure 11:
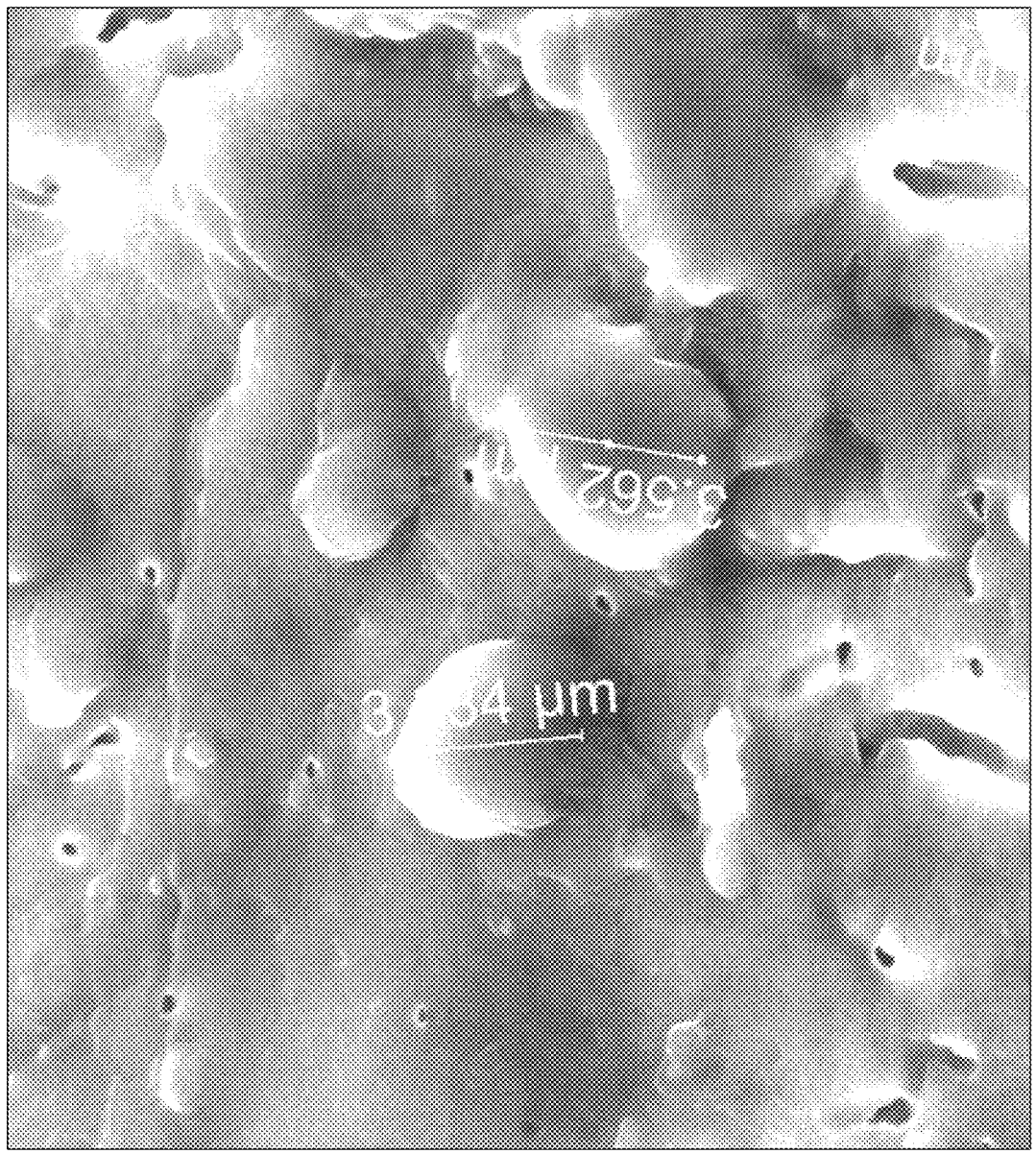
FIG. 11 depicts an SEM image of SOA microspheres at 10,000× magnification.

Microspheres that contained the more polar sucralose octaacetate showed less of a rounded structure, and were more crystalline in shape. These structures appeared to form larger amorphous crystals in the microscope (FIG. 11).

Example 5: The Effect of Small Amounts of Additional Lipids to the Melting Point of Stearic Acid Microspheres In order to more readily release the contents of loaded microspheres that contain drugs, compounds for release into the environment, or bitter taste stimuli into the oral cavity, a melting point range that is high enough to maintain the integrity of microspheres at room temperature, but low enough to readily release its contents in the human oral cavity (or into the environment) would be ideal. The importance of lowering the melting point of microspheres would allow a more controlled and more efficient release of encapsulated compounds into the oral cavity for drug delivery, or for the release of herbicides or pesticides into the environment.

While not wishing to be bound to any particular theory, the presence of impurities (small amounts of additional lipids) in a solid substance may cause the melting point of that substance to occur at a lower temperature by the process of melting point depression. This concept was used to modify (decrease) the melting point of stearic acid microspheres. In order to achieve this effect, the effects of lipid compounds on lowering the melting point of stearic acid microspheres was examined.

Pure stearic acid melts at 69.3° C. (Merck Index). Stearic acid microspheres that contain no encapsulated compounds and are produced by the "hot melt" method, generally show a melting point range of 55-60° C. The effect of small amounts of linoleic acid, cocoa butter, saponin, and coconut oil on the melting point of stearic acid microspheres was identified.

Linoleic acid is an 18-carbon cis-unsaturated fatty acid, and this lipid is an essential fatty acid. Fifty microliters (45.1 µg) of linoleic acid (67% linoleic acid-33% oleic acid mixture from Sigma Chemical Co.) was added to 1.0 g of stearic acid in order to prepare stearic acid microspheres. At this ratio, linoleic acid lowered the melting point of microspheres to 47-52° C. Then, 100 µliters (90.2 micrograms) of 67% linoleic acid was added to 1.0 gram of stearic acid in order to prepare microspheres by the hot melt method. The resulting microspheres melted at a slightly lower range, which was 45-48° C.

Cocoa butter also affected the melting point of stearic acid microspheres. At a 10:1 weight:weight ratio of stearic acid a cocoa butter, the resulting melting point of microspheres ranged from 38-44° C.

Coconut oil is an edible oil that is extracted from coconuts harvested from the coconut palm. Coconut oil has a high content of saturated fats (~90%), and is slow to oxidize in air. The main component of coconut oil is the medium-chain saturated fatty acid lauric acid (12 carbons). One advantage of this compound is that coconut oil exhibits minimal taste qualities. At the present time, coconut oil has not been used to modify the melting point of lipid microspheres.

At a weight ratio of 15:1 (60 µl of coconut oil) to 1.0 gram of stearic acid, the resulting microspheres melted in the range of 37-45° C. When stearic acid-coconut oil microspheres were used to encapsulate quinine HCl, the melting point remained essentially unchanged and ranged from 39-44° C. When stearic acid-coconut oil microspheres were used to encapsulate the lipophilic herbicide 2,4-dinitrophenol, the resulting melting point of microspheres was lowered to 36-45° C.

Similar results were obtained with the amphipathic glycoside saponin that was purified from the bark of the *Quillaja* tree (Sigma Chemical Co.). Saponins are promoted for use as dietary supplements and food additive. At a weight ratio of 67:1 stearic acid to *Quillaja* saponin, the resulting microspheres melted in the range of 45-54° C.

Taken together, these results indicate that the addition of small amounts of lipids or glycosides to stearic acid during microsphere formation by the hot melt method can lower the melting point of lipid microspheres to approximately 40-45° C. Since coconut oil exhibits essentially no taste and is widely used in cooking, we propose to include small amounts of coconut oil to decrease the melting point of stearic acid microspheres for the controlled and efficient release of loaded compounds from microspheres (i.e., drugs, taste stimuli, herbicides, or pesticides). These microspheres would then be incorporated into edible strips, or used directly for the release of encapsulated compounds.

Example 6: Preparing Microsphere-Containing Edible Strips

When microspheres are added to the pullulan-mannitol-glycerol-xanthan gum peppermint aqueous base for preparing microsphere-containing edible strips, these microspheres routinely adhere to the wall of the test tube that is used to pour the solution onto a non-stick surface. This is overcome by simply wiping the sides of a non-stick container or a plastic 50 ml conical test tube with coconut oil, and allowing the surface to dry. These non-stick surfaces almost completely diminish microsphere adherence to containers during edible film preparation.

Further, the amount of sucralose in the microspheres can be quantified. Until recently, the amount of sucralose encapsulated into microspheres was identified simply by tasting dried microspheres before they are incorporated into edible strips. However, it is described herein the amount of sucralose in microspheres can be successfully quantified by assaying the microspheres in a basic (50 mM NaOH) solution of 1.65 mM $KMnO_4$ (modified from Yousef et. al., Drug Test and Analysis, 2010). After centrifugation to remove the stearic acid precipitate, the resulting manganite-$MnO_2$ product is assayed at 610 nm in a single-beam spectrophotometer.

Figure 12:
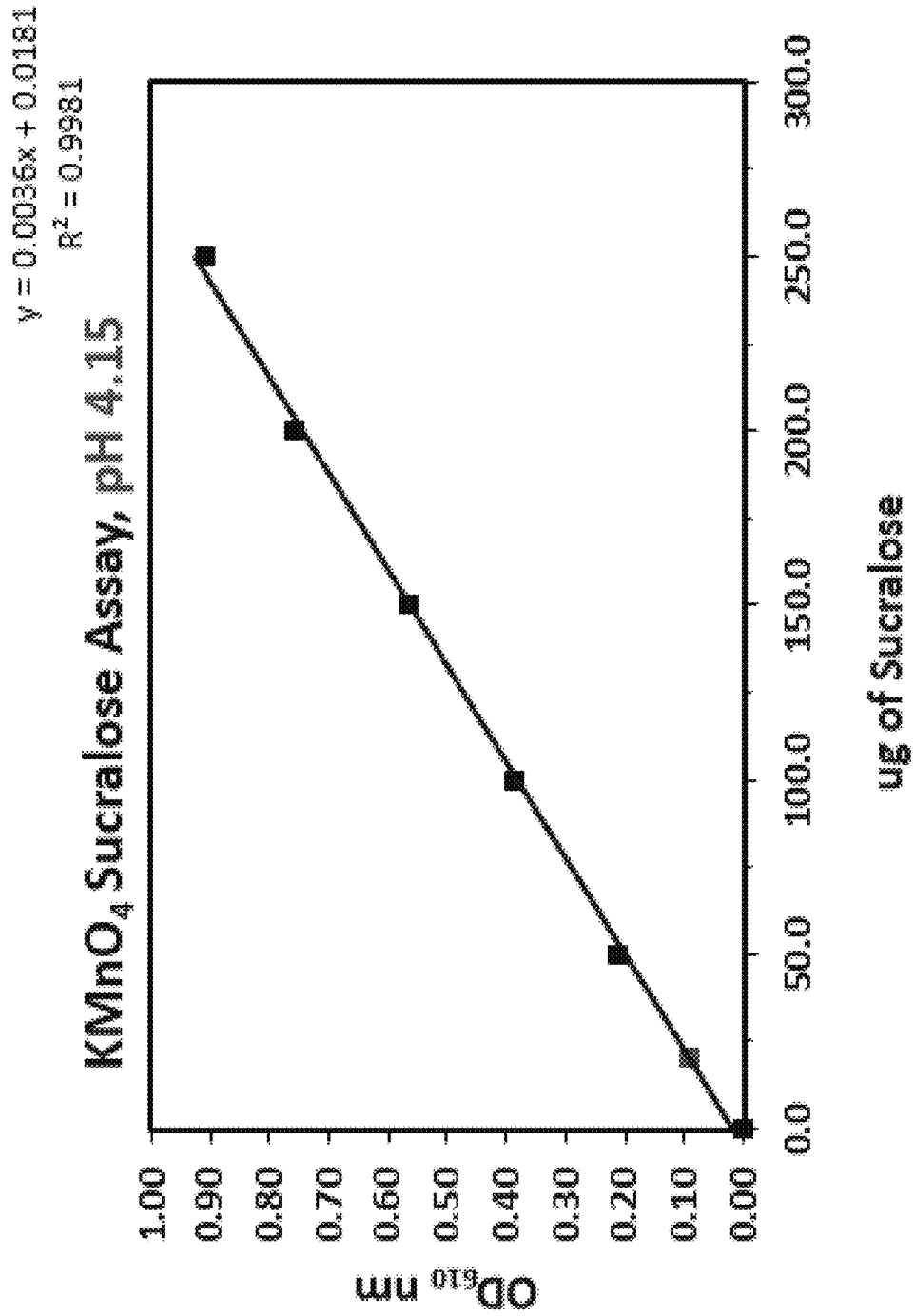
FIG. 12 depicts a graph quantifying the amount of sucralose in the microspheres.

FIG. 12 demonstrates the determination of amount of sucralose in microspheres. The red square in the FIG. 12 represents the unknown (sucralose microspheres). Three different sucralose-containing microspheres were assayed and wt:wt ratios were obtained of 40-50:1 stearic acid to sucralose when microspheres are prepared at pH 4.15. These encapsulation ratios are higher (less encapsulation) than those obtained with more lipophilic compounds such as quinine HCl or the herbicide DCMU. However, sucralose is approximately 600 times sweeter than sucrose, and even small amounts of incorporation of this sweet taste stimulus will allow a slightly delayed release of sucralose (and delayed sweet taste perception) from these microspheres to counteract the delayed release of bitter taste stimuli from microspheres. In addition, this is the first report of successful encapsulation of sucralose in lipid microspheres. This improvement will allow for more precise control the ratios of sucralose and bitter tasting compounds in microspheres for incorporation into edible strips and films.

Further, the microsphere yield can be increased. Microspheres are isolated by first centrifuging the mixture at 10,000 g at 15° C. for 10 minutes. A centrifugation step minimizes the loss of microspheres that are lost by excessive vacuum filtration. The precipitated microspheres are then placed on filter paper, and washed by vacuum filtration with HEPES or sodium acetate buffer, again washed with buffer, and finally washed with 2 mM potassium phosphate buffer at pH 7.0 rather than with water. The use of phosphate buffer at the last step decreases clumping of microspheres as they air-dry overnight.

Example 7: Psychophysical Testing of Microspheres that Contain the Bitter Tasting Compound Quinine HCl For human studies with taste strips that contain lipid microspheres, 200 milligrams of microspheres were mixed with 40 ml of taste strip solution, and poured onto a non-stick surface. After drying, the films with embedded microspheres are cut into 1"×1" taste strips. Previous studies have shown that a wt:wt ratio of 2:1 sweet taste stimulus to bitter taste stimulus in microspheres significantly blocks bitter taste response. (Humans are considerably more sensitive to bitter taste than to sweet taste). A 1"×1" taste strip also contains 750 nanomoles of sucralose, 2.5 nanomoles of mannitol, 65 nanomoles of glycerol, and 2.16 mg of peppermint oil flavoring in a 3.5% pullulan-hydroxypropyl cellulose film base. This amount of peppermint oil is the maximal amount that will not phase separate as the solution dries to a thin film.

Test subjects were asked to rate taste intensity if a taste is detected, and to identify up to two taste qualities per strip (sweet, bitter, other taste, or no taste) at 10 second intervals over a span of 80 or 120 seconds for each taste strip. This study is approved by Temple U., IRB Protocol #4540. For experiment 1, this study contained edible taste strips with empty (blank) microspheres, and this control identified possible tactile responses that might arise from microspheres (Trial 1 in Table 2). A second experiment contained strips with quinine HCl and control microspheres at a weight ratio of 1:2 quinine to control microspheres (Trial 3 in Table 2). A third experiment contained both quinine and sucralose microspheres at a 1:2 weight ratio of quinine to sucralose microspheres in strips (Trial 5 in Table 2). Finally, a fourth experiment contained edible taste strips with no microspheres (Trial 6 in Table 2). All four different experiments contained taste strips with peppermint oil, sucralose, mannitol, glycerol, and xanthan gum in the pullulan-hydroxypropyl methylcellulose film base. These strips only varied in their encapsulated microsphere content. In addition to taste intensity and taste quality measurements, this study examined the suppression of bitter taste of quinine HCl microspheres that are embedded in edible films. Table 2 describes the four different taste strips that were used in the first study.

TABLE 2

| Trial | Film Base | Microspheres |
|---|---|---|
| Trial 1 | Peppermint-Sucralose Film Base | Control (Blank) |
| Trial 3 | Peppermint-Sucralose Film Base | Quinine + Control |

TABLE 2-continued

| Trial | Film Base | Microspheres |
|---|---|---|
| Trial 5 | Peppermint-Sucralose Film Base | Quinine + Sucralose |
| Trial 6 | Peppermint-Sucralose Film Base | No Microspheres |

The perceived intensity axis represents taste intensities. Thus, the height of the vertical columns represents taste intensities at different time points after the strips dissolve. The taste intensity at each time point (column) is then broken down into taste quality (shown by changes in color), with taste quality identified as either sweet, bitter, other taste, or no taste. Thus, the height of the vertical bar identifies overall taste intensity, and the different colors in the bar represent the average proportions of taste quality responses of the participants. The same 15 participants participated in all four taste strip conditions.

Figure 13:
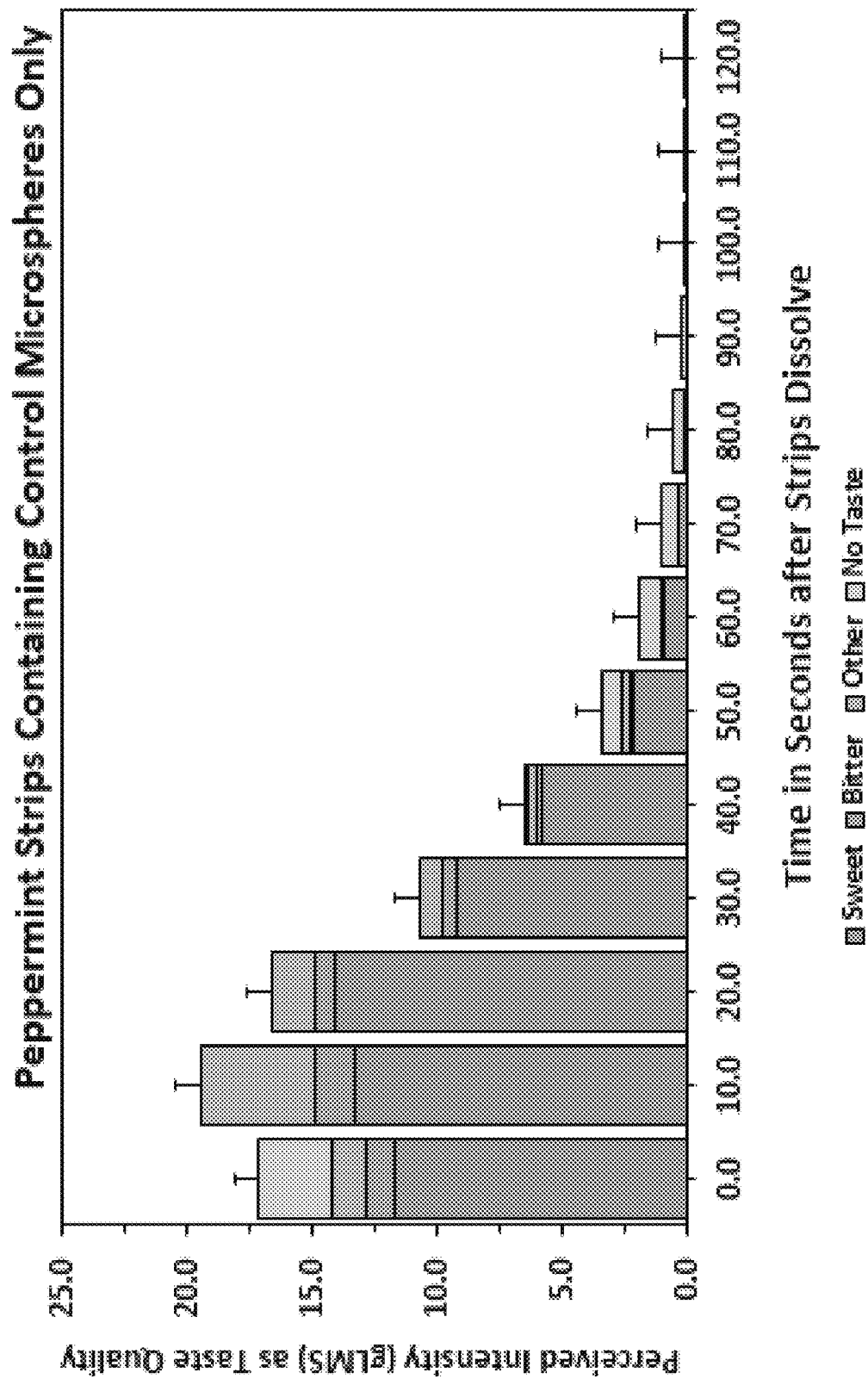
FIG. 13 depicts a graph demonstrating the overall taste intensity as a function of time in seconds after the strips dissolve in the oral cavity for trial 1, control (blank) microspheres.

Taste intensity measurements were identified by the general Labeled Magnitude Scale (gLMS), a widely-used scale for taste intensity measurements (Bartoshuk et al., 2004, *Physiology & Behavior*, 82: 109-114). As shown in FIG. 13, films that contained only control (blank) microspheres primarily exhibited a sweet taste (blue color) or no-taste quality (yellow color). Taste intensity measurements were initially in the moderate range of the gLMS scale, and dropped off rapidly after approximately 20 seconds as time increased to 120 seconds after the strips fully dissolved in the oral cavity. Finally, the ratio of sweet to bitter taste intensity for strips with control microspheres is shown below in Table 3.

TABLE 3

| | Control Microspheres Only | | | | | | | | | | | | |
|---|---|---|---|---|---|---|---|---|---|---|---|---|---|
| | Time (sec) | | | | | | | | | | | | |
| | 0 | 10 | 20 | 30 | 40 | 50 | 60 | 70 | 80 | 90 | 100 | 110 | 120 |
| Sweet:Bitter Ratio | 10.25 | 8.20 | 17.00 | 17.33 | 27.00 | 38.00 | 29.00 | 17.00 | 7.00 | 0.00 | 0.00 | 0.00 | 0.00 |

Figure 14:
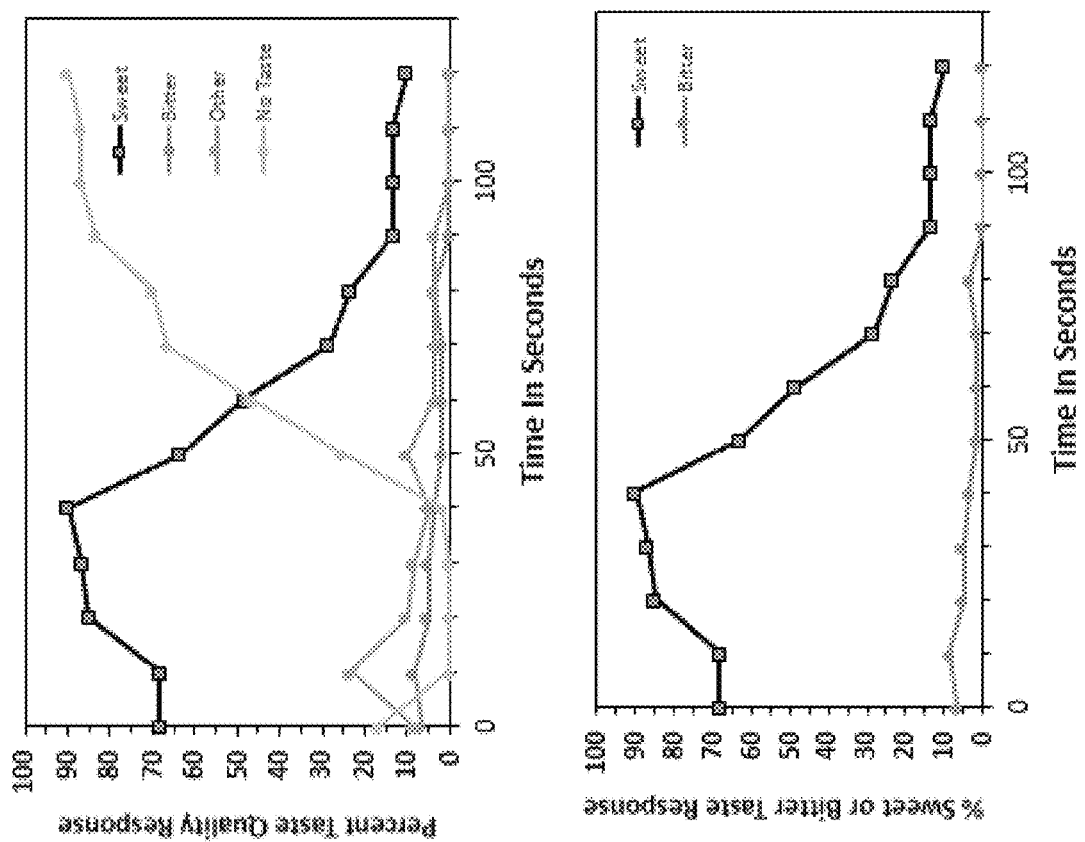
FIG. 14 depicts graphs demonstrating the proportion of taste quality responses (sweet, bitter, other taste, or no taste on the left, or sweet and bitter taste only on the right) as a function of time after the strips dissolve in the oral cavity for trial 1, control (blank) microspheres.

These strips showed a small bitter taste quality component in our population, and the sweet taste to bitter taste quality response averaged approximately 13.3:1 over 120 seconds (FIGS. 13-14). However, improvements in this technology have essentially removed the bitter taste component from control strips (see sucrose octaacetate taste study following this study).

Figure 15:
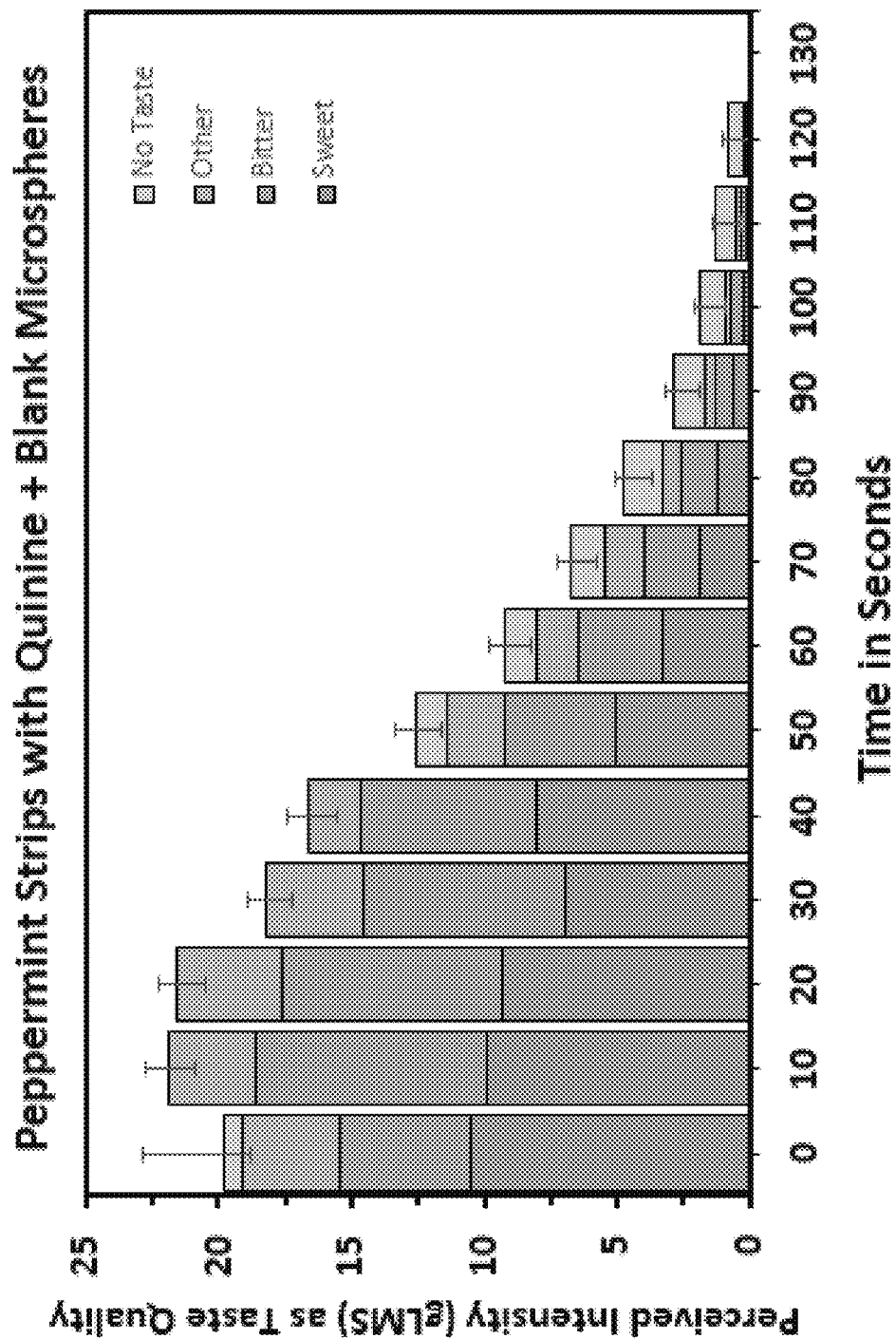
FIG. 15 depicts a graph demonstrating the overall taste intensity as a function of time in seconds after the strips dissolve in the oral cavity for trial 3, quinine and control (blank) microspheres (1:2 weight ratio of quinine to blank microspheres).
Figure 16:
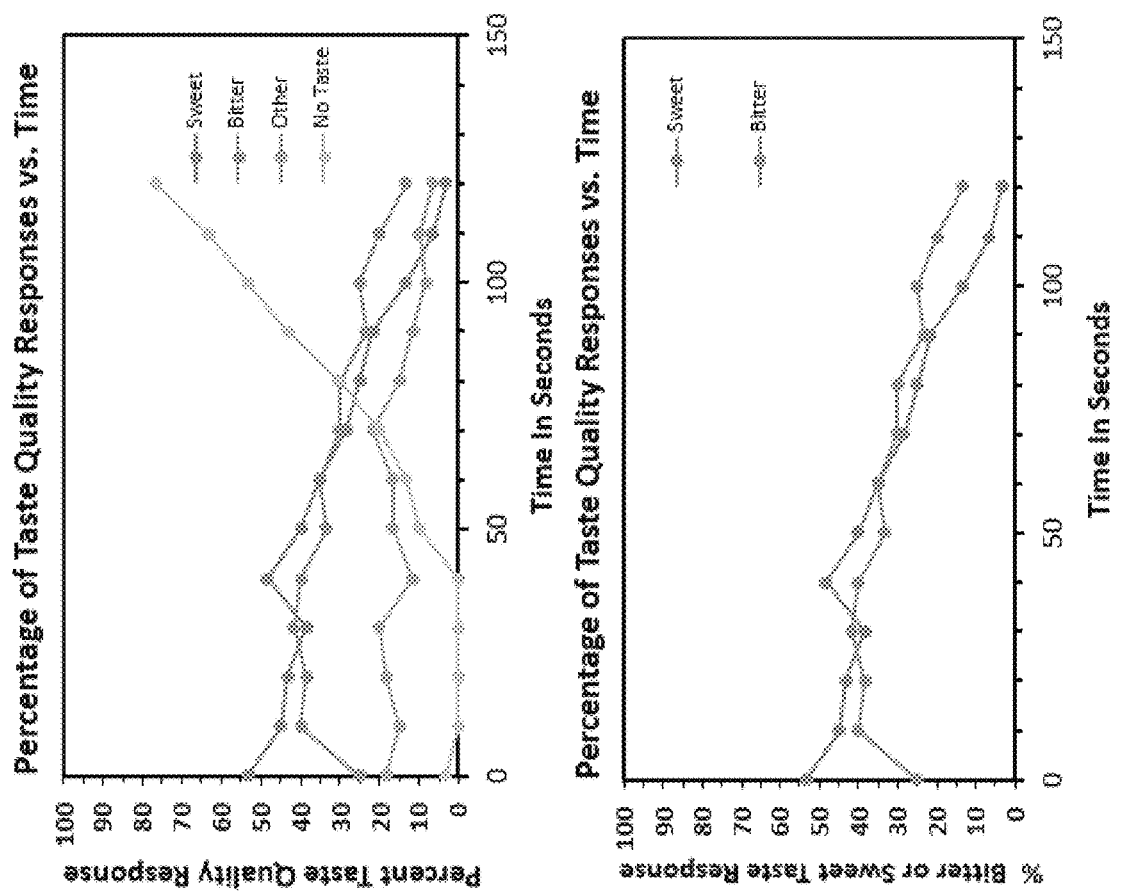
FIG. 16 depicts graphs demonstrating the proportion of taste quality responses (sweet, bitter, other taste, or no taste on the left, or sweet and bitter taste only on the right) as a function of time after the strips dissolve in the oral cavity for trial 3, quinine and control (blank) microspheres (1:2 weight ratio of quinine to blank microspheres).

The second experiment (Trial 3) examined both quinine HCl (bitter taste) and control (blank) microspheres in the peppermint film base. This study showed whether control microspheres could mitigate bitter taste. The overall taste intensity increased slightly over trial one, and was likely due to the addition of bitter-tasting microspheres to the edible strips. In addition, the decrease in overall taste intensity as a function of time was diminished when compared to trial one. However, the ratio of sweet taste response to bitter taste response were nearly equal over the 120 second time period (Table 4). Even when overall intensity decreased after 90 seconds, sweet taste quality responses nearly equaled the bitter taste quality responses. However, at longer times, the overall taste intensity (height of the bars in the graph) is a small number so that bitter taste is still diminished at extended times after the strips dissolve in the oral cavity (FIGS. 15-16).

TABLE 4

| | quinine + control microsphers | | | | | | | | | | | | |
|---|---|---|---|---|---|---|---|---|---|---|---|---|---|
| | Time (s) | | | | | | | | | | | | |
| | 0 | 10 | 20 | 30 | 40 | 50 | 60 | 70 | 80 | 90 | 100 | 110 | 120 |
| Sweet:Bitter Ratio | 2.13 | 1.13 | 1.13 | 0.92 | 1.21 | 1.20 | 1.00 | 0.94 | 0.83 | 0.93 | 0.53 | 0.33 | 0.25 |

The third experiment (Trial 5) examined the effect of both quinine HCl microspheres and sucralose microspheres embedded within edible strips. Overall taste intensity values (shown as column height in FIG. 17) as a function of time in seconds showed a similar pattern to that over trial 3 (quinine HCl and control microspheres). As shown in Table 5 below, the replacement of control microspheres with sucralose-containing microspheres increased the sweet to bitter taste quality ratios at all time points, and indicated that the addition of sucralose microspheres functioned to minimize the bitter taste response of quinine HCl in our test subjects. This effect of sucralose microspheres on taste increased as time increased. At time points greater than 90 seconds after these strips dissolved, the lingering bitter taste response was considerably lower than that of sweet taste responses. These results indicate that sucralose microspheres are critical for minimizing bitter taste responses from quinine-containing microspheres for up to two minutes after the strips dissolve in the oral cavity.

TABLE 5

| | Quinine + Sucralose Microspheres | | | | | | | | | | |
|---|---|---|---|---|---|---|---|---|---|---|---|
| | Time (s) | | | | | | | | | | |
| | 0 | 10 | 20 | 30 | 40 | 50 | 60 | 70 | 80 | 90 | 100 |
| Sweet:Bitter Ratio | 2.23 | 1.58 | 1.13 | 1.21 | 1.50 | 1.48 | 2.00 | 2.82 | 6.33 | 8.00 | 5.00 |

Figure 17:
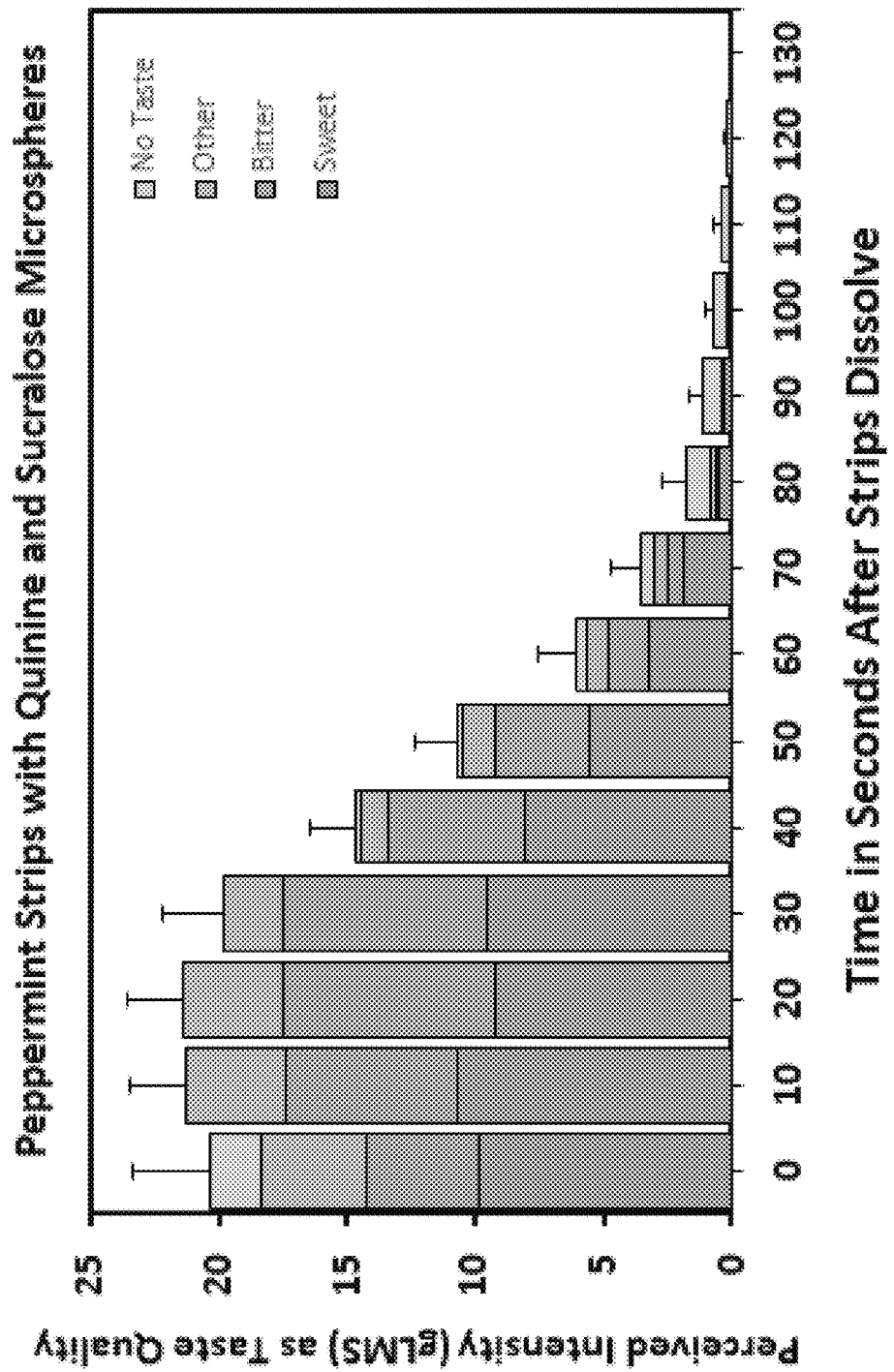
FIG. 17 depicts a graph demonstrating the overall taste intensity as a function of time in seconds after the strips dissolve in the oral cavity for trial 5, quinine HCl and sucralose microspheres (1:2 weight ratio of microspheres).
Figure 18:
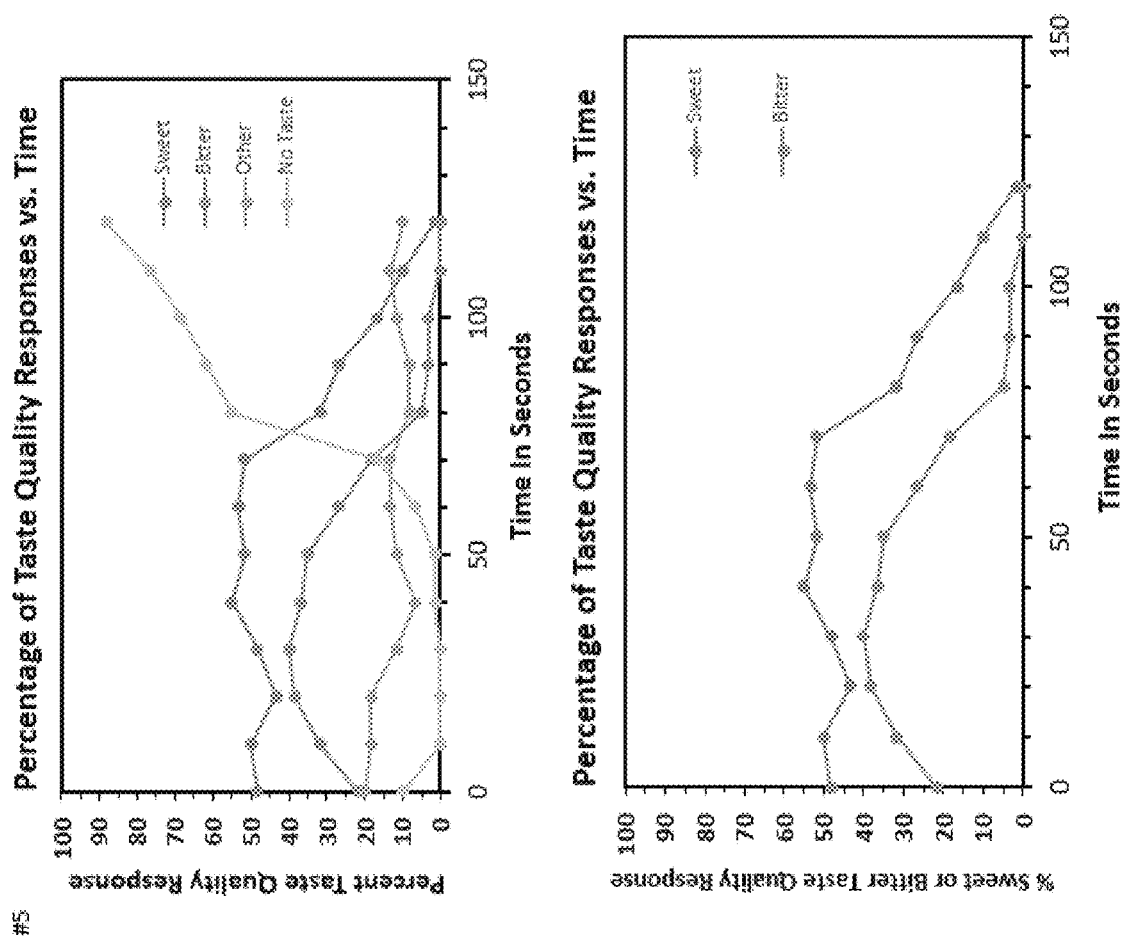
FIG. 18 depicts graphs demonstrating the proportion of taste quality responses (sweet, bitter, other taste, or no taste on the left, or sweet and bitter taste only on the right) as a function of time after the strips dissolve in the oral cavity for trial 5, quinine and sucralose microspheres (1:2 weight ratio of microspheres).

This experiment further demonstrates that sucralose microspheres diminished bitter taste responses in edible strips at time points greater than 60 seconds after the strips dissolve in the oral cavity (FIGS. 17-18). (The high ratios at times greater than 60 seconds is due to the fact that few subjects reported a bitter taste quality response at low intensities).

The numbers shown in Table 6 compare the sweet to bitter ratios of Trial 5 (quinine and sucralose microsphere strips) to Trial 3 (quinine and control microsphere strips) at identical time points from 0 to 100 seconds after strips dissolve. The replacement of control microspheres with sucralose microspheres caused a large increase in the sweet taste to bitter taste response when these two taste strips were directly compared.

TABLE 6

| | Comparison of sweet:bitter ratios between Trial 5 [Q + S] and Trial 3 [Q + C]. | | | | | | | | | | |
|---|---|---|---|---|---|---|---|---|---|---|---|
| | Time (s) | | | | | | | | | | |
| | 0 | 10 | 20 | 30 | 40 | 50 | 60 | 70 | 80 | 90 | 100 |
| Sweet:Bitter Ratio | 104.6 | 140.4 | 100.0 | 131.3 | 124.1 | 123 | 200 | 298.4 | 760 | 861.5 | 937.5 |

Figure 19:
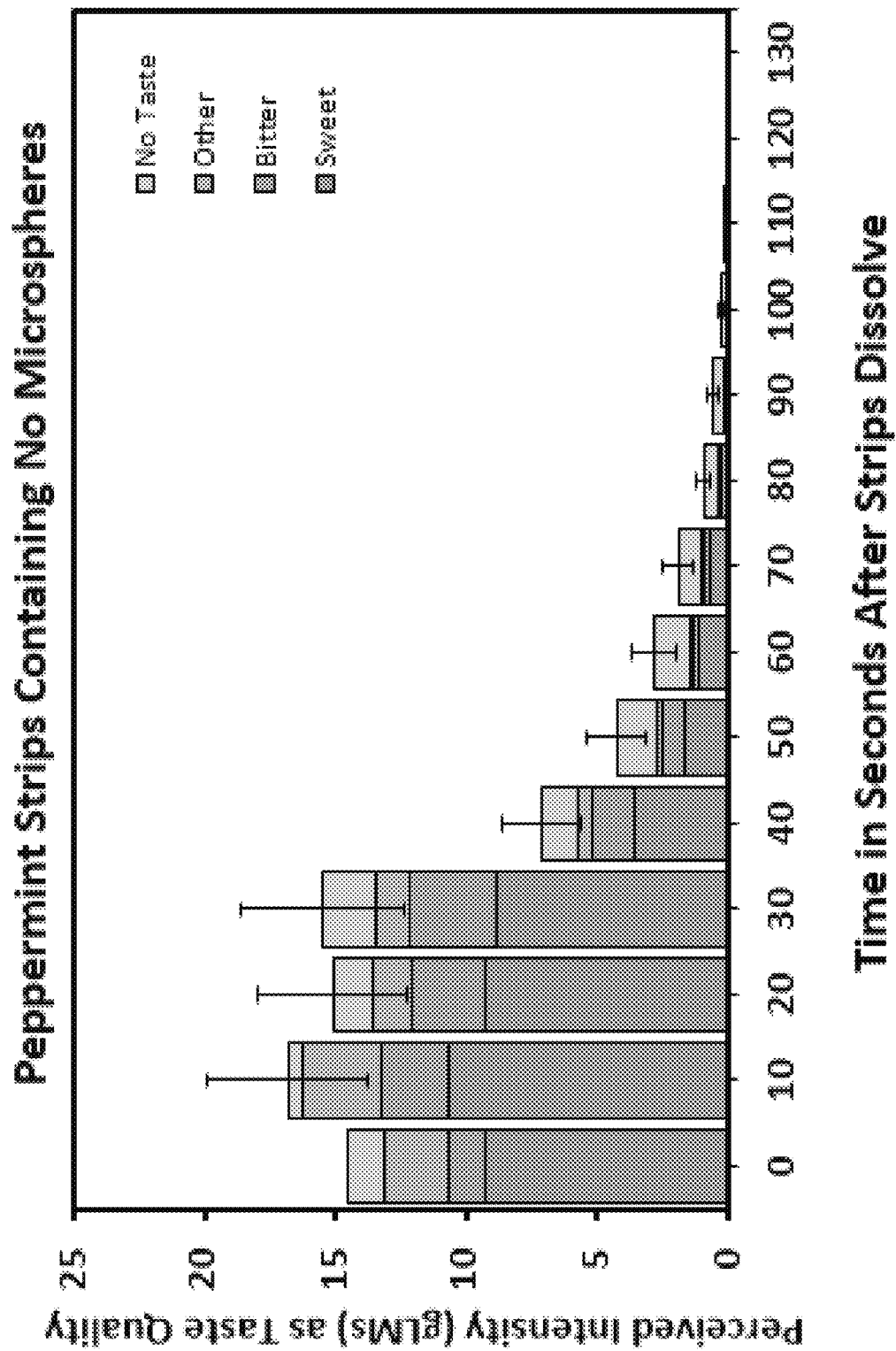
FIG. 19 depicts a graph demonstrating the overall taste intensity as a function of time in seconds after the strips dissolve in the oral cavity for trial 6, edible strips that contain no microspheres.
Figure 20:
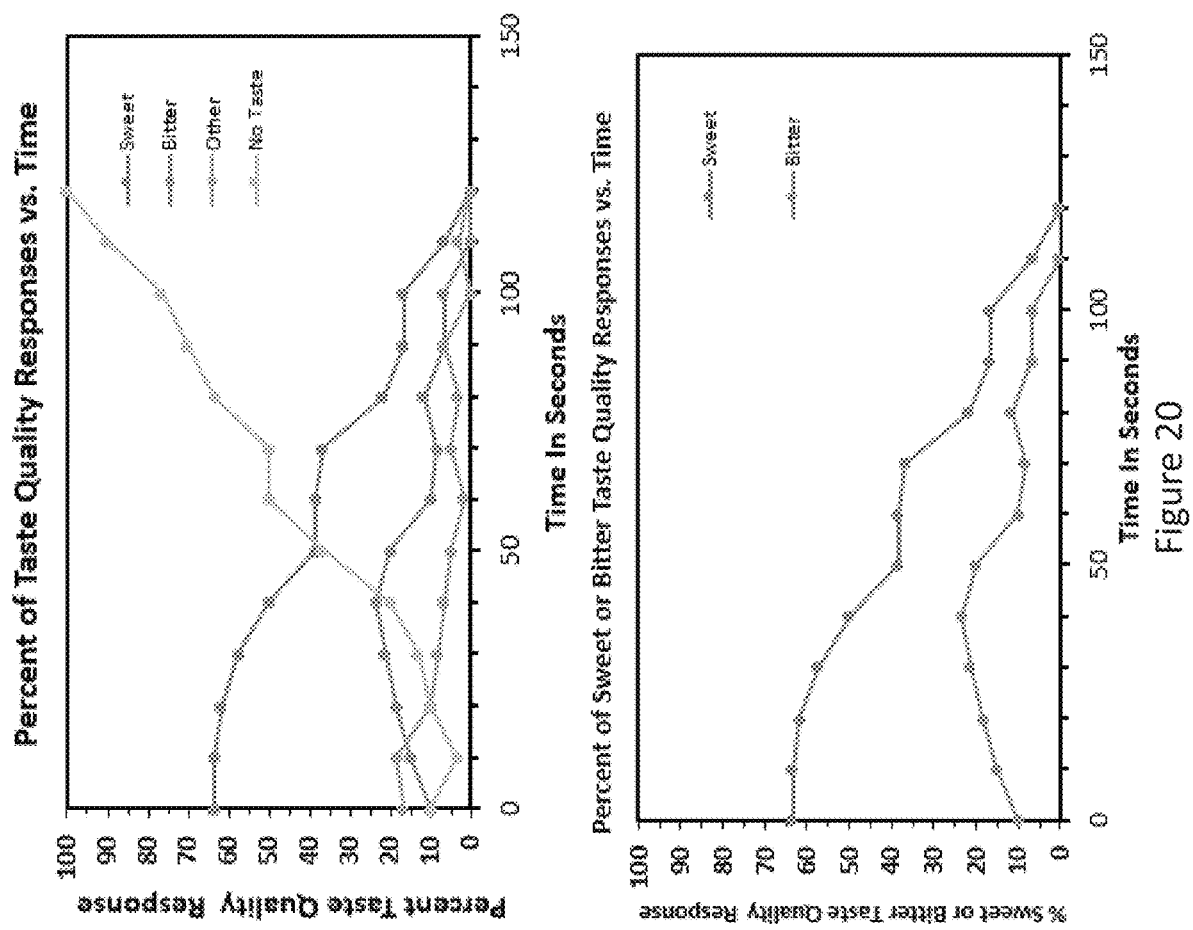
FIG. 20 depicts graphs demonstrating the proportion of taste quality responses (sweet, bitter, other taste, or no taste on the left, or sweet and bitter taste only on the right) as a function of time after the strips dissolve in the oral cavity for trial 6, edible strips that contain no microspheres.

Finally, the fourth experiment (Trial 6) represents a positive control. These edible strips contained no microspheres, and this control was carried out to identify taste intensity (FIGS. 19-20) and taste quality responses in the peppermint oil-sucralose film base alone. The average taste intensity as a function of time was less than that of edible strips that contained lipid microspheres, and indicates that microspheres were releasing their taste stimuli into the oral cavity. The data also demonstrate that the mean taste intensity decreased rapidly in strips that contain no microspheres (similar to Trial 1 with control microspheres). These results further suggest that compounds encapsulated in microspheres show a delayed release as the microspheres "dissolve" in the oral cavity. Finally, edible strips with no microspheres resulted in a strong sweet taste response that was caused by the inclusion of sucralose, mannitol, and glycerol (and possibly peppermint oil) in the pullulan film base (FIGS. 19-20). Finally, the peppermint oil may be responsible for the small bitter taste component in these strips.

TABLE 7

Edible Strips with No Microspheres.

| | Time (s) | | | | | | | | | | | | |
|---|---|---|---|---|---|---|---|---|---|---|---|---|---|
| | 0 | 10 | 20 | 30 | 40 | 50 | 60 | 70 | 80 | 90 | 100 | 110 | 120 |
| Sweet:Bitter Ratio | 6.33 | 4.22 | 3.36 | 2.69 | 2.14 | 1.92 | 3.83 | 4.40 | 1.86 | 2.50 | 2.50 | — | — |

Figure 21:
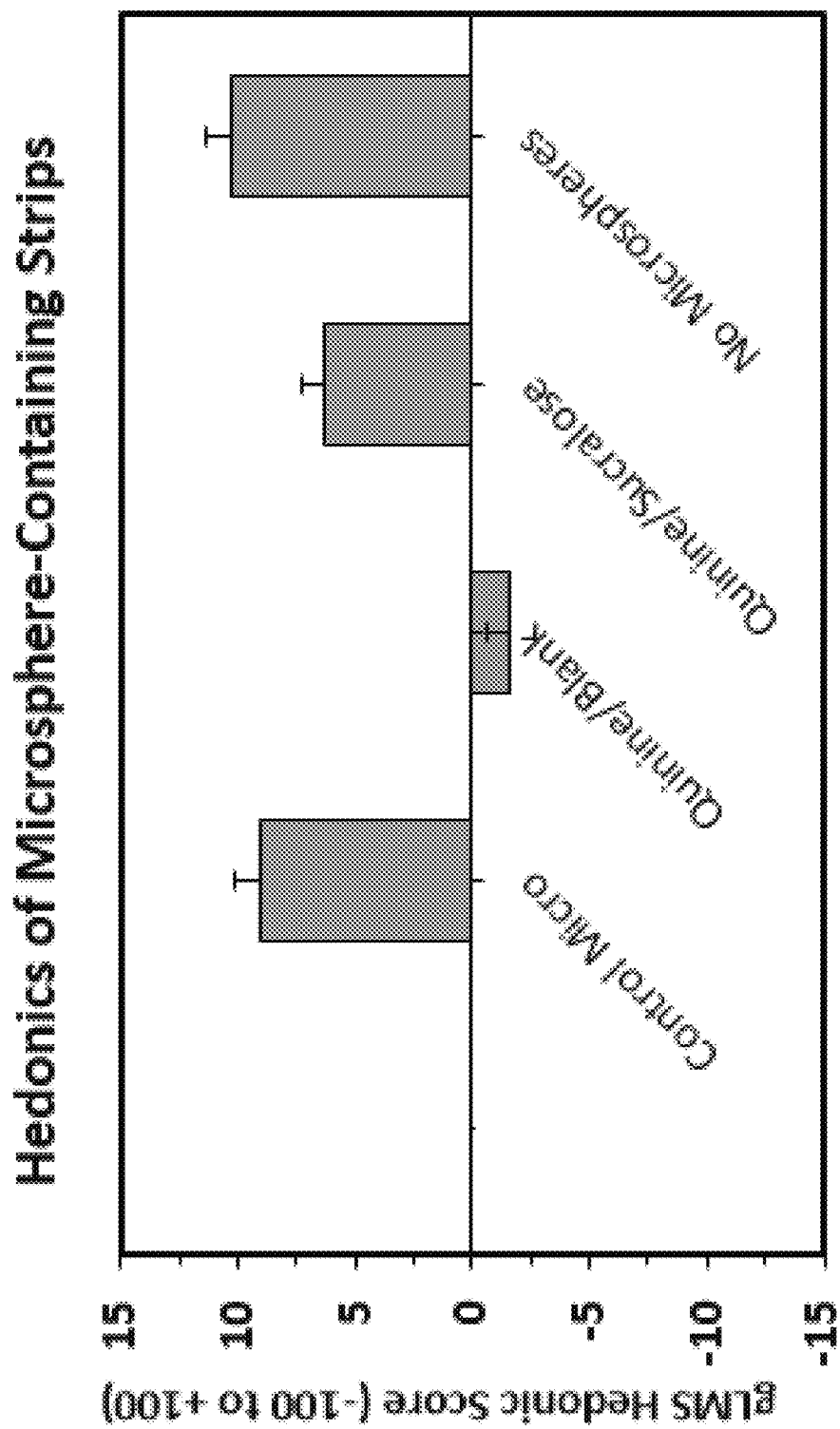
FIG. 21 depicts a graph demonstrating the average hedonic scores (pleasantness score) of the four different taste strips (trials 1, 3, 5, and 6). (N=12).

FIG. 21 show the average hedonic (pleasantness) values of the four different experiments with taste strips shown in Table 2. The hedonics scale ranged from −100 to +100, with negative values representing unpleasant taste sensations, and positive values representing pleasant taste sensations. Edible strips with blank (control) microspheres, and edible strips with no microspheres exhibited an overall pleasant response near +10 of our scale. This value corresponds to a response between weakly pleasant and moderately pleasant. Only edible strips that contained both control and quinine-containing microspheres showed a negative pleasantness value (weakly unpleasant). However, the replacement of control (blank) microspheres with sucralose-containing microspheres reversed this condition (Trial #5, and column 3 of FIG. 21), and yielded an overall positive hedonic score of +6 to +7, which corresponds to weakly pleasant on the hedonics scale. These results indicate that sucralose-containing microspheres diminish the bitter taste of quinine HCl that is released from quinine microspheres after the film base dissolves in the oral cavity. These results further show that sweet taste stimuli in both the film base and in sucralose microspheres assist in minimizing and delaying bitter taste responses as microspheres "dissolve" (release their contents) in the oral cavity. A similar situation should occur when quinine HCl is replaced by bitter tasting drugs in stearic acid microspheres that are embedded in edible films.

Figure 22:
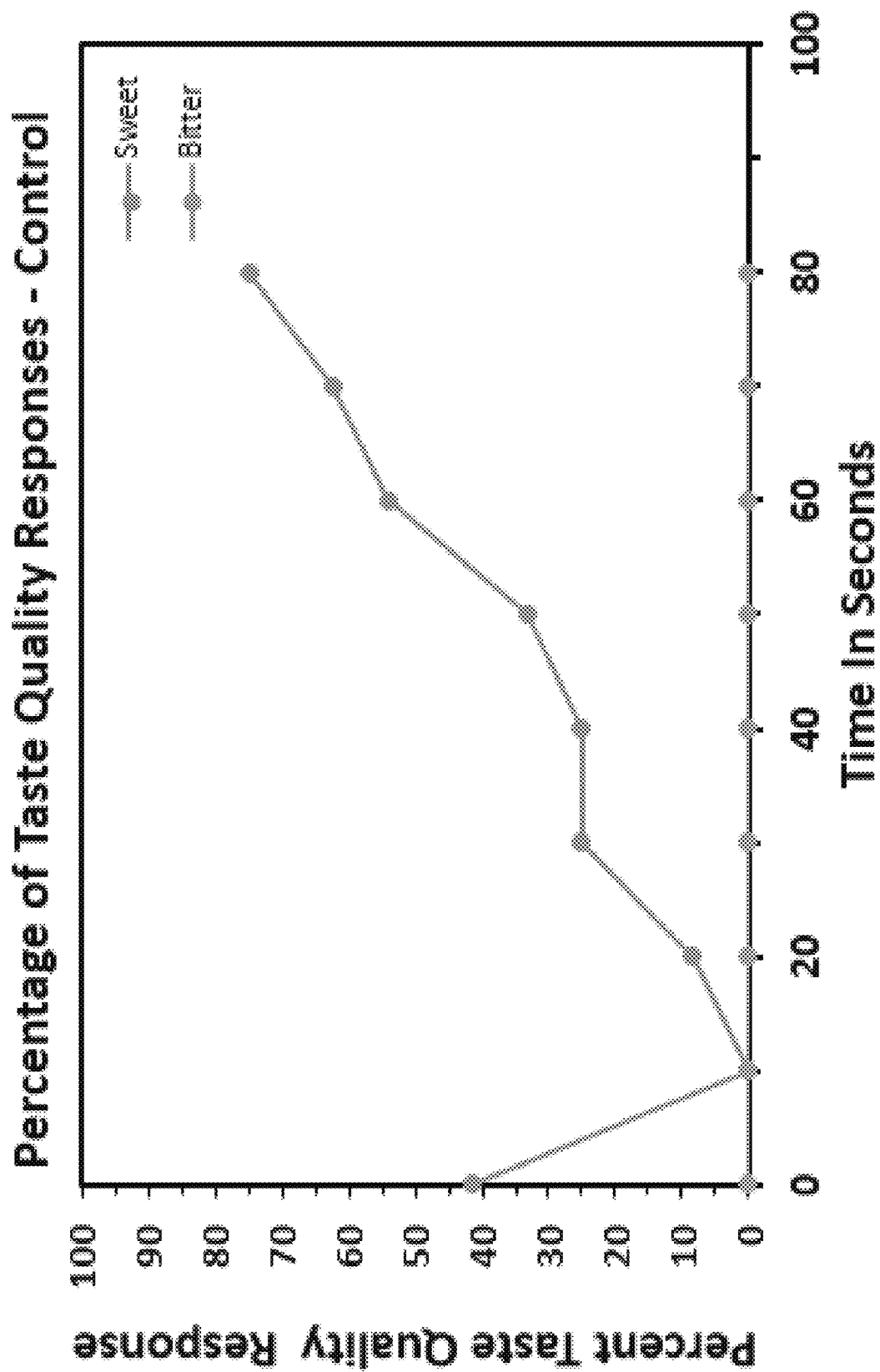
FIG. 22 depicts a graph demonstrating the taste quality responses as a function of time.

Example 8: Psychophysical Testing of Microspheres that Contain the Bitter Tasting Compound Sucrose Octaacetate Sucrose octaacetate (SOA) exhibits a strong bitter taste in humans, and this compound can be readily incorporated into stearic acid microspheres. The second taste study involved the addition of either control (blank) microspheres or sucrose octa-acetate-containing microspheres to peppermint-containing edible films. FIG. 22 demonstrates that improvements in this technique have essentially eliminated bitter taste quality responses in our edible films that contain only control (blank) microspheres. Edible strips with control microspheres primarily caused a sweet taste response or a no taste response (and no bitter taste response) in our subject population.

Figure 23:
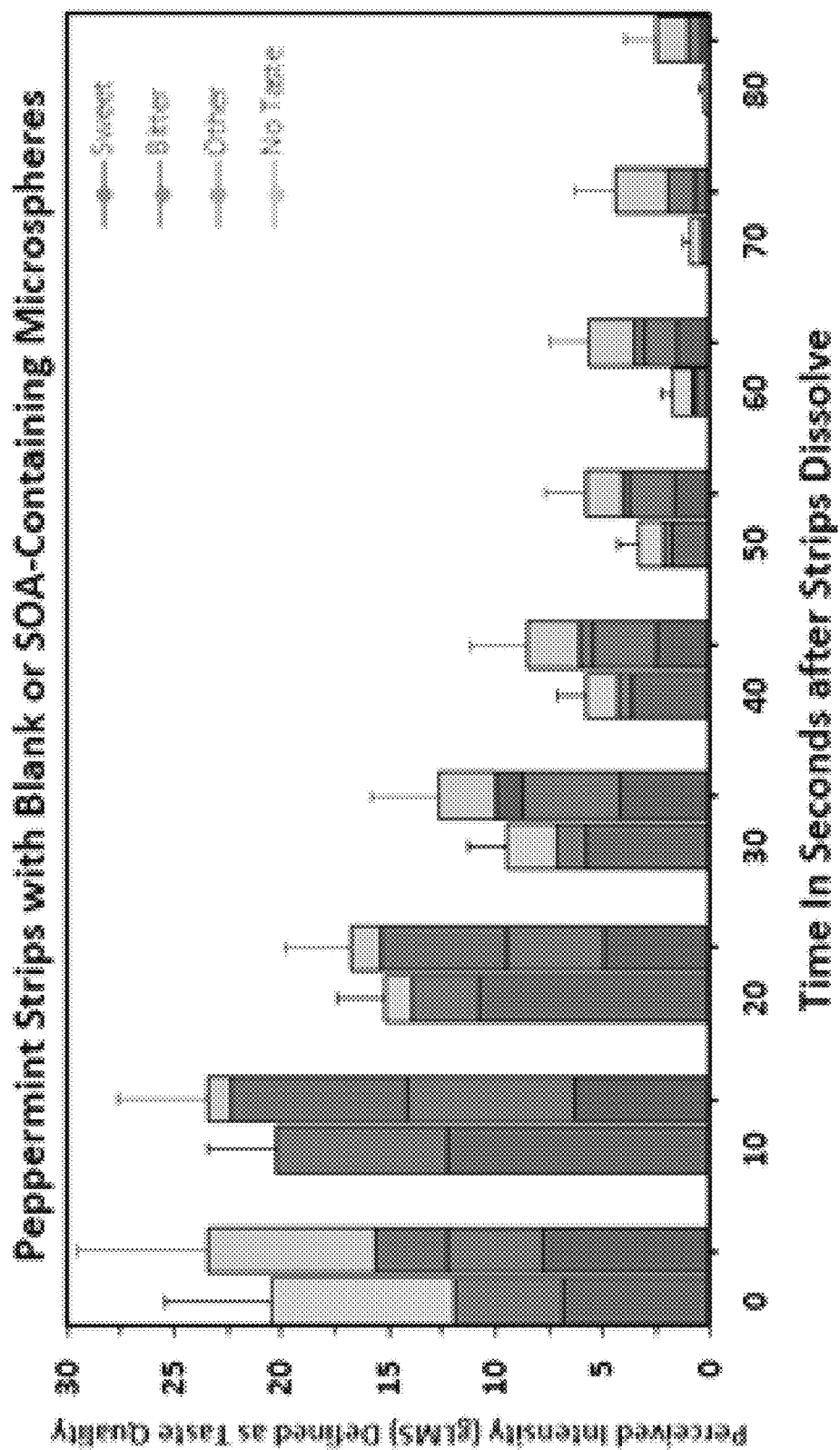
FIG. 23 depicts a graph demonstrating the perceived intensity of peppermint strips with blank or SOA-containing microspheres. Edible strips containing blank microspheres are in column one. Edible strips containing SOA microspheres are in column two.

The replacement of blank microspheres with SOA-containing microspheres in these edible films caused only a small increase in overall taste intensity as a function of time (FIG. 23). As expected, the SOA-containing microspheres caused a bitter taste response in the subject population with approximately one-third of the taste quality responses reported as bitter (FIG. 23). These results also suggest that the bitter taste of SOA is suppressed in these edible films. These SOA microspheres also suppressed overall sweet taste responses (from sucralose, mannitol, and glycerol in the film base) in our subject population.

Figure 24:
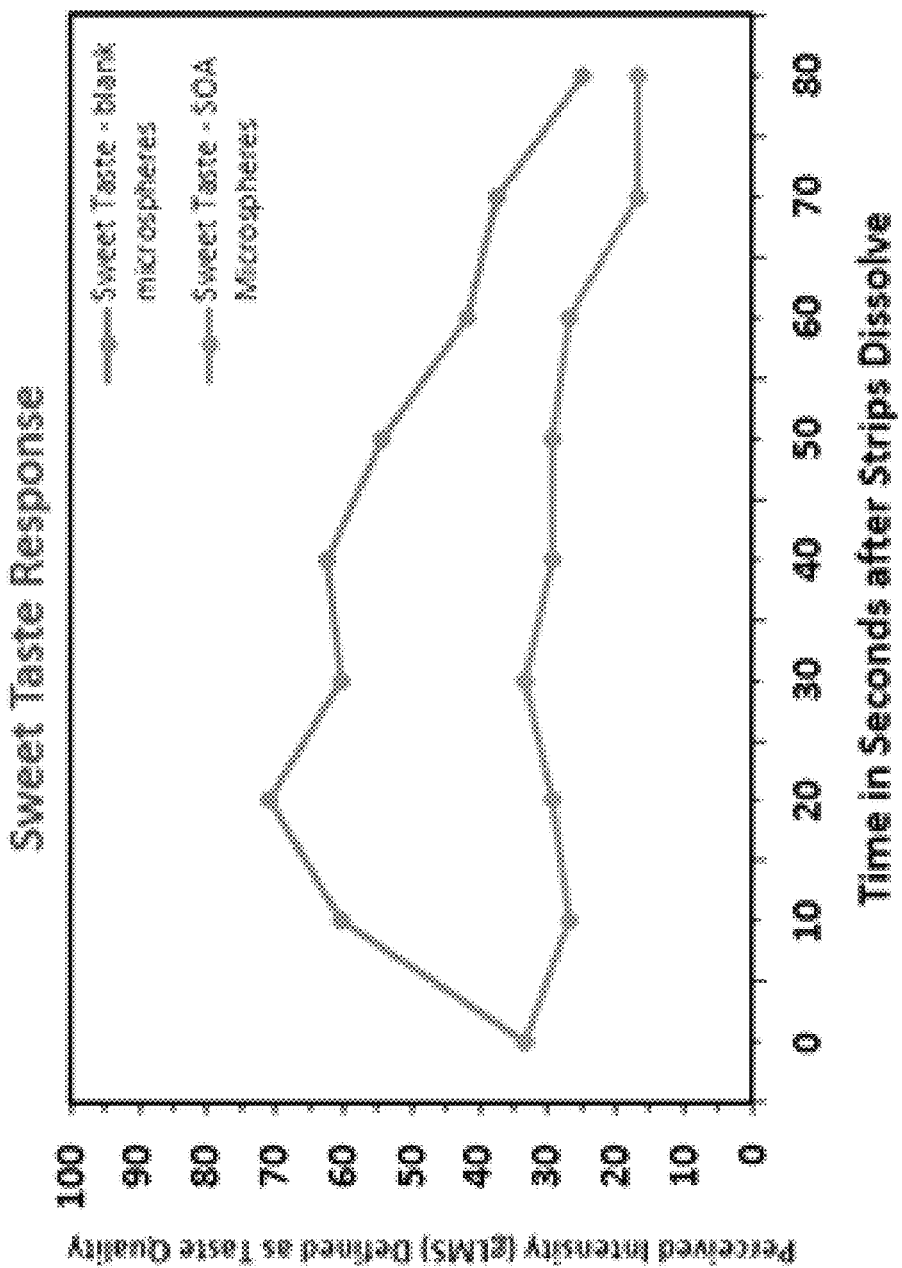
FIG. 24 depicts a graph demonstrating the perceived intensity of peppermint strips with blank or SOA-containing microspheres as a function of time in seconds after edible strips dissolve in the oral cavity.

However, the sweet taste to bitter taste quality ratios remained near 1.0 at all the time points after the strips dissolved in the oral cavity (zero point on the horizontal axis). This occurred in the absence of sucralose-containing microspheres in the film base. These results indicate that even in the absence of sucralose-containing microspheres, the bitter taste of SOA is suppressed by sweet taste stimuli (and possibly peppermint oil) in the pullulan film base. FIGS. 23-24 describe the percentage responses of sweet taste and bitter taste in edible strips that contain control microspheres (first column) or SOA microspheres (second column for each time point) as a function of time in seconds after edible strips dissolve in the oral cavity.

Figure 25:
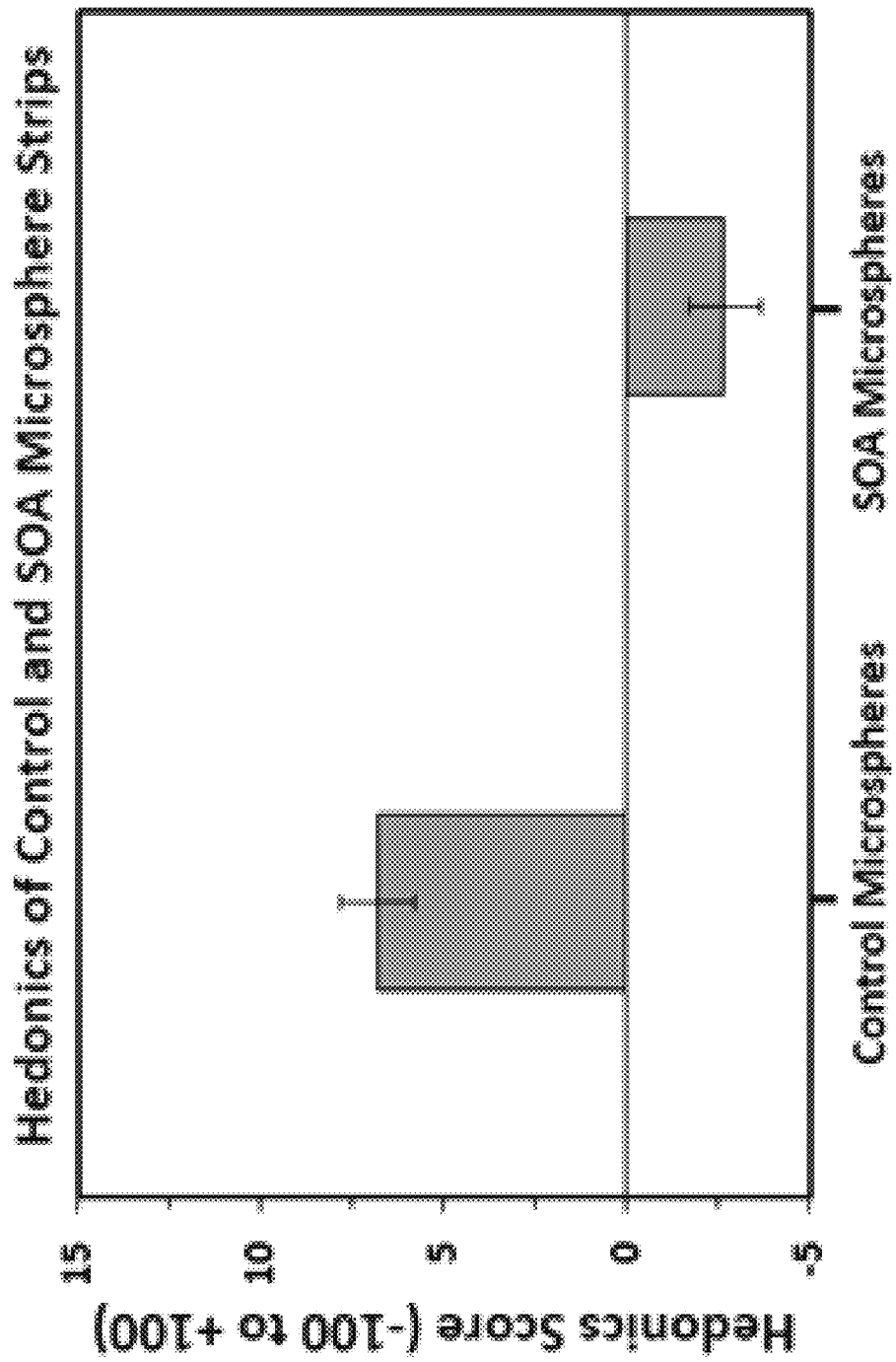
FIG. 25 depicts a graph demonstrating the hedonic rating of taste strips with control microspheres and SOA microspheres.

Finally, edible strips with embedded SOA-encapsulated microspheres (and no sucralose microspheres) yielded a "weakly dislike" pleasantness value in our subject population (n=12). In addition, taste strips with control (blank) microspheres yielded a mildly pleasant hedonic rating (FIG. 25). These results further suggest that edible films that contain peppermint oil, sucralose, mannitol, and glycerol in the film base help to suppress the unpleasant bitter taste of SOA when this bitter taste stimulus is released from microspheres in the oral cavity.

Example 9: Capsaicin Microspheres

Capsaicin is the spicy component of hot chicken wings and chili. Capsaicin and dihydrocapsaicin are hydrophobic and do not dissolve in water. Due to their hydrophobicity, these vanilloid compounds can be efficiently encapsulated in stearic acid microspheres by the hot melt encapsulation method. The resulting microspheres are then embedded within edible taste strips for the delayed release of capsaicin into the oral cavity in order to treat oral pain. Also, encapsulated capsaicin (that is not embedded into edible films) added to lotions or creams allow for timed release of this vanilloid for the treatment of joint or muscle pain. Finally, capsaicin-containing microspheres added to pepper sprays for are useful for self-protection.

Example 10: Phytonutrient Encapsulated Microspheres

Phytonutrients are plant products that show health benefits in humans. These compounds help plants to grow, or to thwart competitors, predators, or pathogens. Phytonutrients include carotenoids (antioxidants), lycopene, lutein and zeaxanthin (eye health), ellagic acid, catechins, flavonoids, flavinols, resveratrol (heart health), glucosinolates, and phytoestrogens. Many of these compounds can be successfully incorporated into lipid microspheres and embedded in films for the production of a commercial product.

Example 11: Lipid Microsphere Encapsulation of Herbicides and Pesticides for Increased Safety In order to increase the safety and handling of pesticides and herbicides, a representative organic pesticide and herbicide has been encapsulated herein within stearic acid microspheres. Stearic acid is an 18-carbon saturated fatty acid that is a lipid component of plasma membranes and serum lipoproteins of living organism. This fatty acid has a melting point of 69° C., and is useful for encapsulating a wide variety of molecules. Along with stearic acid, several different lipids and oils have been incorporated into microspheres in order to modulate the melting temperature of these microspheres so that the release of pesticides and herbicides can be more readily controlled by temperature. The pesticide and herbicide 2,4-dinitrophenol (2,4-D) is a mitochondrial electron transport uncoupler that is widely used to control animal pests. The photosynthetic inhibitor DCMU is an important herbicide that is used to control plant growth. It is demonstrated herein that these two model compounds can be successful incorporated into lipid microspheres with no apparent chemical degradation. The encapsulation of herbicides and pesticides within water insoluble lipid microspheres will allow the safe handling and dissemination of these pesticides and herbicides in the environment, and will also decrease the volatilization of these compounds. Finally, lipid encapsulation of these environmental toxins may increase the stability and shelf life of the compound that is encapsulated.

The hot melt method was used to prepare stearic acid microspheres that encapsulated an herbicide or a pesticide. Briefly, the compound to be encapsulated and stearic acid along with an oil such as linoleic acid or coconut oil are melted together at a temperature just above the melting point of the molecule to be encapsulated, mixed, and poured into a rapidly stirring solution of HEPES buffer at 60° C. The mixture is then cooled for 15 minutes. The resulting microspheres are precipitated by centrifugation, or collected by vacuum filtration on Whatman #1 filter paper, washed with HEPES buffer (pH 8.0), and finally washed with approx. 120 ml of sterile water. Microspheres are dried overnight in a vacuum oven just above room temperature, or air dried in the dark at room temperature for 24 hours. The dried microspheres are stored at 4° C. in the dark until use.

After drying, loaded microspheres are dissolved in a solvent such as acetonitrile or acetonitrile/HEPES, and the encapsulated compound is assayed by absorption spectroscopy, fluorescence emission, or infra-red spectroscopy. The melting point is then measured in order to identify the melting point range of the microspheres. If needed, these lipid microspheres could be embedded within pullulan-based films for long term storage. Stearic acid microspheres encapsulate 2,4-D or DCMU (Diuron) at a weight to weight ratio of approximately 15:I. In addition, the melting point of lipid microspheres is lowered to 38-40° C. for the controlled release of these compounds from microspheres. The melting temperature range varies from 8 to 10° C.

Glyphosate (N-(phosphonomethyl)glycine) is a broad-spectrum herbicide. Glyphosate powder has a melting point of 185° C., and this carbon-containing compound should be easily encapsulated by microspheres, and solubilized with organic solvent for subsequent use.

Household insecticide sprays contain pyrethroids as active ingredients. These organic compounds should be amenable to encapsulation by lipid microspheres. In addition, the naturally occurring protein BT toxin (molecular weight~70 kilodaltons) from *Bacillus thuringensis* that is used to control insect larvae may also be amenable to lipid encapsulation.

Figure 26:
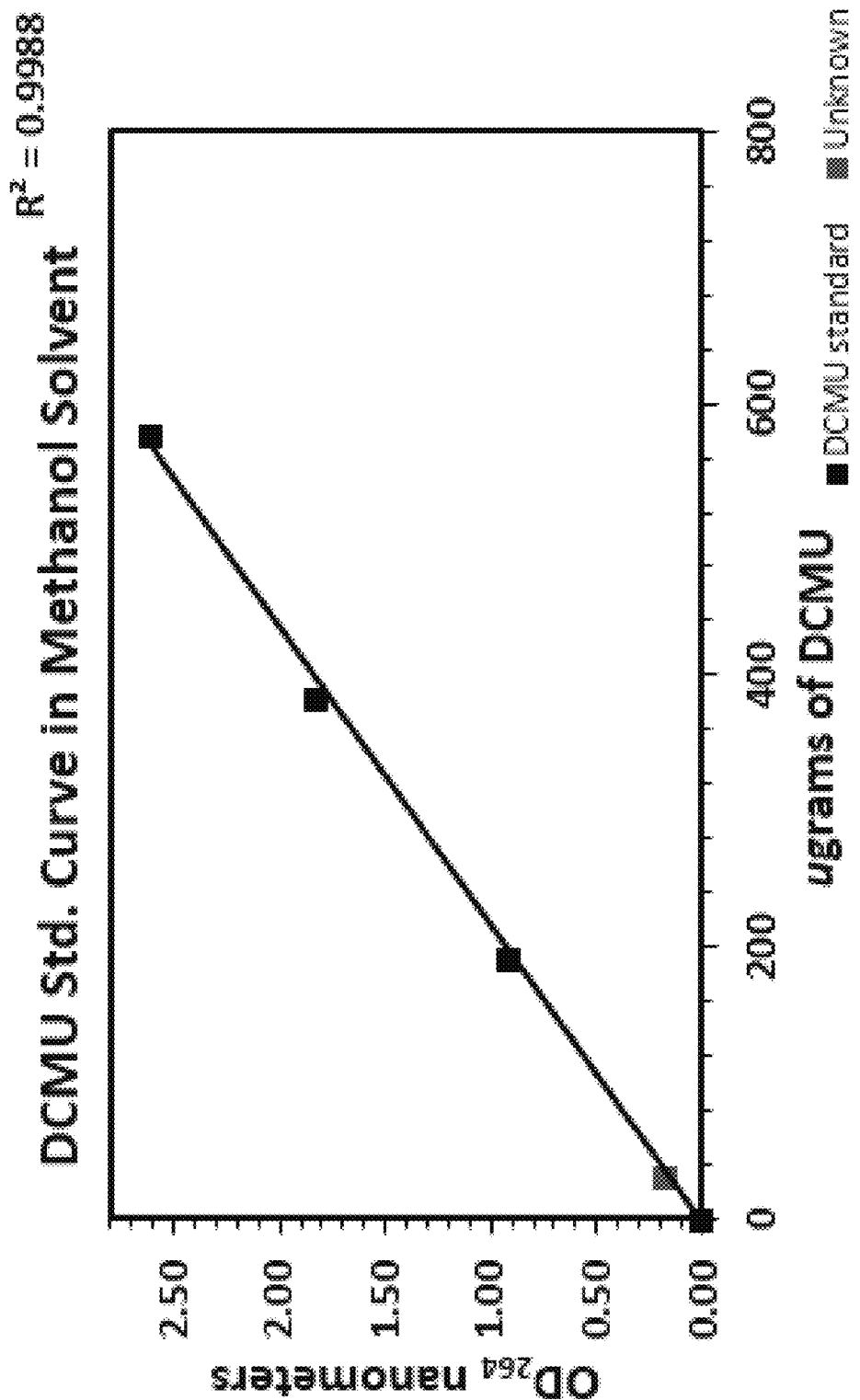
FIG. 26 depicts the DCMU standard curve. The known amounts of DCMU were dissolved in 100% methanol (black squares), and measured by UV absorbance at 264 nm. Red square represents the amount of DCMU within microspheres of known weight after microspheres are dissolved in methanol.
Figure 27:
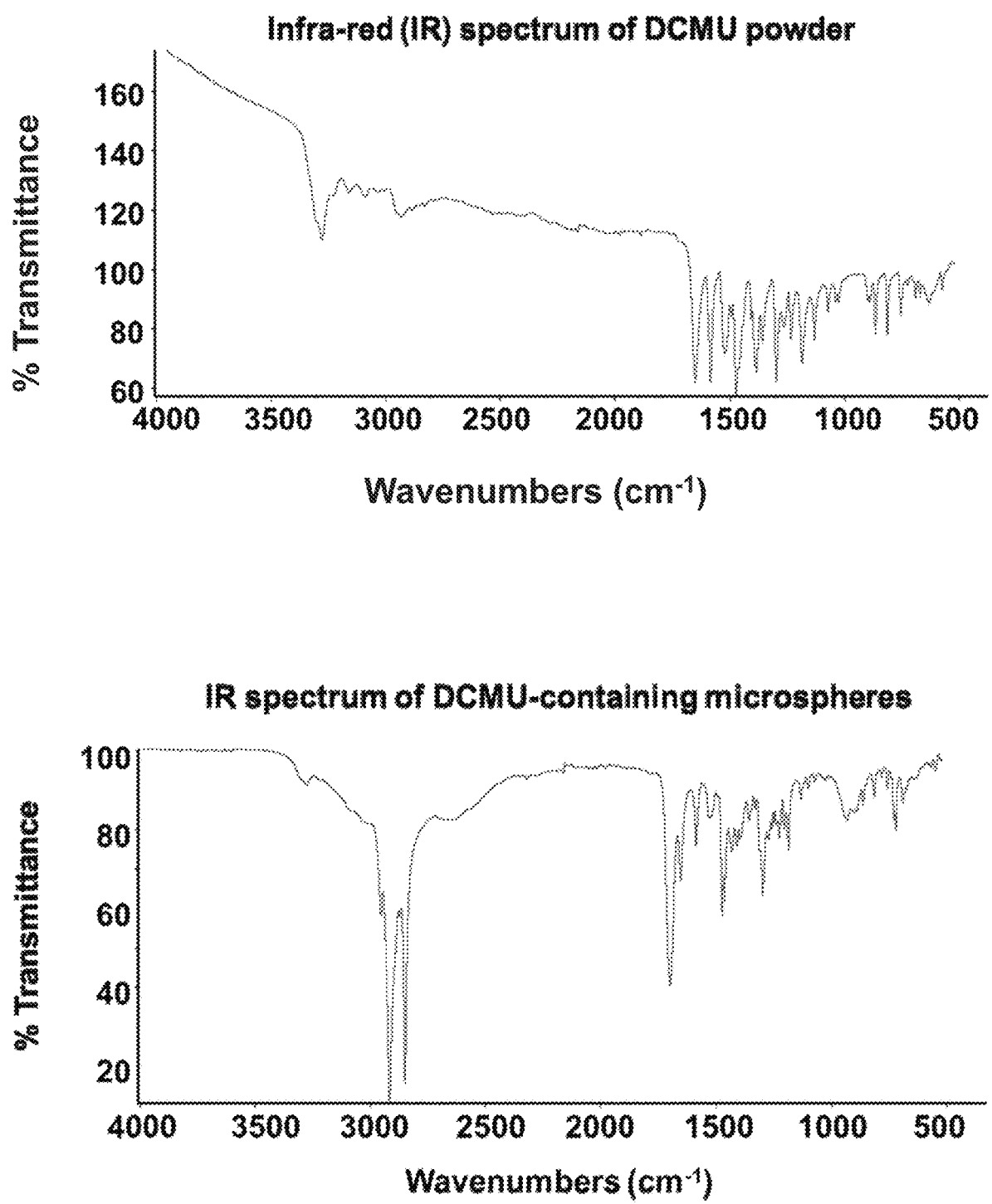
FIG. 27 depicts the infa-red (IR) spectrum of DCMU powder and DCMU-containing microspheres.

The photosynthetic electron transport inhibitor DCMU (Diuron) was readily incorporated into stearic acid microspheres at pH 8.0. When dissolved in 100% methanol, an assay of dissolved microspheres indicated a weight ratio 3:1 stearic acid to DMCU (n=1 trial) (FIGS. 26-27). The efficient encapsulation of DCMU is readily apparent by examining the IR spectra of DCMU and solid microspheres between 1600 and 500 $cm^{-1}$ (FIG. 27). The IR data further show that DCMU is undegraded after encapsulation.

Figure 28:
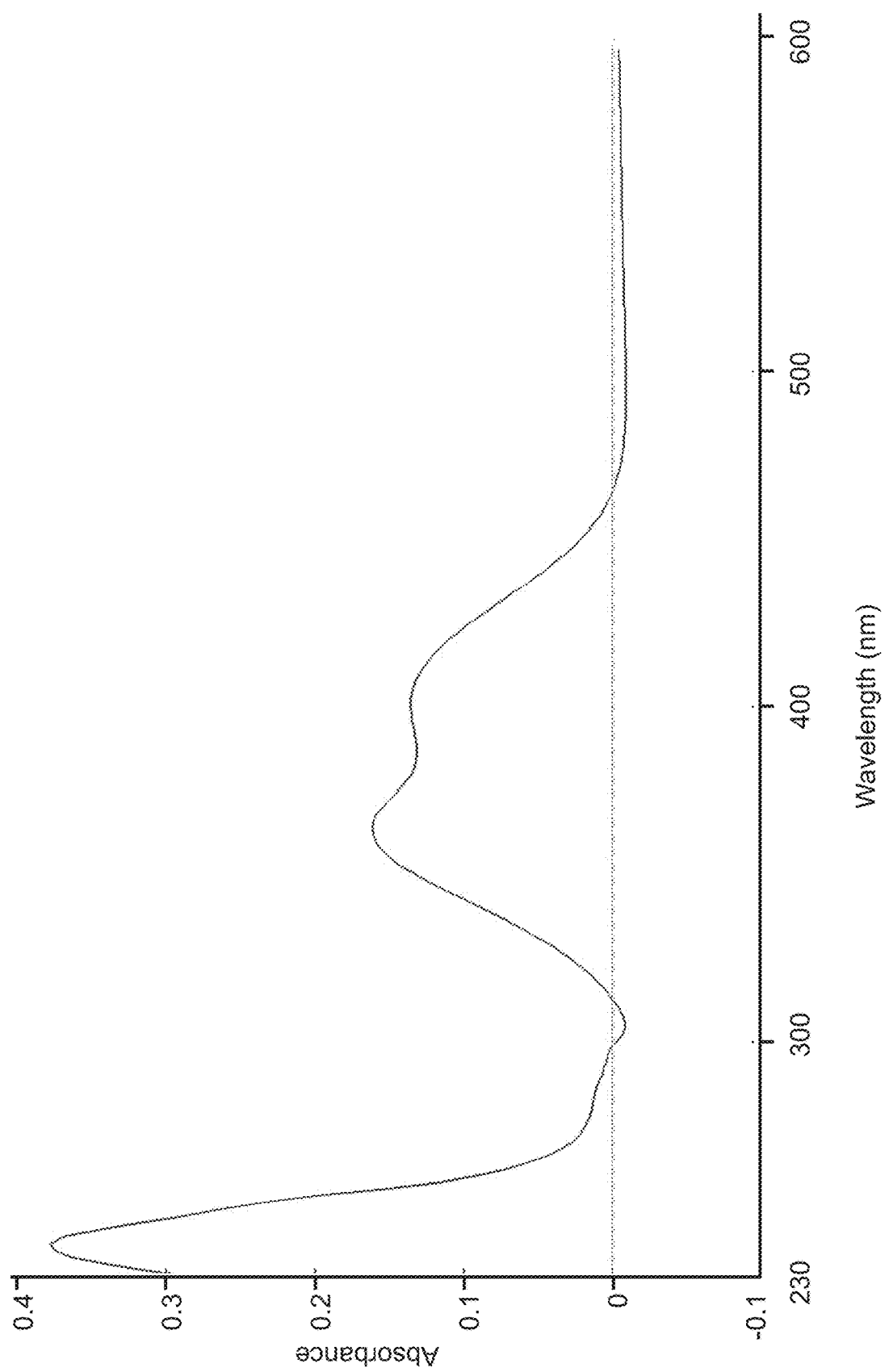
FIG. 28 depicts the absorption spectrum of 2,4-dinitrophenol (2,4-D)-containing microspheres in a double-beam spectrophotometer. Solvent used to dissolve microspheres was 80% acetonitrile/20% HEPES at pH 8.0. A $\lambda_{max}$ of 365 nanometers used for assay.
Figure 29:
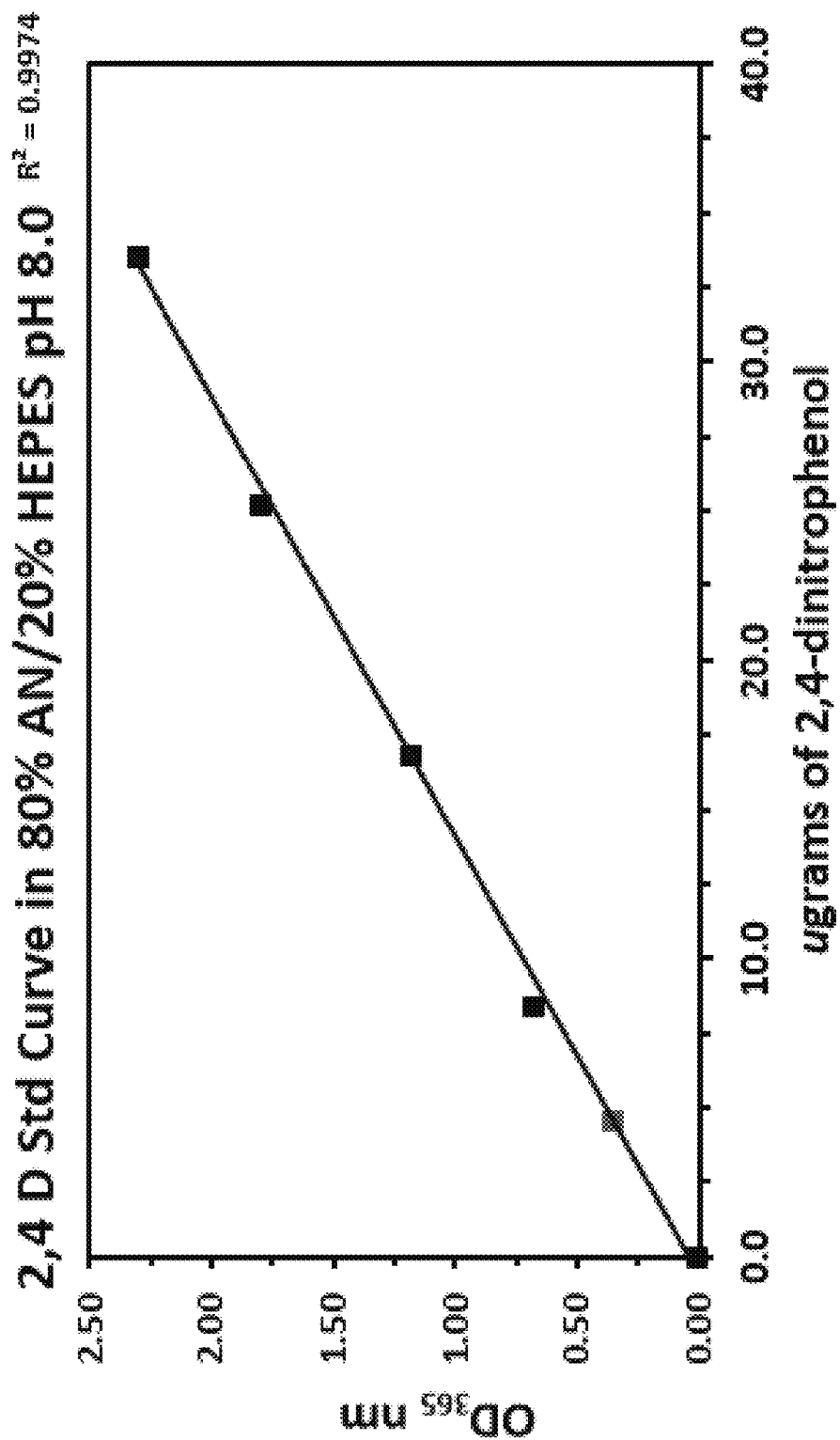
FIG. 29 depicts the 2,4-D standard curve. The red square represents the amount of 2,4-dinitrophenol encapsulated within stearic acid microspheres. The stearic acid to 2,4-dinitrophenol weight to weight ratio was 10.3:1.
Figure 30:
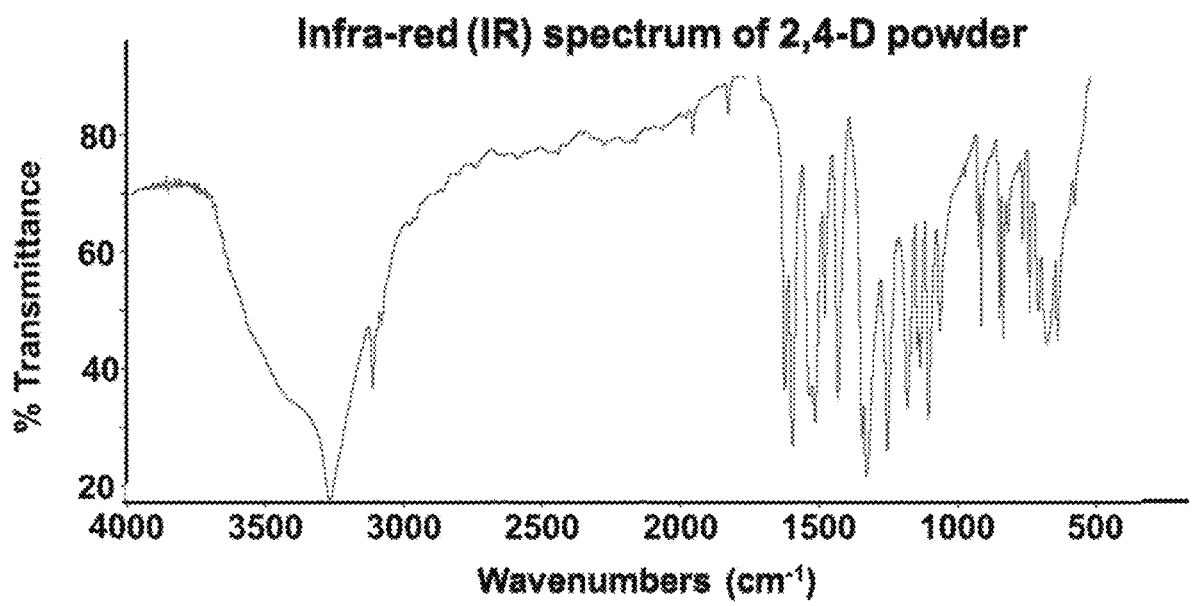
FIG. 30 depicts the (IR) spectrum of 2,4-D powder and 2,4-D-containing microspheres.
Figure 30:
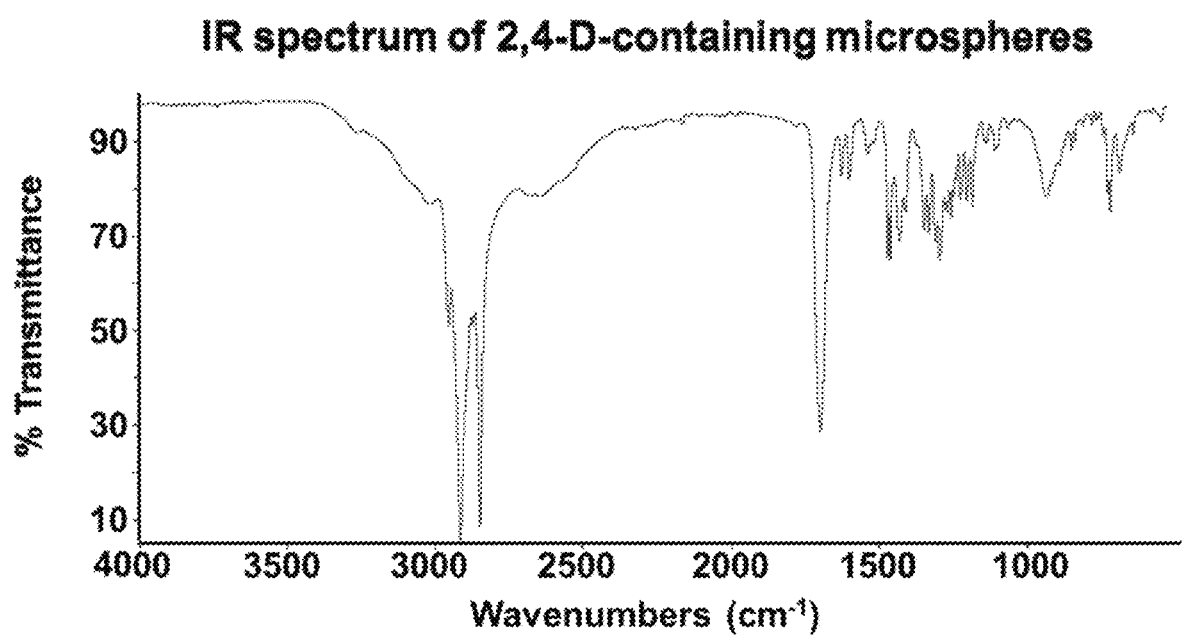

The proton ionophore 2,4-dinitrophenol is widely used as a pesticide (and herbicide) due to its ability to inhibit mitochondrial function. This compound was readily incorporated into stearic acid microspheres at either pH 4.25 in 5 mM sodium acetate buffer, or pH 8.0 in 5 mM HEPES buffer. FIG. 28 shows an absorption spectrum of 2,4-dinitrophenol microspheres prepared at pH 8.0 after the microspheres are dissolved in acetonitrile-HEPES buffer. Encapsulation ratios at pH 8.0 yielded median weight to weight ratios of 11.22 stearic acid to 2,4-dinitrophenol (n=2 trials) when microspheres were dissolved in acetonitrile-HEPES buffer at pH 8. Encapsulation ratios of 2,4-dinitorphenol at pH 4.25 were slightly higher (less encapsulation), with a wt:wt ratio of 7.95:1 stearic acid to 2,4-dinitrophenol (n=1 trial) (FIG. 29). Finally, the IR data indicate that 2,4-dinitrophenol is not degraded after encapsulation within microspheres (FIG. 30).

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A microsphere comprising a sweetener and at least one material selected from the group consisting of a fatty acid, glycerol, esters, or a combination thereof, wherein the microsphere further comprises elaidic acid or glyceryl dibehenate.

2. The microsphere of claim 1, wherein the microsphere further comprises stearic acid.

3. The microsphere of claim 2, wherein the microsphere further comprises a lipid.

4. The microsphere of claim 3, wherein the lipid is selected from the group consisting of linoleic acid, cocoa butter, and coconut oil.

5. The microsphere of claim 2, wherein the sweetener is selected from the group consisting of an artificial sweetener, a sugar alcohol, and a natural sweetener.

6. The microsphere of claim 5, wherein the sweetener is sucralose.

7. An edible material comprising at least one microsphere comprising at least one material selected from the group consisting of a fatty acid, glycerol, esters, or a combination thereof, wherein the microsphere further comprises elaidic acid or glyceryl dibehenate.

8. The edible material of claim 7, comprising a therapeutic agent.

9. The edible material of claim 8, wherein the therapeutic agent is selected from the group consisting of a protein, a peptide, a peptidomimetic, an antibody, a ribozyme, a small molecule chemical compound, a nucleic acid, a plasmid vector, and an antisense nucleic acid molecule.

10. The edible material of claim 7, wherein the edible material comprises a microsphere comprising an agent and a microsphere comprising a sweetener.

11. The edible material of claim 7, wherein the edible material is selected from the group consisting of an edible oral strip, a gummy candy, a hard candy, chocolate, sugar-free chocolate, ice cream, pudding, apple sauce, and yogurt.

12. The edible material of claim 7, comprising an imaging agent.

13. The edible material of claim 7, comprising a diagnostic agent.

14. The edible material of claim 7, comprising a contrast agent.

15. The edible material of claim 7, comprising a labeling agent.

* * * * *